(12) United States Patent
Metzker et al.

(10) Patent No.: US 11,299,769 B2
(45) Date of Patent: Apr. 12, 2022

(54) TARGET REPORTER CONSTRUCTS AND USES THEREOF

(71) Applicant: RedVault Biosciences, LP, Houston, TX (US)

(72) Inventors: Michael L. Metzker, Houston, TX (US); Christopher August Weier, Houston, TX (US)

(73) Assignee: REDVAULT BIOSCIENCES, LP, Houston, TX (US)

( * ) Notice: Subject to any disclaimer, the term of this patent is extended or adjusted under 35 U.S.C. 154(b) by 655 days.

(21) Appl. No.: 15/614,958

(22) Filed: Jun. 6, 2017

(65) Prior Publication Data

US 2017/0349939 A1   Dec. 7, 2017

Related U.S. Application Data

(60) Provisional application No. 62/346,334, filed on Jun. 6, 2016.

(51) Int. Cl.

| | |
|---|---|
| *C12Q 1/68* | (2018.01) |
| *C12Q 1/6811* | (2018.01) |
| *C12Q 1/6844* | (2018.01) |
| *C12Q 1/70* | (2006.01) |
| *C12Q 1/6806* | (2018.01) |
| *C12Q 1/6809* | (2018.01) |
| *C12Q 1/6837* | (2018.01) |
| *C12Q 1/6853* | (2018.01) |
| *C12Q 1/686* | (2018.01) |
| *C12Q 1/6869* | (2018.01) |
| *C12Q 1/6876* | (2018.01) |

(52) U.S. Cl.
CPC ............ *C12Q 1/6811* (2013.01); *C12Q 1/686* (2013.01); *C12Q 1/6806* (2013.01); *C12Q 1/6809* (2013.01); *C12Q 1/6837* (2013.01); *C12Q 1/6844* (2013.01); *C12Q 1/6853* (2013.01); *C12Q 1/703* (2013.01); *C12Q 1/6869* (2013.01); *C12Q 1/6876* (2013.01); *C12Q 2600/178* (2013.01)

(58) Field of Classification Search
CPC .................................................. C12Q 1/6853
See application file for complete search history.

(56) References Cited

U.S. PATENT DOCUMENTS

| | | |
|---|---|---|
| 5,641,658 A | 6/1997 | Adams et al. |
| 5,648,211 A | 7/1997 | Fraiser et al. |
| 5,714,320 A | 2/1998 | Kool |
| 5,854,033 A | 12/1998 | Lizardi |
| 6,107,023 A | 8/2000 | Reyes et al. |
| 6,451,563 B1 | 9/2002 | Wittig et al. |
| 6,498,023 B1 | 12/2002 | Abarzua |
| 6,664,079 B2 | 12/2003 | Ju et al. |
| 6,833,246 B2 | 12/2004 | Balasubramanian |
| 7,057,026 B2 | 6/2006 | Barnes et al. |
| 7,115,400 B1 | 10/2006 | Adessi et al. |
| 7,232,656 B2 | 6/2007 | Balasubramanian et al. |
| 7,282,328 B2 | 10/2007 | Kong et al. |
| 7,345,159 B2 | 3/2008 | Ju et al. |
| 7,351,532 B2 | 4/2008 | Swerdlow et al. |
| 7,368,265 B2 | 5/2008 | Brenner et al. |
| 7,427,673 B2 | 9/2008 | Balasubramanian et al. |
| 7,541,444 B2 | 6/2009 | Milton et al. |
| 7,592,435 B2 | 9/2009 | Milton et al. |
| 7,622,279 B2 | 11/2009 | Ju |
| 7,662,594 B2 | 2/2010 | Kong et al. |
| 7,785,796 B2 | 8/2010 | Balasubramanian et al. |
| 7,829,284 B2 | 11/2010 | Kong et al. |
| 8,148,503 B2 | 4/2012 | Litosh et al. |
| 8,329,400 B2 | 12/2012 | Lok |
| 8,703,462 B2 | 4/2014 | Hsieh et al. |
| 9,650,676 B2 | 5/2017 | Nagarkatti et al. |
| 2003/0228611 A1 | 12/2003 | Church et al. |
| 2009/0018024 A1 | 1/2009 | Church et al. |
| 2010/0075384 A1 | 3/2010 | Kong et al. |
| 2010/0136544 A1 | 6/2010 | Agresti et al. |
| 2010/0304982 A1 | 12/2010 | Hinz et al. |
| 2012/0156728 A1 | 6/2012 | Li et al. |

(Continued)

FOREIGN PATENT DOCUMENTS

| | | |
|---|---|---|
| CN | 105349683 | 2/2016 |
| CN | 105349683 A * | 2/2016 |
| EP | 0224126 | 6/1987 |

(Continued)

OTHER PUBLICATIONS

Travers KJ, Chin CS, Rank DR, Eid JS, Turner SW. A flexible and efficient template format for circular consensus sequencing and SNP detection. Nucleic Acids Res. Aug. 2010; 38(15):e159. pp 1-8. Epub Jun. 22, 2010. (Year: 2010).*

Nilsson M, Gullberg M, Dahl F, Szuhai K, Raap AK. Real-time monitoring of rolling-circle amplification using a modified molecular beacon design. Nucleic Acids Res. Jul. 15, 2002; 30(14):e66. pp. 1-7. (Year: 2002).*

Eriksson et al. Multiplex and quantifiable detection of nucleic acid from pathogenic fungi using padlock probes, generic real time PCR and specific suspension array readout. J Microbiol Methods. Aug. 2009; 78(2):195-202. (Year: 2009).*

English Translation of CN105349683A, pub. Feb. 24, 2016, filed Dec. 19, 2015: pp. 1-13. (Year: 2016).*

(Continued)

*Primary Examiner* — Teresa E Strzelecka
*Assistant Examiner* — Olayinka A Oyeyemi
(74) *Attorney, Agent, or Firm* — Parker Highlander PLLC

(57) ABSTRACT

Provided herein are methods and compositions for the detection of target nucleic acids using target reporter constructs (TRCs) which comprise target sequences complementary to the target nucleic acid. Further provided are methods of replicating the TRCs using rolling circle replication and/or rolling circle amplification to produce replicated TRCs which can be detected using probe sequences within the replicated TRCs.

20 Claims, 12 Drawing Sheets
(10 of 12 Drawing Sheet(s) Filed in Color)
Specification includes a Sequence Listing.

(56) References Cited

U.S. PATENT DOCUMENTS

2013/0203607 A1    8/2013   Li et al.
2017/0175190 A1    6/2017   Taylor et al.

FOREIGN PATENT DOCUMENTS

| EP | 0372524 | 6/1990 |
|---|---|---|
| EP | 2857521 | 4/2015 |
| KR | 20160052400 | 5/2016 |
| WO | WO 2007/102006 | 9/2007 |
| WO | WO 2015/148919 | 10/2015 |
| WO | WO 2017/175190 | 10/2017 |

OTHER PUBLICATIONS

Arbuckle and Medveczky, "The molecular biology of human herpesvirus-6 latency and telomere integration," *Microbes and Infection*, 13:731-741, 2011.

Blanco et al., "Highly Efficient DNA Synthesis by the Phase Φ29 DNA Polymerase: Symmetrical Mode of DNA Replication," *The Journal of Biological Chemistry*, 264:8935-8940, 1989.

Browning and Browning, 2011, Haplotype phasing: existing methods and new developments: Nature Reviews Genet., v. 12, p. 703-714.

Burgtorf et al., 2003, Clone-based Systematic Haplotyping (CSH): A procedure for physical haplotyping of whole genomes: Genome Res., v. 13, p. 2717-2724.

Burnett and Ross, 2012, RNA-Based Therapeutics: Current Progress and Future Prospects: Chemistry & Biology, v.19, p. 60-71.

Chan et al., 2004, Size distributions of maternal and fetal DNA in maternal plasma: Clin. Chem., v. 50, p. 88-92.

Chapman et al., 2011, Meraculous: De novo genome assembly with short paired-end-reads: PLoS ONE, v. 6, p. e23501.

Collins and Weissman, 1984, Directional cloning of DNA fragments at a large distance from an initial probe: a circularization method: Proc. Natl. Acad. Sci. USA, v. 81, p. 6812-6816.

Costa and Weiner, 1994, Protocols for Cloning and Analysis of Blunt-ended PCR-generated DNA Fragments: PCR Methods and Applications: Cold Spring Harbor Laboratory, p. S95-S106.

Dean et al., 2001, Rapid amplification of plasmid and phage DNA using Phi29 DNA polymerase and multiply-primed rolling circle amplification: Genome Res., v. 11, p. 1095-1099.

Deng et al., 2014, Toehold-initiated Rolling Circle Amplification for Visualizing Individual MicroRNAs In Situ in Single Cells, Angewandte Chemie International Edition, 53(9):2389-2393.

Drmanac et al., 2010, Human genome sequencing using unchained base reads on self-assembling DNA nanoarrays: Science, v. 327, p. 78-81.

Duitama et al., 2011, Fosmid-based whole genome haplotyping of a HapMap trio child: evaluation of Single Individual Haplotyping techniques: Nucleic Acids Res., v. 40, p. 2041-2053.

Fan et al., 2011, Whole-genome molecular haplotyping of single cells: Nature Biotechnol., v. 29, p. 51-57.

Fire and Xu, 1995, Rolling replication of short DNA circles: Proc. Natl. Acad. Sci. USA, v. 92, p. 4641-4645.

Goldmeyer et al., 2007, Development of a Novel One-Tube Isothermal Reverse Transcription Thermophilic Helicase-Dependent Amplification Platform for Rapid RNA Detection: Journal of Molecular Diagnostics, v.9, p. 639-644.

Hatch et al., 1999, Rolling circle amplification of DNA immobilization on solid surfaces and its application to multiplex mutation detection: Genetic Analysis: Biomolecular Engineering, v. 15 p. 35-40.

He et al., 2003, Carboxyl-terminal Domain of Bacteriophage T7 Single-stranded DNA-binding Protein Modulates DNA Binding and Interaction with T7 DNA Polymerase: The Journal of Biological Chemistry, v. 278, p. 29538-29545.

Hutchison et al., 2005, Cell-free cloning using ψ29 DNA polymerase: Proc. Natl. Acad. Sci. USA, v. 102, p. 17332-17336.

International Search Report issued in corresponding PCT Application No. PCT/US2017/036129, dated Aug. 23, 2017.

Jamroze et al., 2013, The Reverse Gyrase from Pyrobaculum calidifontis, Extremely Thermophilic DNA Topoisomerase Endowed with DNA Unwinding and Annealing Activities: The Journal of Biological Chemistry, v. 289, p. 3231-3243.

Ju et al., 2006, Four-color DNA sequencing by synthesis using cleavable fluorescent nucleotide reversible terminators: Proc. Natl. Acad. Sci. USA, v. 103, p. 19635-19640.

Kaper et al., 2013, Whole-genome haplotyping by dilution, amplification, and sequencing: Proc. Natl. Acad. Sci. USA, v. 110, p. 5552-5557.

Kelleher and Champoux, 1998, Characterization of RNA Strand Displacement Synthesis by Moloney Murine Leukemia Virus Reverse Transcriptase: The Journal of Biological Chemistry, v. 273, p. 9976-9986.

Kim et al., 1992, Interactions of Gene 2.5 Protein and DNA Polymerase of Bacteriophage T7*: The Journal of Biological Chemistry, v. 267, p. 15032-15040.

Kim et al., 1992, Purification and Characterization of the Bacteriophage T7 Gene 2.5 Protein: The Journal of Biological Chemistry, v. 267, p. 15022-15031.

Kim et al., 2017, Fluorometric detection of influenza virus RNA by PCR-coupled rolling circle amplification generating G-quadruplex, Sensors and Actuators B: Chemical, 251:894-901.

Kinzler, K. W., and Vogelstein, B., 1989, Whole genome PCR: application to the identification of sequences bound by gene regulatory protein: Nucleic Acids Res., v. 17, p. 3645-3653.

Kitzman et al., 2011, Haplotype-resolved genome sequencing of a Gujarati Indian individual: Nature Biotechnol., v. 29, p. 59-63.

Kuhn et al., 2001, High Purity Preparation of a Large DNA Dumbbell: Antisense & Nucleic Acid Drug Development, v. 11, p. 149-153.

Kuleshov et al., 2014, Whole-genome haplotyping using long reads and statistical methods: Nature Biotechnology, v. 32, p. 261-266.

Langer et al., 1981, Enzymatic synthesis of biotin-labeled polynucleotides: novel nucleic acid affinity probes: Proc. Natl. Acad. Sci. USA, v. 78, p. 6633-6637.

Lee et al., 1998, Coordinated Leading and Lagging Strand DNA Synthesis on a Minicircular Template, v. 1, p. 1001-1010.

Lee et al., 2015, Fluorescent in situ sequencing (FISSEQ) of RNA for gene expression profiling in intact cells and tissues., Nature Protocols, 10(3):442-458, 2015.

LeProust et al., 2010, Synthesis of high-quality libraries of long (150mer) oligonucleotides by a novel depurination controlled process: Nucleic Acids Res., v. 38, p. 2522-2540.

Liu et al., 1996, Rolling circle DNA synthesis: Small circular oligonucleotides as efficient templates for DNA polymerases: J. Am. Chem. Soc., v. 118, p. 1587-1594.

Lo et al., 1997, Presence of fetal DNA in maternal plasma and serum: Lancet, v. 350, p. 485-487.

Long et al., 2013, An isothermal and sensitive nucleic acids assay by target sequence recycled rolling circle amplification, Biosensors and Bioelectronics, 46:102-107.

Ma et al., 2010, Direct determination of molecular haplotypes by chromosome microdissection: Nature Methods, v. 7, p. 299-301.

Melgar and Goldthwait, 1968, Deoxyribonucleic Acid Nucleases: The Effect of Metals on the Mechanism of Action of Deoxyribonuclease I*: The Journal of Biological Chemistry, v. 243, p. 4409-4416.

Metzker, 2010, Sequencing technologies—the next generation: Nature Rev. Genet., v. 11, p. 31-46.

Nilsson et al., 1994, Padlock probes: Circularizing oligonucleotides for localized DNA detection: Science, v. 265, p. 2085-2088.

Nurminsky and Hartl, 1996, Sequence scanning: A method for rapid sequence acquisition from large-fragment DNA clones: Proc. Natl. Acad. Sci. USA, v. 93, p. 1694-1698.

Nutiu et al., 2011, Direct measurment of DNA affinity landscapes on a high-throughput sequencing instrument: Nature Biotechnology, v. 29, p. 659-664.

Pavlov et al., 2002, Helix-hairpin-helix motif confer salt resistance and processivity on chimeric DNA polymerases: PNAS, v. 99, p. 13510-13515.

(56) References Cited

OTHER PUBLICATIONS

Peters et al., 2012, Accurate whole-genome sequencing and haplotyping from 10 to 20 human cells: Nature, v. 487, p. 190-195.
Pop and Salzberg, 2008, Bioinformatics challenges of new sequencing technology: Trends Genet., v. 24, p. 142-149.
Roach et al., 2011, Chromosomal haplotypes by genetic phasing of human families: Am. J. Hum. Genet., v. 89, p. 382-397.
Ruano et al., 1990, Haplotype of multiple polymorphisms resolved by enzymatic amplification of single DNA molecules: Proc. Natl. Acad. Sci. USA, v. 87, p. 6296-6300.
Saiki et al., 1985, Enzymatic amplification of beta-globin genomic sequences and restriction site analysis for diagnosis of sickle cell anemia: Science, v. 230, p. 1350-1354.
Saiki et al., 1988, Primer-directed enzymatic amplification of DNA with a thermostable DNA polymerase: Science, v. 239, p. 487-491.
Schakowski et al., 2001, A Novel Minimal-Size Vector (MIDGE) Improves Transgene Expression in Colon Carcinomas Cells and Avoids Transfection of Undesired DNA: Molecular Therapy, v. 3 (5), p. 793-800.
Seo et al., 2004, Photocleavable fluorescent nucleotides for DNA sequencing on a chip constructed by site-specific coupling chemistry: Proc. Natl. Acad. Sci. U S A, v. 101, p. 5488-5493.
Seo et al., 2005, Four-color DNA sequencing by synthesis on a chip using photocleavable fluorescent nucleotides: Proc. Natl. Acad. Sci. U S A, v. 102, p. 5926-5931.
Shabarova et al., 1991, Chemical ligation of DNA: the first non-enzymatic assembly of a biologically active gene: Nucleic Acids Research, v. 19 (15), p. 4247-4251.
Shapero et al., 2013, SNP Genotyping by Multiplexed Solid-Phase Amplification and Fluorescent Minisequencing: Genome Research, v. 11, p. 1926-1934.
Simmonds et al., 1990, Human immunodeficiency virus-infected individuals contain provirus in small numbers of peripheral mononuclear cells and at low copy numbers: J. Virol., v. 64, p. 864-872.
Sismour et al., 2004, PCR amplification of DNA containing non-standard base pairs by variants of reverse transcriptase from Human Immunodeficiency Virus-1: Nucleic Acids Res., v. 32, p. 728-735.
Stroun et al., 1989, Neoplastic characteristics of the DNA found in the plasma of cancer patients: Oncology, v. 46, p. 318-322.
Stryer and Haugland, 1967, Energy transfer: A spectroscopic ruler: Proc. Natl. Acad. Sci. USA, v. 58, p. 719-726.
Suk et al., 2011, A comprehensively molecular haplotype-resolved genome of a European individual: Genome Res., v. 21, p. 1672-1685.
Syed et al., 2009, Optimized library preparation method of next-generation sequencing: Nature Methods, Advertising Feature, p. i-ii.
Sykes et al., 1992, Quantitation of targets for PCR by use of limiting dilution: BioTechniques, v. 13, p. 444-449.
Tabor and Richardson, 1989, Selective Inactivation of the Exonuclease Activity of Bacteriophage T7 DNA Polymerase by in Vitro Mutagenesis*: The Journal of Biological Chemistry., v. 264 (11), p. 6447-6458.
Taki et al., 2003, A Direct and efficient synthesis method of dumbell-shaped linear DNA using PCR in vitro: Nucleic Acids Research Supplment No. 3., p. 191-192.
Tewhey et al., 2011, The importance of phase information for human genomics: Nature Rev. Genet., v. 12, p. 215-223.
Travers et al., 2010, A flexible and efficient template format for circular consensus sequencing and SNP detection: Nucleic Acids Research., v. 38 (15), p. 1-8.
Tyagi and Kramer, 1996, Molecular Beacons: Probes that fluoresce upon hybridization: Nature Biotechnol., v. 14, p. 303-308.
Tyagi et al., 1998, Multicolor molecular beacons for allele discrimination: Nature Biotechnol., v. 16, p. 49-53.
Vincent et al., 2004, Helicase-dependent isothermal DNA amplification: EMBO Reports., v. 5, p. 795-800.
Voskoboynik et al., 2013, The genome sequence of the colonial chordate, Botryllus schlosseri: eLife, v. 2, p. e00569.
Weber and Myers, 1997, Human whole-genome shotgun sequencing: Genome Res., v. 7, p. 401-409.
Whiting and Champoux, 1994, Strand Displacement Synthesis Capability of Moloney Murine Leukemia Virus Reverse Transcriptase: Journal of Virology., v. 68 (8), p. 4747-4758.
Xu et al., 2006, Simultaneous amplification and screening of whole plasmids using the t7 bacteriophage replisome: Nucleic Acids Research., v. 34 (13), p. 1-9.
Yamaguchi et al., 1998, MutS and MutL Activate DNA Helicase II in a Mismatch-dependent Manner: The Journal of Biological Chemistry, v. 273, p. 9197-9201.
Yang, H., Chen, X., and Wong, W. H., 2011, Completely phased genome sequencing through chromosome sorting: Proc. Natl. Acad. Sci. USA, v. 108, p. 12-17.
Zanta et al., 1999, Gene delivery: A single nuclear localization signal peptide is sufficient to carry DNA to the cell nucleus: Proc. Natl. Acad. Sci. USA, v. 96, p. 91-96.
Zhou et al., 2010, A dumbbell probe-mediated rolling circle amplification strategy for highly sensitive microRNA detection, Nucleic Acids Research, 38(15):e156-e156.

* cited by examiner

A.

B.

C.

SEQUENCE LISTING

```
<160> NUMBER OF SEQ ID NOS: 15

<210> SEQ ID NO 1
<211> LENGTH: 71
<212> TYPE: DNA
<213> ORGANISM: Artificial Sequence
<220> FEATURE:
<223> OTHER INFORMATION: miR-let-7a TRC

<400> SEQUENCE: 1
tagttcgccc tacctccaca tcctccacaa gctatccccc gaactataca acctactacc      60
tcaccgttgt a                                                          71

<210> SEQ ID NO 2
<211> LENGTH: 9
<212> TYPE: DNA
<213> ORGANISM: Artificial Sequence
<220> FEATURE:
<223> OTHER INFORMATION: miR-let-7a TRC Toehold

<400> SEQUENCE: 2 ctactacct                                                              9

<210> SEQ ID NO 3
<211> LENGTH: 13
<212> TYPE: DNA
<213> ORGANISM: Artificial Sequence
<220> FEATURE:
<223> OTHER INFORMATION: miR-let-7a TRC Switch Stem

<400> SEQUENCE: 3
cgaactatac aac                                                         13

<210> SEQ ID NO 4
<211> LENGTH: 30
<212> TYPE: DNA
<213> ORGANISM: Artificial Sequence
<220> FEATURE:
<223> OTHER INFORMATION: miR-let-7a TRC Probe(s) or other externally
      functional sequences

<400> SEQUENCE: 4
cctacctcca catcctccac aagctatccc                                       30

<210> SEQ ID NO 5
<211> LENGTH: 71
<212> TYPE: DNA
<213> ORGANISM: Artificial Sequence
<220> FEATURE:
```

<223> OTHER INFORMATION: miR-let-7g TRC

<400> SEQUENCE: 5
tagttcgccc tacctccaca tcctccacaa gctatccccc gaactataca aactactacc    60
tcaccgttgt a                                                         71

<210> SEQ ID NO 6
<211> LENGTH: 63
<212> TYPE: DNA
<213> ORGANISM: Artificial Sequence
<220> FEATURE:
<223> OTHER INFORMATION: miR-21 TRC

<400> SEQUENCE: 6
gttgacgtcc ctttccttcc actccttccc gtcaacatca gtctgataag ctactccact    60
gat                                                                  63

<210> SEQ ID NO 7
<211> LENGTH: 122
<212> TYPE: DNA
<213> ORGANISM: Artificial Sequence
<220> FEATURE:
<223> OTHER INFORMATION: multi-loop miR-21 TRC

<400> SEQUENCE: 7
gttgacgtca attaattaag ccctttcctt ccactcttaa ttaattgtct taattaattg    60
ccctttcctt ccactcaatt aattaagtcg tcaacatcag tctgataagc tactccactg   120
at                                                                  122

<210> SEQ ID NO 8
<211> LENGTH: 22
<212> TYPE: RNA
<213> ORGANISM: Artificial Sequence
<220> FEATURE:
<223> OTHER INFORMATION: miR-let-7a

<400> SEQUENCE: 8
ugagguagua gguuguauag uu                                             22

<210> SEQ ID NO 9
<211> LENGTH: 22
<212> TYPE: RNA
<213> ORGANISM: Artificial Sequence
<220> FEATURE:
<223> OTHER INFORMATION: miR-let-7g

<400> SEQUENCE: 9
ugagguagua guuguauag uu                                              22

<210> SEQ ID NO 10
<211> LENGTH: 22
<212> TYPE: DNA
<213> ORGANISM: Artificial Sequence
<220> FEATURE:
<223> OTHER INFORMATION: miR-let-7a complementary sequence

<400> SEQUENCE: 10
actccatcat ccaacatatc aa                                             22

<210> SEQ ID NO 11
<211> LENGTH: 22
<212> TYPE: DNA
<213> ORGANISM: Artificial Sequence

```
<220> FEATURE:
<223> OTHER INFORMATION: miR-let-7g complementary sequence

<400> SEQUENCE: 11
actccatcat caaacatatc aa                                              22

<210> SEQ ID NO 12
<211> LENGTH: 14
<212> TYPE: DNA
<213> ORGANISM: Artificial Sequence
<220> FEATURE:
<223> OTHER INFORMATION: Palindrome Bridge Sequence

<400> SEQUENCE: 12
aaaaaaattt tttt                                                       14

<210> SEQ ID NO 13
<211> LENGTH: 14
<212> TYPE: DNA
<213> ORGANISM: Artificial Sequence
<220> FEATURE:
<223> OTHER INFORMATION: Palindrome Bridge Sequence

<400> SEQUENCE: 13 ttttttttaaa aaaa                                                      14

<210> SEQ ID NO 14
<211> LENGTH: 11
<212> TYPE: DNA
<213> ORGANISM: Artificial Sequence
<220> FEATURE:
<223> OTHER INFORMATION: Low Complexity Bridge Sequence

<400> SEQUENCE: 14
ggcccgggcc g                                                          11

<210> SEQ ID NO 15
<211> LENGTH: 112
<212> TYPE: DNA
<213> ORGANISM: Artificial Sequence
<220> FEATURE:
<223> OTHER INFORMATION: TRC

<400> SEQUENCE: 15
cagatatcac cctacctcca catcctccac aagctatccc tgatatctgg cggcctcctc     60
ccgaactata caacctacta cctcaccgtt gtatagttcg cttcgtggcc gc            112
```

TARGET REPORTER CONSTRUCTS AND USES THEREOF

The present application claims the priority benefit of U.S. provisional application No. 62/346,334, filed Jun. 6, 2016, the entire contents of which are incorporated herein by reference.

The sequence listing that is contained in the file named "REDV.P0003US_ST25.txt", which is 4 KB (as measured in Microsoft Windows) and was created on Jun. 6, 2017, is filed herewith by electronic submission and is incorporated by reference herein.

BACKGROUND OF THE INVENTION

1. Field of the Invention

The present invention relates generally to the field of molecular biology. More particularly, it concerns compositions and methods for the detection of nucleic acids. More specifically, certain embodiments concern target reporter constructs (TRCs) for the detection of target nucleic acids using rolling circle replication or rolling circle amplification.

2. Description of Related Art

Detection of a particular nucleic acid sequence or group of sequences is an important aspect of many biological research and clinical applications, particularly for diagnoses and management of medical conditions. Methods of detecting nucleic acids, like pathogenic DNA, disease-related messenger RNAs (mRNAs) and oncogenic microRNAs (miRNAs), include reverse transcriptase polymerase chain reaction (RT-PCR), in situ microarray, and next-generation sequencing (NGS). These and other derivative methods have been developed to detect, and in some applications, quantify the presence of nucleic acid sequences of interest. However, such technologies have significant limitations and the commercially available detection platforms that leverage such methods are not ideal for diagnostic analysis.

Nucleic acid detection offers significant advantage over protein-based diagnostic methods. For example, an immunoassay is a cheap, fast, and sensitive method for screening seroconverted individuals, but this technology cannot identify those individuals with recent, acute infection—an important population in terms of disease management. More recent antigen-antibody (Ag-Ab) tests target antibodies and pathogenic components simultaneously but require blood or plasma as a starting material, and may suffer from sensitivity and specificity issues. Furthermore, the presence of antibodies yields little information regarding the real-time activity of the pathogen. The minimal correlation between viral load and antibody titer, especially in latent infection, means that the qualitative positive-negative readout of current oral point-of-care (POC) tests gives little direction for stratification and disease management. Finally, the current oral POC diagnostics "rule out" single pathogen systems necessitate the inconvenient use of an additional test for each target. New and diverse etiological agents in the form of bacterial, fungal, and viral infections present significant challenges for detection, identification and management at the POC level. Development of such technologies, particularly those using oral biospecimens, has traditionally focused on single-pathogen analysis with a qualitative answer; this "rule-out" approach has significant limitations and minimal utility for progressive disease stratification.

Cell-free nucleic acids like circulating DNA, mRNA, and non-coding RNAs (ncRNAs) are powerful indicators of human health and can be used to diagnose, stratify and treat a wide range of diseases. Importantly, many natural and pathogenic processes release nucleic acids into biofluids like blood, urine, mucus, semen, vaginal fluid, and cerebrospinal fluid where minimally-invasive samples can be obtained for testing, monitoring, and treatment.

MicroRNAs (miRNAs) are short, non-coding, single-stranded RNA molecules that mediate cell signaling pathways by regulating the translation of target mRNA transcripts. Individual miRNAs have been shown to govern many important physiological and pathogenic processes, including proliferation, cell-cycle control, apoptosis, and differentiation and are therefore important regulatory elements in transformation, tumor development, and disease progression. Importantly, a large body of evidence suggests that miRNA populations are highly dynamic, specifically with regard to neoplastic initiation and growth; the size and makeup of resident and circulating miRNA populations varies greatly depending on the malignant tissue, disease stage and subtype, and biochemical and genetic abnormalities.

Cell-free, circulating miRNAs have emerged as powerful, yet underutilized, biomarkers in translational medicine. Plasma sample collection is a minimally-invasive technique, and the stable, tumor-specific and clinically meaningful presence of cell-free miRNAs in plasma present certain advantages over traditional protein-based biomarkers that suffer from stability, sensitivity, and specificity issues. miRNAs may be present freely in the body fluids (blood, urine, saliva, mucus, etc.), bound to proteins, or present in exosomes.

Comprehensive cataloguing studies continue to define unique resident and cell-free miRNA signatures that have the ability to distinguish between normal and disease states, and to further differentiate individuals based on risk, outcome and therapeutic resistance. Particularly important are those cell-free miRNA signatures that represent early-detection biomarkers and might guide intervention strategies. Individual miRNA species and multi-miRNA signatures have been identified across a broad spectrum of conditions, including: cancer, mental illness, neurodegenerative and metabolic disorders, etc.

Development of cell-free miRNA profiling as a routine diagnostic tool is hindered by the lack of rapid and accessible strategies for easily collecting, detecting, quantifying and interpreting the exceedingly minute cell-free miRNA populations. Challenging technical issues, inter-patient variability, and the presence of multiple miRNA isoforms have further complicated widespread clinical adoption. While RT-PCR, in situ microarray, and NGS strategies have been successfully employed for discovery and initial characterization of cell-free miRNA populations, these approaches have limited utility in widespread screening and surveillance applications. For example, all current methods require relatively large amounts of input material. The low-throughput and qualitative nature of RT-PCR and microarray results can also be problematic when analyzing rare miRNA species. Library preparation, deep-sequencing, and bioinformatics analysis are technically demanding and expensive, making NGS-based methods impractical as a diagnostic platform. Therefore, few commercially available diagnostic platforms exist to address the emerging need for reliable, reproducible, cost-effective and convenient quantification of circulating miRNAs. Thus, a streamlined process to functionally profile nucleic acids like pathogenic DNA, disease-related mRNA, and cell-free miRNA populations would be a valuable addition to current disease diagnosis and treatment strategies.

SUMMARY OF THE INVENTION

In one aspect, there are provided target reporter constructs (TRCs) for detecting a target nucleic acid, the TRCs being closed, partially single-stranded nucleic acid molecules comprising: (a) a target sequence complementary to the target nucleic acid, (b) a bridge sequence forming a double-stranded portion of the TRC; and (c) an accessory sequence comprising a multifunctional probe sequence. In some embodiments, the TRCs comprise DNA, RNA, or a combination thereof. In some embodiments, the TRCs comprise standard canonical bases, modified bases, non-natural bases, or any combination of the bases thereof.

In some embodiments, the target nucleic acid is single-stranded DNA (ssDNA), double-stranded DNA (dsDNA), or ssRNA. In some embodiments, the ssRNA is microRNA (miRNA) (e.g., cell-free miRNA). In some embodiments, the ssRNA is a non-coding RNA (ncRNA). In some embodiments, the ncRNA is small interfering RNA (siRNA), piwi-interacting RNA (piRNA), miRNA, long non-coding RNA (lncRNA), or small nucleolar RNA (snoRNA).

In some embodiments, the target sequence is further defined as a toehold switch, wherein the toehold switch is a sequence capable of uniquely hybridizing to the target nucleic acid. In some embodiments, the toehold switch comprises a double-stranded switch stem and a single-stranded toehold. In some embodiments, the toehold is between 5 and 10 nucleotides in length. In some embodiments, the toehold is 7, 8, or 9 nucleotides in length. In some embodiments, the toehold switch comprises a portion of the bridge sequence. In some embodiments, the toehold switch is within 5-10 nucleotides of the bridge sequence. In some embodiments, the toehold switch is within 10-20 nucleotides of the bridge sequence. In some embodiments, the toehold switch is within 1-5 nucleotides of the bridge sequence. In some embodiments, the toehold switch and bridge sequence overlap. In some embodiments, the target sequence or toehold switch is structurally independent from the bridge sequence.

In some embodiments, the TRCs further comprise a second target sequence complementary to a second target nucleic acid.

In some embodiments, the bridge sequence comprises a palindromic sequence. In some embodiments, the bridge sequence is between the target sequence and accessory sequence. In some embodiments, the bridge sequence comprises a low complexity, repetitive sequence, such as di-, tri-, and/or tetra-nucleotide repeats.

In some embodiments, the TRCs comprise multiple, such as two or more, bridge sequences. In some embodiments, the multiple bridge sequences are identical in sequence. In some embodiments, the multiple bridge sequences comprise different sequences.

In some embodiments, the accessory sequence further comprises at least a second probe sequence. In some embodiments, the second probe sequence is distinct from the first probe sequence. In some embodiments, the first probe sequence and distinct second probe sequence form a unique multiplex probe signature. In some embodiments, the first probe sequence is specific to a first detectable moiety, such as a fluorophore, and the second probe sequence is specific to a second detectable moiety, such as a second fluorophore. In some embodiments, the unique probe signature further comprised a third, fourth, or fifth probe sequence. In some embodiments, the unique multiplex probe signature comprises a plurality of fluorophores, such as 2, 3, 4, 5, or more fluorophores.

In some embodiments, the TRCs form a loop structure under hybridization conditions that are well known in the art. In some embodiments, the TRCs form a hairpin structure or dumbbell structure. In some embodiments, the TRCs form a three- or four- looped structure. In some embodiments, the TRCs form a multi-loop structure. In some embodiments, the accessory sequence or portion thereof (e.g., probe sequence) forms the loops structure and the bridge sequence and/or the toehold switch stem forms the stem region of a dumbbell structure.

In some embodiments, the multifunctional probe sequence comprises a binding sequence. In some embodiments, the binding sequence facilitates localization of replicated TRCs to an oligonucleotide array. In some embodiments, the oligonucleotide array is used to identify and quantify the presence of target nucleic acids.

In some embodiments, the TRCs are between 50 and 100 nucleotides in length. In some embodiments, the TRCs are between 100 and 500 nucleotides in length.

In another aspect, there are provided a replicated TRC comprising concatenated monomer repeats of a TRC sequence. In some embodiments, the replicated TRC is produced from rolling circle replication and/or rolling circle amplification of a TRC, such as a TRC of the above embodiments.

In a further aspect, there is provided a replicated nanosphere comprising a replicated TRC which has undergone intramolecular hybridization between the bridge sequences within the replicated TRC.

In another aspect, intramolecular hybridization between the bridge sequences within replicated TRCs is minimal and there is no higher-order structure formed upon replication or amplification of the TRC. In some embodiments, the replicated TRC may comprise a substantially single-stranded product that can be detected (e.g., by probes or localization) or serve as a substrate for RCA reactions.

A further aspect provides a method of detecting a target nucleic acid comprising: (a) obtaining target reporter constructs (TRCs) of the embodiments, (b) contacting the TRCs with a population of target nucleic acids, wherein individual target nucleic acid molecules within the population hybridize to the complementary target sequence of the target-specific TRC, (c) performing rolling circle replication (RCR), thereby obtaining replicated TRCs, (d) introducing at least one detectable moiety, wherein the at least one detectable moiety binds the probe sequence of the replicated TRC; and (e) detecting the at least one detectable moiety, thereby detecting the target nucleic acid.

A further aspect provides a method of detecting target nucleic acid comprising: (a) obtaining target reporter constructs (TRCs) of the embodiments, (b) contacting the TRCs with a population of target nucleic acids, wherein individual target nucleic acid molecules within the population hybridize to the complementary target sequence of the target-specific TRC, (c) performing rolling circle replication (RCR), thereby obtaining replicated TRCs, (d) introducing an intercalating dye that binds the replicated TRC, and (e) detecting the detectable signal from such a bound dye, thereby detecting the target nucleic acid.

A further aspect provides a method of detecting target nucleic acid comprising: (a) obtaining target reporter constructs (TRCs) of the embodiments, (b) contacting the TRCs with a population of target nucleic acids, wherein individual target nucleic acid molecules within the population hybridize to the complementary target sequence of the target-specific TRC, (c) performing rolling circle replication (RCR) in the presence of pH sensitive dyes, thereby obtaining replicated TRCs, and (d) detecting the fluorescent or colorimetric signal from such a dye, thereby detecting the target nucleic acid.

A further aspect provides a method of detecting target nucleic acid comprising: (a) obtaining target reporter constructs (TRCs) of the embodiments, (b) contacting the TRCs with a population of target nucleic acids, wherein individual target nucleic acid molecules within the population hybridize to the complementary target sequence of the target-specific TRC, (c) performing rolling circle replication (RCR) obtaining replicated TRCs; and (d) introducing the replicated TRCs onto an organized array, and (e) detecting the replicated TRCs with intercalating dyes, fluorescent probes, or by the presence of modified nucleotides that have been incorporated into the replicated TRC, thereby detecting the target nucleic acid.

A further aspect provides a method of detecting target nucleic acid comprising: (a) obtaining target reporter constructs (TRCs) of the embodiments, (b) contacting the TRCs with a population of target nucleic acids, wherein individual target nucleic acid molecules within the population hybridize to the complementary target sequence of the target-specific TRC, (c) performing rolling circle replication (RCR) obtaining replicated TRCs; and (d) introducing the replicated TRCs onto an array which has location specific binding probes capable of hybridizing with the accessory sequence of a target-specific replicated TRC, and (e) detecting the replicated TRCs with intercalating dyes, fluorescent probes, or by the presence of modified nucleotides that have been incorporated into the replicated TRC, thereby detecting the target nucleic acid.

A further aspect provides a method of detecting target nucleic acid comprising: (a) obtaining target reporter constructs (TRCs) of the embodiments (b) contacting the TRCs with a population of target nucleic acids, wherein individual target nucleic acid molecules within the population hybridize to the complementary target sequence of the target-specific TRC, (c) performing rolling circle replication (RCR), (d) performing rolling circle amplification (RCA) of the replicated TRC with bound or free secondary primers that hybridize with the accessory sequence on the replicated TRC, and (d) detecting the replicated TRCs with intercalating dyes, fluorescent probes, or by the presence of modified nucleotides that have been incorporated into the replicated TRC, thereby detecting the target nucleic acid.

A further aspect provides a method of detecting target nucleic acid comprising: (a) obtaining target reporter constructs (TRCs) of the embodiments and attaching them to a solid or porous support, such as but not limited to a styrene bead or microscope slide (b) contacting the TRCs with a population of target nucleic acids, wherein individual target nucleic acid molecules within the population hybridize to the complementary target sequence of the target-specific TRC, (c) performing rolling circle replication (RCR), (d) performing rolling circle amplification (RCA) of the replicated TRC with bound or free secondary primers that hybridize with the accessory sequence on the replicated TRC; and (d) detecting the replicated TRCs with intercalating dyes, fluorescent probes, or by the presence of modified nucleotides that have been incorporated into the replicated TRC, thereby detecting the target nucleic acid.

In some embodiments of the above aspects, performing RCR and/or RCA comprises introducing a strand-displacing polymerase, such as a DNA polymerase or RNA polymerase. In some embodiments, the DNA polymerase is φ29, Bst, Bsu, or Klenow exonuclease.

In some embodiments, performing RCR and/or RCA comprises introducing a polymerase and accessory proteins like topoisomerases, helicases, single- and double-stranded binding proteins to facilitate strand displacement.

In some embodiments, step (b) and step (c) of the above aspects are performed in a single tube. In some embodiments, RCR is performed for 45 minutes to 90 minutes. In some embodiments, RCR is performed for 90 minutes to 48 hours.

In some embodiments, the target nucleic acids have a length greater than the length of the TRC, thereby producing a 3' overhang or a 5' overhang. In some embodiments, the method further comprises introducing an exonuclease. In some embodiments, the exonuclease is exonuclease T. In some embodiments, the exonuclease removes a 3' overhang of the target nucleic acid hybridized to the TRC, thereby presenting a 3'-OH group.

In some embodiments, obtaining replicated TRCs comprises hybridizing the bridge of at least one of the replicated TRCs within the population to the bridge of at least a second replicated TRC within the population. In some embodiments, the replicated TRCs comprise at least two replicated TRCs interconnected at the bridge. In some embodiments, a replicated TRCs comprises at least 100, 1000, 5000, or 50000 replicated TRCs interconnected at the bridge.

In some embodiments, the population of target nucleic acids comprises pathogenic nucleic acids, such as viral pathogenic nucleic acids. In some embodiments, the pathogenic nucleic acids are human immunodeficiency virus (HIV), herpes simplex virus (HSV-1), human papillomavirus (HPV), and/or Epstein-Barr virus (EBV) pathogenic nucleic acids. In some embodiments, the target sequence for the pathogenic nucleic acids comprises a length of 50-100 nucleotides.

In some embodiments, the population of target nucleic acids comprise one or more miRNAs. In some embodiments, the one or more miRNAs are tumor-associated miRNAs. In some embodiments, the tumor-associated miRNAs are selected from the group consisting of miR-let-7, miR-10b, miR-21, miR-25, miR-106b, miR-11, miR-196a, miR-210, miR-212, and miR-221.

In some embodiments, the population of target nucleic acids comprise diabetes-associated miRNAs. In some embodiments, the diabetes-associated miRNAs are selected from the group consisting of miR-146a, miR-195, miR-320, miR-29, miR-192, miR-377, miR-126, miR-203, and miR-503.

In some embodiments, the population of target nucleic acids comprise psychiatric disorders-associated miRNAs. In some embodiments, the psychiatric disorders-associated miRNAs can be selected from the group consisting of miR-128, miR-134, miR-182, miR-652, miR-132, miR-15b, miR-let-7b, miR-let-7c, miR-1202, miR-135, miR-124, miR-let-7d, miR-181a, miR-212, miR-207, miR-298, miR-26b, miR-30b, miR-29b, miR-195, miR-92, miR-30a-5p, miR-30d, miR-20b, miR-29c, miR-29a, miR-106b, miR-7, miR-24, miR-30c, miR-9-3p, let-7g, miR-181b, miR-185, miR-674, miR-532, miR-673, miR-224, miR-491, miR-93, miR-383, miR-422b, miR-708, miR-540, miR-106b, miR-140, miR-194, miR-325, miR-494, miR-362, miR-409, miR-323, miR-669a, miR-151, miR-18, miR-219, miR-596, miR-597, miR-124-1, miR-598, miR-320, miR-486, miR-219, miR-346, miR-219, miR-1202, miR-135, and miR-16.

In some embodiments, the population of target nucleic acids comprise gynecological-associated miRNAs. In some embodiments, the gynecological-associated miRNAs can be selected from the group consisting of miR-451a, miR-20a, miR-29c, miR-145, miR-200a, miR-191, miR-543, miR-141, miR-let-7b, miR-126, miR-17, miR-210, miR-202, miR-122, miR-183, miR-196a, miR-2, miR-22, miR-let-7d, miR-143, miR-195, miR-200b, miR-21, miR-940, miR-4634, miR-100, miR-10b, miR-128, miR-1, miR-215, miR-23a, miR-143, miR-195, miR-200b, miR-21, miR-940, miR-4634, miR-100, miR-10b, miR-1215, miR-23a, miR-23b, miR-26a-1, miR-135b, miR-196b, miR-503, miR-504, miR-629, miR-10a, miR-100, miR-184, miR-193a, miR-297, miR-625, miR-let-7a/f/d/g, miR-146b, miR-5p, miR-155, miR-193a, miR-297, miR-602, miR-888, miR-212, miR-662, miR-299, miR-339, miR-5p, miR-486, miR-5p, miR-768, miR-5p, miR-376a, miR-15a, miR-29a, miR-30d, miR-93*, miR-125miR-a, miR-320a, miR-7*, miR-425, miR-744, miR-146, miR-7d, miR-202, miR-7e, miR-233b, miR-523amiR-3p, miR-188, miR-10a, miR-105, miR-182, miR-372, miR-27b, miR-339, miR-3p, miR-345, miR-25, miR-302c, miR-196a2, miR-181a, miR-372, miR-645, miR-9, miR-18b, miR-19b, miR-27b, miR-30c, miR-93, miR-103, miR-132, miR-135a, miR-146a, miR-155, miR-222, miR-224, miR-320, and miR-383.

In some embodiments, the population of target nucleic acids comprise neurodegenerative disease-associated miRNAs. In some embodiments, the neurodegenerative disease-associated miRNAs can be selected from the group consisting of miR-195, miR-30d, miR-451, miR-328, miR-92a, miR-486, miR-505, miR-362, miR-151, miR-20a, miR-let-7, miR-106a*, miR-133b, miR-153, miR-184*, miR-205, miR-21*, miR-224, miR-26b, miR-301b, miR-34b/c, miR-373, miR-433, miR-64, miR-65, miR-7, miR-9, miR-106a, miR-106b, miR-107 miR-124a, miR-132, miR-146a, miR-153, miR-181c, miR-29a, miR-29b, miR-29c, miR-34a, miR-429, miR-106b, miR-124a, miR-125b, miR-146a, miR-150, miR-200a, miR-200c, miR-34b, miR-9, miR-9*, miR-206, miR-21, miR-31, miR-30c-1, miR-340, miR-208b, miR-499a, miR-4538, miR-4539, miR-208a, miR-95, miR-486, miR-1, miR-539, miR-606, miR-454, miR-124a, miR-146a*, miR-206, miR-338, miR-3p, miR-9, miR-146a, miR-106b, miR-134, miR-155, miR-935, miR-149, miR-196amiR-2, miR-203a, miR-219a, miR-1, miR-301a, miR-30a, miR-34a, miR-499a, miR-876, miR-1295a, miR-10b, miR-15a, miR-193a, miR-204, miR-21, miR-27a, miR-378a, and miR-487a.

In some embodiments, the population of target nucleic acids comprise autoimmune disease-associated miRNAs. In some embodiments, the autoimmune disease-associated miRNAs can be selected from the group consisting of miR-146a, miR-155, miR-16, miR-101, miR-21, miR-130b, miR-146a, miR-26-1, miR-125a, miR-150, miR-638, miR-198, miR-29c, miR-30b, miR-155, miR-371a, miR-422a, miR-423, miR-410, miR-663a, miR-127, miR-221, miR-222, miR-380, miR-132, miR-141, miR-17, miR-200a, miR-30a, miR-572, miR-181c, miR-196a-2, miR-22, miR-27a, miR-499a, miR-1915, miR-106a, miR-126, miR-214, miR-320a, miR-328, miR-381, miR-422a, miR-633, miR-922, miR-let-7e, miR-let-7g, miR-106b, miR-197, miR-199a-2, miR-19a, miR-19b-1, miR-210, miR-215, miR-219a-1, miR-23b, miR-29-1, miR-9-2, miR-93, miR-338, miR-372, miR-375, miR-491, miR-146b, miR-614, miR-645, miR-648, miR-99a, miR-375, miR-424, miR-20b, miR-411, miR-629, miR-146a, miR-31, miR-29b-1, miR-122, miR-155, miR-19b-1, miR-106b, miR-203a, miR-223, miR-1246, miR-106a, miR-14, miR-200b, miR-21, miR-215, miR-29a, miR-320a, miR-595, miR-1286, miR-let-7d, miR-107, miR-124-1, miR-125a, miR-125b-1, miR-126, miR-130a, miR-148a, miR-17, miR-18a, miR-196a-2, miR-19a, miR-20a, miR-200c, miR-206, miR-23a, miR-26b, miR-30c-1, miR-9-3, miR-98, miR-155, miR-586, miR-146a, miR-214, miR-29a, miR-326, miR-199a-2, miR-26b-9, miR-3, miR-374a, miR-377, miR-423, miR-100, miR-200b, miR-30a, miR-489, miR-146b, and miR-411.

In some embodiments, the population of target nucleic acids comprise cardiovascular disease-associated miRNAs. In some embodiments, the cardiovascular disease-associated miRNAs can be selected from the group consisting of miR-126, miR-210, miR-21, miR-214, miR-30d, miR-150, miR-221, miR-208a, miR-423, miR-499a, miR-208b, miR-145, miR-155, miR-22, miR-25, miR-29a, miR-29b-1, miR-340, miR-378a, miR-146a, miR-181c, miR-19b-1, miR-30a, miR-320a, miR-34a, miR-650, miR-665, miR-134, miR-137, miR-182, miR-192, miR-195, miR-199a-2, miR-199b, miR-19a, miR-223, miR-328, miR-377, miR-92b, miR-744, miR-940, miR-1292, miR-1296, miR-1825, miR-1228, miR-1293, miR-663b, miR-3148, miR-3155a, miR-3175, miR-3713, miR-4491, miR-100, miR-107, miR-10b, miR-130b, miR-142, miR-185, miR-206, miR-216a, miR-23a, miR-27b, miR-30b, miR-34b, miR-34c, miR-302c, miR-425, miR-451a, miR-146b, miR-494, miR-518e, miR-568, miR-583, miR-595 and miR-652.

In some embodiments, a single nucleic acid is the target of a TRC in a single reaction. In some embodiments, multiple nucleic acids are targeted in a single reaction with multiple, unique, target-specific TRCs in which each target nucleic acid is the target of a target-specific TRC. In some embodiments, the TRCs target between 1 and 2500 target nucleic acids. In some embodiments, the TRCs target between 1 and 100 target nucleic acids. In some embodiments, the TRCs target between 10 and 50 target nucleic acids.

In some embodiments, the TRCs are at concentrations ranging from 1 zeptomolar to 1 molar in step (b). In some embodiments, the TRCs are at individual concentrations that are dependent on the target nucleic acid.

In some embodiments, the TRCs comprise TRCs with identical target sequences. In some embodiments, the TRCs comprise subsets of TRCs with different target sequences. In some embodiments, the TRCs comprise TRCs with multiple target sequences for a viral pathogen. In some embodiments, the TRCs comprise TRCs with target sequences for more than one viral pathogen. In some embodiments, the TRCs comprise TRCs with target sequences for HIV, HSV-1, and/or EBV. In some embodiments, the TRCs comprise TRCs with target sequence for more than one miRNA (e.g., multiple miRNAs that form a miRNA signature).

In some embodiments, the method further comprises applying the replicated TRCs of step (c) to an array prior to step (d). In some embodiments, the array is a grid-patterned array. In some embodiments, the grid-patterned array is functionalized with chemical or biological moieties to direct replicated TRC positioning. In some embodiments, the chemical moieties rely on hydrophobic, hydrophilic, and/or electrostatic forces to position replicated TRCs on the grid patterned array. In some embodiments, the grid-patterned array is silanized by an aminosilane. In some embodiments, the grid patterned array is functionalized with epoxy silane. In some embodiments, the grid patterned array is functionalized with isothiocyanate. In some embodiments, the grid patterned array is functionalized with aminopropyl-derivatized or aminophenyl. In some embodiments, the grid patterned array is functionalized with mercaptosilane. In some embodiments, the grid patterned array is functionalized with aldehyde or epoxide.

In some embodiments, the detectable moiety is a fluorophore, chromophore, or radioisotope. In some embodiments, the detectable moiety is soluble or insoluble. In some embodiments, the detectable moiety is a fluorophore. In some embodiments, detecting the at least one detectable moiety comprises normalizing to a control replicated TRC. In some embodiments, step (d) comprises introducing 2, 3, or 4 distinct detectable moieties. In some embodiments, step (e) comprises detecting the 2, 3, or 4 distinct detectable moieties. In some embodiments, detecting the 2, 3, or 4 distinct detectable moieties is further defined as detecting the unique multiplex probe signature of a replicated TRC. In some embodiments, each unique multiplex probe signature comprises a plurality of fluorophores (e.g., 2, 3, 4, 5, or more). In some embodiments, detecting a multiplex probe signature comprises hybridizing a first detectable moiety, detecting the first detectable moiety, and washing of the array followed by hybridizing a second detectable moiety, and detecting the second detectable moiety, such that the combination of the first and second detectable moieties identifies a unique multiplex probe signature. In some embodiments, detecting is performed using an epifluorescence microscope.

In some embodiments, detecting is performed using fluorometric or colorimetric analysis of the RCR or RCA reaction, such as but not limited to pH sensitive dyes.

In some embodiments, detecting is performed by detecting the presence of modified nucleotides which have been incorporated into the replicated TRC. In some embodiments, these modified nucleotides include fluorescently labeled nucleotides, such as but not limited to Cy3, Cy5, fluorescein, or other fluorescent dyes described herein.

In some embodiments, replicated TRCs are applied to arrays and detected by modified nucleotides or by dye staining (e.g., Sybr).

In some embodiments, replicated TRCs are applied to arrays and bind to specific locations based on the accessory sequence which can then be used to detect and quantify the target nucleic acid(s).

In some embodiments, replicated TRCs are detected using the methods described herein using a plate reader, RT-PCR instrument, or flow cytometer.

In some embodiments, TRCs are bound to solid supports like slides or beads, and RCR and/or RCA produces replicated TRCs that can be detected using the methods described herein.

Other objects, features and advantages of the present disclosure will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent of application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The invention may be better understood by reference to one or more of these drawings in combination with the detailed description of specific embodiments presented herein.

DESCRIPTION OF ILLUSTRATIVE EMBODIMENTS

Figure 1A:
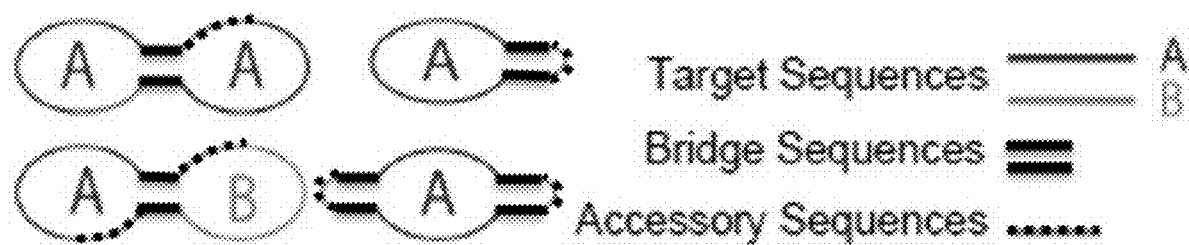
FIGS. 1A-1F: (A) Schematic of exemplary configurations for TRC construction with relative placement of functional sequences. (B) Schematic of TRC architecture and platform for use of TRCs to detect target nucleic acids. (C) Schematic of toehold switch mechanism. (D) Schematic of φ29 3' exonuclease activity removing 3' overhanging nucleotides up to the double-stranded complimentary region. Rolling circle replication is initiated, creating probable replicated TRCs. (E) Schematic of titration series of synthetic oligonucleotides used to analyze TRC metrics with fluorescent probes. Each viral pathogen has distinct fluorophore color. (F) Schematic of pathogenic nucleic acid isolation from diagnostic viral mimics in donor plasma. The sequence specific TRCs hybridize to the target nucleic acid, thereby initiating RCR and producing replicated TRCs that may be probed with pathogen-specific fluorescent probes. The digital identification of replicated TRCs occurs on a functionalized array. Each replicated TRC has a distinct fluorophore color.

The dynamic and disease-specific nature of cell-free microRNA (miRNA) populations makes them a novel class of biomarkers that have shown promise during initial studies with potentially significant clinical utility. There are, however, very few effective and accessible technologies that fully leverage the growing library of informative miRNA signatures or meet the stringent requirements necessary for widespread adoption as diagnostic platforms. Importantly, the few tests that have been approved by the FDA for this purpose rely on costly and time-consuming technologies that have limited throughput, minimal flexibility, and negligible risk assessment.

Accordingly, in some aspects, the present disclosure provides rapid, robust, cost-effective, and broadly enabling platforms for the detection of target nucleic acids. Embodiments of the present disclosure provide TRCs and methods of using these TRCs for the detection and quantitation of target nucleic acids. The nucleic acids can be pathogenic nucleic acids, such as of bacterial, fungal, and viral nucleic acids, or miRNAs, including tumor-associated miRNAs and diabetes-associated miRNAs. Other nucleic acids that can be identified include, but are not limited to, siRNA, snoRNA, lncRNA, piRNA, or full-length or fragmented oligonucleotides with known ends either naturally or artificially created (e.g., for example, enzymatically digested, CRISPR/Cas9, or use of modified nucleobases).

The TRC platform eliminates library preparation and consolidates analysis into a single, multiplex reaction resulting a reduced overall workflow and lowers technical requirements. This platform necessitates very little hands-on time or expert analysis, and the rapid and automated digital analysis renders usable data on a timescale necessary for making important health decisions.

The TRCs are rigorously designed synthetic nucleic acid (e.g., DNA) structures capable of detecting target nucleic acids, such as pathogenic nucleic acids and miRNA species, with exquisite sensitivity and specificity. TRCs can be easily synthesized and employ a number of unique elements and approaches. A TRC comprises a target sequence complementary to the target nucleic acid. In some aspects, the TRCs comprise self-complementary bridge sequences which can encourage tightly intertwined, but non-entangled DNA structures that permit detection of discrete replicated products, referred to herein as replicated TRCs. The TRC can also comprise an accessory sequence, such as a probe sequence. In some embodiments, multiple probe-hybridization sequences facilitate the decoding of replicated TRCs. In some embodiments, an accessory sequence can be used to localize replicated products by hybridization for identification and quantitation applications. Optical detection of replicated TRCs permits unparalleled multiplexibility to target multiple miRNA species in a single reaction tube. The ability to incorporate additional probe sites and more complex decoding strategies provides enormous scalability and adaptability, thus, new miRNA targets are easily incorporated. The ability to use diverse detection strategies including the incorporation of modified nucleotides in replicated TRCs and the use of intercalating dyes or colorimetric reagents makes the assay flexible for diverse applications and the ability to run the assay on many instruments (e.g., RT-PCR, plate reader, bead-based approaches, and a scanning microscope) making it accessible to a range of equipped laboratories.

Additionally, the TRC can comprise a toehold switch which forms a short duplex structure with an overhang for the target miRNA to hybridize to and initiate toehold-mediated strand displacement (TMSD), an enzyme-free, entropically-driven nucleic acid hybridization process that is more specific than Watson-Crick base-pairing and padlock-probe based approaches. The unique nature of TMSD allows for discrimination of single-nucleotide variation within miRNAs as well as detection of different miRNA isoforms.

The miRNAs function as in situ derived primers for rolling circle replication or amplification, which effectively eliminates sample preparation, inefficient library manipulation steps, and minimizes reaction biases that are present in nearly all other detection methods. This significantly reduces sample input volumes (from 400 µL to <10 µL), assay costs (from thousands to hundreds of dollars), and assay time (<two [2] hours). These factors enable replicate experiments to be run for each sample, a requirement for reliable quantitation not afforded by many previous methods. Plasma derived miRNA sequences are interrogated in a multiplex, single tube format; this eliminates the need to distribute precious samples into multiple reaction chambers. This approach further reduces the input sample size, minimizes waste, reduces bias and limits reproducibility errors that arise when rare cell-free miRNAs are divided and distributed, as in other digital quantification methods. The TRC reaction may be multiplexed, targeting multiple nucleic acids in a single reaction chamber or specific to a single target per reaction.

The toehold switches also dramatically increase the specificity of target detection with competitive strand displacement. Other commercial systems rely on simple complimentary hybridization, which is inherently vulnerable to off-target and promiscuous binding, leading to false-positives and unreliable data. The independent and universal replication of all TRC-bound miRNAs eliminates amplification bias traditionally seen in PCR-based approaches.

Accordingly, in certain embodiments, the TRCs are dumbbell-shaped and comprise three principle domains: (i) a toehold-domain capable of uniquely hybridizing to a single complimentary miRNA, (ii) bridging sequences to encourage the formation of intertwined DNA nanospheres during replication, and (iii) multiple probing sites, to facilitate multiplex fluorescent interrogation of each replicated product.

In certain embodiments, the accessory sequences can be used for probing, localization or priming for RCA.

In addition, rolling circle replication is used for isothermal amplification of the TRCs. Unlike other digital methods such as digital PCR that relies on distributing target sequences from hundreds to tens of thousands of individual wells, the TRC assay replicates all target sequences in a single tube format. The platform leverages strand-displacing properties of DNA polymerases to achieve rapid and robust replication with little temperature modulation. Persons skilled in the art will recognize strand-displacing polymerases with non-limiting examples such as φ29, Bsu, or Bst DNA polymerase. Single-molecule detection is achieved through the stochastic arrangement of replicated TRCs on high-density ordered arrays. This strategy provides an organized, quantifiable readout through high resolution fluorescent imaging of the sequentially probed replicated TRCs. TRCs custom-designed bridge sequences transform the replicated products into tightly intertwined, but non-entangled DNA structures, called replicated TRCs. Successfully replicated TRCs can then be rapidly organized on high-density patterned arrays for easy identification and quantitation.

Thus, embodiments of the present disclosure provide a novel multiplex diagnostic platform to precisely characterize pathogenic nucleic acids and cell-free miRNA signatures, specifically those miRNAs of immediate utility in diagnosis, stratification, and intervention in cancer, type I Diabetes microvascular complications, and endometriosis. The methods provided herein can provide fundamental information to positively affect disease management and patient survival.

I. Definitions

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

A "nucleic acid molecule" or "nucleic acid sequence" refers to any single-stranded or double-stranded nucleic acid molecule including standard canonical bases, hypermodified bases, non-natural bases, or any combination of the bases thereof. For example and without limitation, the nucleic acid molecule contains the four canonical DNA bases—adenine, cytosine, guanine, and thymine, and/or the four canonical RNA bases—adenine, cytosine, guanine, and uracil. Uracil can be substituted for thymine when the nucleoside contains a 2'-deoxyribose group. The nucleic acid molecule can be transformed from RNA into DNA and from DNA into RNA. For example, and without limitation, mRNA can be created into complementary DNA (cDNA) using reverse transcriptase and DNA can be created into RNA using RNA polymerase. "Analogous" forms of purines and pyrimidines are well known in the art, and include, but are not limited to aziridinylcytosine, $N^4$-acetylcytosine, 5-fluorouracil, 5-bromouracil, 5-carboxymethylaminomethyl-2-thiouracil, 5-carboxymethylaminomethyluracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyluracil, 5-methoxyaminomethyl-2-thiouracil, beta-D-mannosylqueosine, 5-methoxyuracil, 2-methylthio-$N^6$-isopentenyladenine, uracil-5-oxyacetic acid methyl ester, pseudouracil, queuosine, 2-thiocytosine, 5-methyl-2-thiouracil, 2-thiouracil, 4-thiouracil, 5-methyluracil, uracil-5-oxyacetic acid, and 2,6-diaminopurine. The nucleic acid molecule can also contain one or more hypermodified bases, for example and without limitation, 5-hydroxymethyluracil, 5-hydroxyuracil, a-putrescinylthymine, 5-hydroxymethylcytosine, 5-hydroxycytosine, 5-methylcytosine, 5-methylcytosine, 2-aminoadenine, a-carbamoylmethyladenine, $N^6$-methyladenine, inosine, xanthine, hypoxanthine, 2,6-diaminopurine, and $N^7$-methylguanine. The nucleic acid molecule can also contain one or more non-natural bases, for example and without limitation, 7-deaza-7-hydroxymethyladenine, 7-deaza-7-hydroxymethylguanine, isocytosine (isoC), 5-methylisocytosine, and isoguanine (isoG). The nucleic acid molecule containing only canonical, hypermodified, non-natural bases, or any combinations the bases thereof, can also contain, for example and without limitation where each linkage between nucleotide residues can consist of a standard phosphodiester linkage, and in addition, may contain one or more modified linkages, for example and without limitation, substitution of the non-bridging oxygen atom with a nitrogen atom (i.e., a phosphoramidate linkage, a sulfur atom (i.e., a phosphorothioate linkage), or an alkyl or aryl group (i.e., alkyl or aryl phosphonates), substitution of the bridging oxygen atom with a sulfur atom (i.e., phosphorothiolate), substitution of the phosphodiester bond with a peptide bond (i.e., peptide nucleic acid or PNA), or formation of one or more additional covalent bonds (i.e., locked nucleic acid or LNA), which has an additional bond between the 2'-oxygen and the 4'-carbon of the ribose sugar. The term "2'-deoxyribonucleic acid molecule" means the same as the term "nucleic acid molecule" with the limitation that the 2'-carbon atom of the 2'-deoxyribose group contains at least one hydrogen atom. The term "ribonucleic acid molecule" means the same as the term "nucleic acid molecule" with the limitation that the 2'-carbon atom of the ribose group contains at least one hydroxyl group.

The nucleic acids of the present disclosure may be single-stranded or double-stranded, as specified, or contain portions of both double-stranded or single-stranded sequence. The nucleic acids may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xathanine hypoxathanine, isocytosine, and isoguanine. Two nucleic acids or nucleic acid regions are "complementary" to one another if they base-pair with each other to form a double-stranded nucleic acid molecule.

The term "target nucleic acid" refers to a nucleic acid molecule on interest or nucleic acid sequence on a single-strand of nucleic acid. The target sequence may be a portion of a gene, a regulatory sequence, genomic DNA, cDNA, or RNA including mRNA and rRNA. As is outlined herein, the target nucleic acid may be a target sequence from a sample, or a secondary target such as a product of an amplification reaction. It may be of any length. In particular aspects, the target nucleic acid is a pathogenic nucleic acid or miRNA.

The term "microRNA (miRNA)" refers to single-stranded RNA molecules generally of about 21-23 nucleotides in length, but may be 16-25 nucleotides in length, which regulate gene expression. miRNAs are encoded by genes from whose DNA they are transcribed but miRNAs are not translated into protein (i.e., non-coding RNAs). The genes encoding miRNAs are much longer than the processed mature miRNA molecule; miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC. This strand is known as the guide strand and is selected by the argonaute protein, the catalytically active RNase in the RISC, on the basis of the stability of the 5' end. The remaining strand, known as the miRNA*, anti-guide or passenger strand, is degraded as a RISC substrate. Therefore the miRNA*s are derived from the same hairpin structure like the "normal" miRNAs. So if the "normal" miRNA is then later called the "mature miRNA" or "guided strand," the miRNA* is the passenger strand.

The term "closed" refers to a single or double-stranded nucleic acid molecule that lacks a free end. In some embodiments, closed nucleic acids may have an undefined shape and topology. In some embodiments, the closed nucleic acid forms a secondary structure under buffer and hybridization conditions well known in the art.

"Target report constructs (TRCs)" are referred to herein as closed, single-stranded nucleic acid molecules. In some embodiments, the TRCs are molecules used to contact and detect a target nucleic acid. In some embodiments, the TRC is circular. In some embodiments, the TRC can comprise a "dumbbell" structure meaning a structurally linear, and topologically circular in vitro replication competent or in vitro competent nucleic acid molecule that has one or more hairpin structures. When denatured or substantially denatured, dumbbell structures exist as circular, single-stranded nucleic acid molecules. The TRCs form a dumbbell or hairpin structure under conditions (e.g., pH, buffer, and temperature) known in the art.

A "hairpin structure" refers to a nucleic acid molecule whereby two or more partial sequences within the nucleic acid molecule are complementary or substantially complementary to each other resulting in the formation of a partially double-stranded region and one or more internal single-stranded regions. Hairpin structures can be formed by intramolecular base-pairing of complementary nucleotides or substantially complementary nucleotides of a given nucleic acid molecule, which can form a stem-loop structure. The stem portion of the hairpin structure is formed by hybridization of the complementary nucleotide or substantially complementary nucleotide sequences to form a double-stranded helix stretch. The loop region of the hairpin structure is the result of an unpaired stretch of nucleotide sequences. The stability of the hairpin structure is dependent on the length, buffer conditions, temperature, nucleic acid sequence composition, and degree of base-pair complementary or substantial complementary of the stem region. For example, a stretch of five complementary nucleotides may be considered more stable than a stretch of three complementary nucleotides or a stretch of complementary nucleotides that are predominately composed of guanines and cytosines may be considered more stable than a stretch of complementary nucleotides that are predominately composed of adenines and thymines (DNA) or uracils (RNA). Modified nucleotides may be substituted to alter the stability of the double-stranded stem region for these natural bases, examples of which include, but are not limited to, inosine, xanthine, hypoxanthine, 2,6-diaminopurine, $N^6$-methyladenine, 5-methylcytosine, 7-deazapurines, 5-hydroxylmethylpyrimidines. Modified nucleotides may also include numerous modified bases found in RNA species. Natural occurring stem-loop structures are predominately found in RNA species, such as transfer RNA (tRNA), pre-microRNA, ribozymes and their equivalents.

A "toehold switch" refers to a hairpin structure within the TRC which comprises a sequence fully or partially complimentary to the target nucleic acid. The toehold switch may be positioned so that the target nucleic acid binds partially within the loop and partially within stem regions. As such, the binding of a target nucleic acid may open the toehold switch, permitting RCR.

A "bridge sequence" refers to two or more sequences within a nucleic acid molecule that are self-complimentary or substantially self-complimentary. In some embodiments, in certain TRC architectures, the bridge sequences are complimentary and hybridize under certain conditions to generate a secondary structure within the molecule. In certain embodiments, in some replicated TRCs, a bridge sequence may hybridize with one or more additional bridge sequences generated following RCR or RCA.

The term "self-complimentary" as used herein refers to a nucleic acid molecule with one or more complimentary or substantially complimentary sequences contained along its length capable of intramolecular hybridization. In some embodiments, two nearly adjacent self-complimentary sequences separated by as few as one base-pair may hybridize. In some embodiments, the self-complimentary sequences may be separated by 10 to 100 base-pairs. In some embodiments, such as but not limited to certain TRC architectures, the self-complimentary sequences may be separated by an accessory sequence, target sequence or both.

The term "accessory sequence" as used herein refers to a uniquely designed component sequence of a TRC that may be used to detect the replicated TRC following RCR and/or RCA. In some embodiments, the accessory sequence may comprise a uniquely designed probe sequence to which a complimentary or substantially complimentary fluorescent probe will bind the replicated TRC, permitting detection of the target nucleic acid. In some embodiments, the accessory sequence comprises a uniquely designed sequence which can be used to localize replicated TRCs to a specific spot on an array, permitting detection of a target nucleic acid. In some embodiments, the accessory sequence may be used for a single purpose. In some embodiments, the accessory sequence may be used for multiple detection approaches, such as a fluorescent probe, localization, or a combination thereof, and is thus termed herein as a "multifunctional probe sequence."

Nucleic acid hairpin structures may be generated by deliberate design using methods of manufacturing synthetic oligonucleotides. Oligonucleotides are widely used as primers for DNA sequencing and PCR, as probes for screening and detection experiments, and as linkers or adapters for cloning purposes. Short oligonucleotides in the range of 15 to 25 nucleotides can be used directly without purification. As the stepwise yields are less than 100%, longer oligonucleotides require purification by high performance liquid chromatography or HPLC, or by preparative gel electrophoresis to remove failed oligonucleotide fractions, also known as n-1, n-2, etc. products. In certain embodiments, the nucleic acid hairpin is approximately about 100 bases.

Depending on the nature of the experiment, a given hairpin structure may be designed to contain a desired stability of the double-stranded duplex by substituting one or more hypermodified or non-natural bases and/or one or more backbone linkages as discussed herein, or including other synthetic bases such as 7-deaza-7-hydroxypurines, isoC and isoG, or their equivalents, as well as creating, for example, and without limitation, RNA-DNA, PNA-DNA, PNA-RNA, PNA-PNA, LNA-DNA, LNA-RNA, LNA-LNA, and double-stranded duplexes. Synthetically-designed hairpin structures are useful in several molecular biology techniques, for example, and without limitation, as priming sites for DNA polymerase by ligating hairpins to the ends of DNA fragments, detecting moieties as probes to identify a sequence of interest, and creating topologically circular DNA molecules from linear fragments. In certain embodiments, the 5'-ends of one or more hairpin structures will be phosphorylated, for example and without limitation, using $T_4$ polynucleotide kinase to facilitate the efficient ligation using ligating agents to the ends of one or more fragmented nucleic acid molecules.

Hairpin structures have also been used as oligonucleotide probes. DNA probes, also known as molecular beacons, are oligonucleotides designed to contain an internal probe sequence with two ends that are complementary to one another. Under appropriate conditions, the ends hybridize together forming a stem-loop structure. The probe sequence is contained within the loop portion of the molecular beacon and is unrelated to the stem arms. A fluorescent dye is attached to one end on the stem and a non-fluorescent quenching moiety or "quencher" is attached to the other end of the stem. In the stem-loop configuration, the hybridized arms keep the fluorescent dye and quencher in close proximity, resulting in quenching of the fluorescent dye signal by the well-understood process of fluorescence resonance energy transfer (FRET). When the probe sequence within the loop structure finds and hybridizes with its intended target sequence, the stem structure is broken in favor of the longer and more stable probe-target duplex. Probe hybridization results in the separation of the fluorescent dye and quencher (i.e., the close proximity is now lost), for which dye can now fluoresce when exposed to the appropriate excitation source of the detector. Molecular beacons have been used in a number of molecular biology techniques, such as RT-PCR, to discriminate allelic differences.

In certain embodiments, the hairpin structures can be created by using two or more nucleic acid molecules that are then joined to form a single hairpin structure. The two or more nucleic acid molecules can be joined together using ligating reagents to form a hairpin structure. The two or more nucleic acid molecules can also be chemically joined together using a linker to form a hairpin structure. In certain embodiments, the 5'-ends of one or more hairpin structures will be phosphorylated, for example and without limitation, using $T_4$ polynucleotide kinase to facilitate the efficient ligation using ligating agents to the ends of one or more fragmented nucleic acid molecules.

In certain embodiments, functionally important information can reside in the stem region of the hairpin structure. In certain embodiments, functionally important information can reside in the loop region of the hairpin structure. Functionally important information can include, for example and without limitation, the necessary sequences for in vitro replication, in vitro amplification, unique identification (i.e., barcodes), and detection. In certain embodiments where the functionally important information resides in the loop region of the hairpin structure, the length of the stem region can be as few as four or six base-pairs. In certain embodiments where the functionally important information resides in the stem region of the hairpin structure, the length of the loop region can be as few as one or two bases.

"Contacting" means a process whereby a substance is introduced by any manner to promote an interaction with another substance. For example, and without limitation, a dumbbell template may be contacted with one or more substantially complementary primers to promote one or more hybridizing processes to form one or more double-stranded duplex regions capable of participating in rolling circle replication or rolling circle amplification.

"Detecting a nucleic acid molecule" means using an analytical method that can determine the presence of the nucleic acid of interest or that can determine more detailed information regarding the nucleic acid sequence, alterations of a nucleic acid sequence when compared with a reference sequence, or the presence or absence of one or more copies of the nucleic acid sequence.

"End(s) of a fragmented nucleic acid molecule(s)" means one or more terminal nucleotide residues capable or to be made capable of participating in a ligation reaction. In certain embodiments, one or more nucleic acid molecules may contain functional ends capable or to be made capable of a ligation reaction to attach one or more hairpin structures to each end of the nucleic acid molecule. For example, and without limitation, the 5'-end terminal nucleotide contains a phosphate group and the 3'-end terminal nucleotide contains a hydroxyl group.

"Isolating a nucleic acid molecule" means a process whereby a nucleic acid molecule is obtained from a sample.

"Linker" means one or more divalent groups (linking members) that function as a covalently-bonded molecular bridge between two other nucleic acid molecules. A linker may contain one or more linking members and one or more types of linking members. Exemplary linking members include: —C(O)NH—, —C(O)O—, —NH—, —S—, —S(O)n-where n is 0, 1, or 2, —O—, —OP(O)(OH)O—, —OP(O)(O⁻)O—, alkanediyl, alkenediyl, alkynediyl, arenediyl, heteroarenediyl, or combinations thereof. Some linkers have pendant side chains or pendant functional groups (or both). Pendant moieties can be hydrophilicity modifiers (i.e., chemical groups that increase the water solubility properties of the linker), for example and without limitation, solubilizing groups such as —SO₃H, —SO₃⁻, CO₂H or CO₂⁻.

"Performing" means providing all necessary components, reagents, and conditions that enable a chemical or biochemical reaction to occur to obtain the desired product.

"Purifying" means removing undesired nucleic acid molecules that did not successfully ligate to form dumbbell templates for any given size range.

The term "complementary" is used herein to mean that at least 80% of the bases undergo Watson-Crick base-pairing, such as 90%, 91%, 92%, 93%, 94%, 95%, 96%, 97%, 98%, 99% or 100% of the bases undergo Watson-Crick base-pairing. For example, a complementary sequence may comprise up to 20%, such as 10% or 5%, of bases which are not Watson-Crick base-paired.

"Substantially complementary primer" means a nucleic acid molecule that forms a stable double-stranded duplex with another nucleic acid molecule, although one or more bases of the nucleic acid sequence within the duplex region do not base-pair(s) with the another nucleic acid sequence.

"Rolling circle replication (RCR)" refers to a unidirectional nucleic acid replication process that can synthesize multiple copies of circular nucleic acids, such as TRCs. In some embodiments, the target nucleic acid serves as the primer for RCR of a TRC with a complementary target sequence to generate multiple copies of the TRC in a continuous series called a "concatemer". The result of RCR from a target primed TRC is a "replicated TRC."

"Rolling circle amplification (RCA)" refers to the amplification process by which the product of initial RCR serves as a substrate and is primed one or more times by a second primer to generate multiple copies of the RCR product.

A "replicated TRC" refers to a multimeric nucleic acid molecule comprising concatenated monomer repeats of complimentary TRC sequences. In particular embodiments, a replicated TRC is produced from rolling circle replication or rolling circle amplification of a TRC. In particular embodiments, the replicated TRC undergoes intermolecular hybridization between bridge sequences, forming a "replicated nanosphere".

The term "primer" or "oligonucleotide primer" as used herein, refers to an oligonucleotide that hybridizes to the template strand of a nucleic acid and initiates synthesis of a nucleic acid strand complementary to the template strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is generally single-stranded for maximum efficiency in amplification, but may alternatively be double-stranded. If double-stranded, the primer can first be treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA or RNA synthesis. In particular embodiments, the target nucleic acid, such as a miRNA in a sample, is utilized as the primer for RCR.

The term "label" or "probe sequence" as used herein means a molecule or moiety having a property or characteristic which is capable of detection. A label or probe sequence can be directly detectable, as with, for example, radioisotopes, fluorophores, chemiluminophores, enzymes, colloidal particles, and fluorescent microparticles; or a label may be indirectly detectable, as with, for example, specific binding members. It will be understood that directly detectable labels may require additional components such as, for example, substrates, triggering reagents, and light to enable detection of the label. When indirectly detectable labels are used, they are typically used in combination with a "conjugate." A conjugate is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; and enzyme cofactors or substrates and enzymes.

"Sample" means a material obtained or isolated from a fresh or preserved biological sample or synthetically-created source that contains a nucleic acid molecule of interest. In certain embodiments, a sample is the biological material that contains the desired nucleic acid for which data or information are sought. Samples can include at least one cell, fetal cell, cell culture, tissue specimen, blood, serum, plasma, saliva, urine, tear, vaginal secretion, sweat, lymph fluid, cerebrospinal fluid, mucosa secretion, peritoneal fluid, ascites fluid, fecal matter, body exudates, umbilical cord blood, chorionic villi, amniotic fluid, embryonic tissue, multicellular embryo, lysate, extract, solution, or reaction mixture suspected of containing a target nucleic acid molecule. Samples can also include non-human sources, such as non-human primates, rodents and other mammals, plants, pathogenic species including viruses, bacteria, and fungi. In certain embodiments, the sample can also include isolations from environmental sources for the detection of human and non-human species as well as pathogenic species in blood, water, air, soil, food, and for the identification of all organisms in the sample without any prior knowledge. In certain embodiments, the sample may contain nucleic acid molecules that are degraded. Nucleic acid molecules can have nicks, breaks or modifications resulting from exposure to physical forces, such as shear forces, to harsh environments such as heat or ultraviolet light, to chemical degradation processes such as may be employed in clinical or forensic analyses, to biological degradation processes due to microorganisms or age, to purification or isolation techniques, or a combination thereof.

The basic structure of single-stranded and double-stranded nucleic acid molecules is dictated by base-pair interactions. For example, the formation of base-pairs between complementary or substantially complementary nucleotides on the two opposite strands will cause the two strands to coil around each other to form a double-helix structure. This is called intermolecular base-pairing of complementary nucleotides of two or more nucleic acid molecule strands. The term "nucleotide" is defined broadly in the present disclosure as a unit consisting of a sugar, base, and one or more phosphate groups, for which the sugar, for example, and without limitation, consists of a ribose, a modified ribose with additional chemical groups attached to one or more atoms of the ribose group, a 2'-deoxyribose, or a modified 2'-deoxyribose with additional chemical groups attached to one or more atoms of the 2'-deoxyribose group, and for which the base, for example, and without limitation, consists of a canonical base, hypermodified base, or non-natural base, as described in the nucleic acid molecule definition above. Base-pairing of complementary nucleotides or substantially complementary nucleotides can also occur on the same DNA strand molecule, called intramolecular base-pairing of complementary nucleotides or substantially complementary nucleotides.

"Subject" and "patient" refer to either a human or non-human, such as primates, mammals, and vertebrates. In particular embodiments, the subject is a human.

I. Target Reporter Constructs

Certain aspects of the present disclosure concern target reporter constructs (TRCs) for single-molecule detection of target nucleic acids, such as cell-free miRNAs and pathogenic nucleic acids. The TRCs are rigorously designed, complex nucleic acid sequence structures that comprise a target sequence which is complimentary to the target nucleic acid, bridge sequences to encourage the formation of nanospheres during replication, and probing sequences to facilitate multiplex fluorescent interrogation of each TRC-target nucleic acid replicated product as outlined in FIG. 1. In some embodiments, the probing sequence may comprise accessory sequences that permit detection by other methods. In some embodiments, a TRC can comprise a length of about 10-500 nucleotides, 50-100 nucleotides, 20-40 nucleotides, 75-150 nucleotides, or 10-50 nucleotides.

The design of the TRCs may comprise a bioinformatics approach employing the sequence alignment tool, BLAST, and the small genome alignment tool, HMMer, to generate an E-value matrix that compares selected genomes in a sliding window fashion. For example, candidate pathogen sequences that meet a heuristically determined E-value threshold are analyzed to consider optimal sequence length, $T_m$, and GC content to fully assess their "targetability," and inclusion in the TRC library.

One exemplary method for constructing a TRC comprises using single-stranded DNA oligonucleotides (e.g., Integrated DNA Technologies). Multiple TRCs are generated specific for each miRNA with the final miRNA-specific TRCs (one per miRNA target) selected after empirical testing. The 5' and 3' ends of the oligonucleotide are strategically placed within the toehold or bridge sequences; slow cooling under high-salt conditions forces the 5' and 3' ends to sit adjacent and encourages the correct intra-molecular ligation by T4 ligase (New England Biolabs). Treatment with exonucleases I and III eliminate unligated reactants. Gel electrophoresis is used to confirm the correct size and purity of the final TRC population.

In some embodiments, synthetic RNA oligonucleotides designed to mimic target and non-target miRNAs are used to establish and optimize the specificity and sensitivity of constructed TRCs. Reaction temperature, duration, buffer conditions, and reagent concentrations may be varied in an effort to define optimal conditions at each stage of the library creation process. Individual TRCs can be validated using multiple criteria. For example, a titration series of the target miRNA is used initially to gauge basic sensitivity and the ability to initiate RCR DNA synthesis. Second, mimic miRNAs with varying degrees of mismatch to the target miRNA sequence are used to quantify specificity of the individual TRC. Finally, a titration series of the target miRNA over a non-specific miRNA background is used to assess the robust ability of the TRC to function in diagnostic-like setting. All individual TRC reactions may be quantified with a molecular-beacon approach, with reactions being monitored by qRT-PCR and final products by microplate.

A. Target Sequence

A TRC of present disclosure comprises one or more target sequences which are complementary to one or more target nucleic acids. Design of the target sequences can be achieved through extensive cross-alignment between targeted and non-targeted sequences in order to minimize false positives and obtain robust, specific TRCs. In some embodiments, a single target nucleic acid may be detected by a single TRC. In some embodiments, a target nucleic acid may be detected by multiple TRCs, such as multiple replicated TRCs with the same sequence or multiple replicated TRCs with different sequences. In some embodiments, multiple target nucleic acids may be detected by a single TRC, multiple replicated TRCs with the same sequence, or multiple replicated TRCs with different sequences.

In certain embodiments, a target of interest is linear, while in other embodiments, a target is circular (e.g., plasmid DNA, mitochondrial DNA, or plastid DNA). Target nucleic acid molecules may be modified to prime TRCs for RCR or RCA. Modification methods would create a predictable end sequence on the nucleic acid target molecule by binding and cutting the nucleic acid target at a specific sequence, such as CRISPR/Cas9 or restriction enzyme digest or by creating a known end using a designed primer set. Techniques to achieve amenable targets from are performed using methods known to those skilled in the art.

In general, the pathogenic target sequences can range from a length of 10 to 500 nucleotides, 25 to 250 nucleotides, or 50 to 100 nucleotides. The miRNA target sequences may range from a length of 20 to 25 nucleotides, such as 21, 22, or 23 nucleotides.

In certain embodiments, a target nucleic acid molecule of interest is about 100 to about 1,000,000 nucleotides in length. In some embodiments, the target is about 100 to about 1000, about 1000 to about 10,000, about 10,000 to about 100,000, or about 100,000 to about 1,000,000 nucleotides in length. In some embodiments, the target is about 100, about 200, about 300, about 400, about 500, about 600, about 700, about 800, about 900, about 1,000, about 2,000, about 3,000, about 4,000, about 5,000, about 6,000, about 7,000, about 8,000, about 9000, about 10,000, about 20,000, about 30,000, about 40,000, about 50,000, about 60,000, about 70,000, about 80,000, about 90,000, about 100,000, about 200,000, about 300,000, about 400,000, about 500,000, about 600,000, about 700,000, about 800,000, about 900,000, or about 1,000,000 nucleotides in length.

In some embodiments, the target nucleic acid(s) is quantified in comparison to control miRNAs. For example, control miRNAs may include miRNA targets present in the plasma of healthy humans, such as miR-15b, miR-16, miR-24, miR-217, and/or miRNA targets present only in *C. elegans* with no sequence similarity to the human genome, such as cel-miR-39, cel-miR-54, and cel-miR-238.

1. Pathogenic Nucleic Acids

In some embodiments, the target nucleic acid is a nucleic acid that naturally occurs in an organism such as a virus, bacteria, or fungus, particularly a pathogenic virus, bacteria, or fungus. A target nucleic acid can be a single-stranded (ss) or double-stranded (ds) nucleic acid. Target nucleic acids can be, for example, DNA, RNA, or the DNA product of RNA subjected to reverse transcription. In some embodiments, a target may be a mixture (chimera) of DNA and RNA. In some embodiments, the target sequence is complementary to a region of a bacterial, viral, or fungal genome. In some aspects, the pathogenic nucleic acid is a DNA (e.g., cDNA), RNA, or DNA/RNA hybrid with a sequence complementary to a segment of the pathogen genome.

In some embodiments, the viral, bacterial or protozoological target nucleic acids, are typically selected from viral infectious diseases such as influenza, preferably influenza-A, influenza-B, influenza-C or thogotovirus, more preferably influenza-A comprising e.g., haemagglutinin subtypes H1, H2, H3, H4, H5, H6, H7, H8, H9, H10, H11, H12, H13, H14 or H15, and/or neuroamidase subtypes N1, N2, N3, N4, N5, N6, N7, N8 or N9, or preferably influenza-A subtypes H1N1, H1N2, H2N2, H2N3, H3N1, H3N2, H3N3, H5N1, H5N2, H7N7 or H9N2, etc., or any further combination, malaria, severe acute respiratory syndrome (SARS), respiratory syncytial virus infection, yellow fever, AIDS, *Lyme borreliosis*, Leishmaniasis, anthrax, meningitis, *Condyloma acuminata*, hollow warts, Dengue fever, three-day fever, Ebola virus, cold, early summer meningoencephalitis (FSME), shingles, hepatitis, herpes simplex type I, herpes simplex type II, Herpes zoster, Japanese encephalitis, Arenavirus-associated diseases (Lassa fever infection), Marburg virus, measles, foot-and-mouth disease, mononucleosis infectiosa (Pfeiffer's glandular fever), mumps, Norwalk virus infection, smallpox, polio (childhood lameness), pseudo-croup, Erythema infectiosum (fifth disease), rabies, warts, West Nile fever, chickenpox, *Cytomegalovirus* (CMV); bacterial infectious diseases such as prostate inflammation, anthrax, appendicitis, borreliosis, botulism, *Camphylobacter, Chlamydia trachomatis* (inflammation of the urethra, conjunctivitis), cholera, diphtheria, donavanosis, epiglottitis, typhus fever, gas gangrene, gonorrhoea, rabbit fever, *Heliobacter pylori*, whooping cough, climatic bubo, osteomyelitis, Legionnaire's disease, leprosy, listeriosis, pneumonia, meningitis, bacterial meningitis, anthrax, otitis media, *Mycoplasma hominis*, neonatal sepsis (Chorioamnionitis), noma, paratyphus, plague, Reiter's syndrome, Rocky Mountain spotted fever, Paratyphoid fever, Typhoid fever, scarlet fever, syphilis, tetanus, tripper, tsutsugamushi disease, tuberculosis, typhus, vaginitis (colpitis), soft chancre; and infectious diseases caused by parasites, protozoa or fungi, such as amoebiasis, bilharziosis, Chagas disease,

*Echinococcus*, fish tapeworm, fish poisoning (Ciguatera), fox tapeworm, athlete's foot, canine tapeworm, candidosis, yeast fungus spots, scabies, cutaneous Leishmaniosis, lambliasis (giardiasis), lice, malaria, onchocercosis (river blindness), fungal diseases, bovine tapeworm, schistosomiasis, porcine tapeworm, toxoplasmosis, trichomoniasis, trypanosomiasis (sleeping sickness), visceral Leishmaniosis, nappy/diaper dermatitis or miniature tapeworm.

In some aspects, the target nucleic acids are selected from Influenza A virus, influenza B virus, respiratory syncytial virus, parainfluenza virus, *Streptococcus pneumoniae, Corynebacterium diphtherias, Clostridium tetani*, Measles, Mumps, Rubella, Rabies virus, *Staphylococcus aureus, Clostridium difficile, Mycobacterium tuberculosis, Candida albicans, Haemophilus influenzae B* (HiB), poliovirus, hepatitis B virus, human papillomavirus (HPV), human immunodeficiency virus, SARS CoV, Pertussis toxin, polio virus, *Plasmodium, Staphylococcus aureus, Bordetella pertussis*, and/or polio virus VP1-4. In particular aspects, the viral pathogenic target nucleic acids are specific to human immunodeficiency virus (HIV), herpes simplex virus (HSV-1), *Influenza A* virus, West Nile Virus, and/or Epstein-Barr virus (EBV) viral pathogen nucleic acids.

The following bacteria are of particular interest, because they have been found in association with periodontal disease: *Actinobacillus* (ex. *Haemophilus*) *actinomycetemcomitans; Bacteroides gingivalis; Bacteroides intermedius Type* 1; *Bacteroides inter edius Type* 2; *Eikenella corrodens; Bacteroides forsythus; Fusobacterium nucleatum; Fusobacterium perio-donticum; Streptococcus intermedius; Wolinella recta*. The target sequences may comprise sequences capable of hybridizing to rRNA of these bacteria, especially the hypervariable regions of the 16S and 23S rRNA. Other bacterial pathogens include *Staphylococcus aureus, Staphylococcus epidermidis, Streptococcus saprophyticus, Streptococcus agalactiae, Streptococcus pyogenes, Streptococcus pneumoniae, Enterococcus faecium, Enterococcus faecalis, Mycobacterium tuberculosis, Legionella pneumophilia, Listeria monocytogene, Escherichia. coli, Klebsiella pneumoniae, Serratia marcescens, Enterobacter cloacae, Pseudomonas aeruginosa, Stenotrophomonas maltophilia, Proteus mirabilis, Haemophilus influenzae,* and *Neisseria meningitides*.

2. miRNAs

In certain embodiments, the target sequence is complementary to a target miRNA species. The target miRNA may be a tumor-associated miRNA which has elevated levels in a subject with cancer, such as the plasma of pancreatic cancer patients, or a miRNA which has decreased levels in a subject with cancer. Exemplary pancreatic tumor-associated miRNAs include, but are not limited to, miR-let-7, miR-10b, miR-21, miR-25, miR-106b, miR-11, miR-196a, miR-210, miR-212, and miR-221.

The target miRNA can be a miRNA found to be associated with cancers including, but not limited to, lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer. Further examples cancers include melanomas, malignant melanomas, colon carcinomas, lymphomas, sarcomas, blastomas, renal carcinomas, gastrointestinal tumors, gliomas, prostate tumors, bladder cancer, rectal tumors, stomach cancer, oesophageal cancer, pancreatic cancer, liver cancer, mammary carcinomas, uterine cancer, cervical cancer, acute myeloid leukemia (AML), acute lymphoid leukemia (ALL), chronic myeloid leukemia (CML), chronic lymphocytic leukaemia (CLL), leukemia, hepatomas, various virus-induced tumors such as, for example, papilloma virus-induced carcinomas (e.g., cervical carcinoma), adenocarcino-mas, herpes virus-induced tumors (e.g., Burkitt's lymphoma, EBV-induced B cell lymphoma), hepatitis B-induced tumors (hepatocell carcinomas), HTLV-1- and HTLV-2-induced lymphomas, acoustic neuroma, lung carcinomas, small-cell lung carcinomas, pharyngeal cancer, anal carcinoma, glioblastoma, rectal carcinoma, astrocytoma, brain tumors, retinoblastoma, basalioma, brain metastases, medulloblastomas, vaginal cancer, pancreatic cancer, testicular cancer, Hodgkin's syndrome, meningiomas, Schneeberger disease, hypophysis tumor, Mycosis fungoides, carcinoids, neurinoma, spinalioma, Burkitt's lymphoma, laryngeal cancer, renal cancer, thymoma, corpus carcinoma, bone cancer, non-Hodgkin's lymphomas, urethral cancer, CUP syndrome, head/neck tumors, oligodendroglioma, vulval cancer, intestinal cancer, colon carcinoma, oesophageal carcinoma, wart involvement, tumors of the small intestine, craniopharyngeomas, ovarian carcinoma, genital tumors, ovarian cancer, pancreatic carcinoma, endometrial carcinoma, liver metastases, penile cancer, tongue cancer, gall bladder cancer, leukaemia, plasmocytoma, lid tumor, and prostate cancer.

Exemplary human miRNAs associated with bladder cancer include miR-520c-3p-AS, miR-566-P, miR-33a-AS, miR-1254, miR-487a, miR-1273, miR-541, miR-487, miR-148b, and miR-634. Exemplary human miRNAs associated with prostate cancer include miR-144*, miR-148a, miR-519b-5p, miR-1324, miR-137, miR-556-5p, miR-330-3p, miR-361-5p, miR-891 b, miR-767-5p, miR-744*, miR-208b, miR-548p, miR-20a*, miR-195, miR-33b, miR-1283, miR-519c-5p, miR-497, miR-9*, miR-200a, miR-338-3p, miR-515-5p, miR-31*, miR-551b*, miR-518e*, miR-127-5p, miR-21*, miR-216a, miR-452*, miR-183*, miR-500, miR-1826, miR-625*, miR-513b, miR-526a, miR-33a, miR-1243, miR-517*, miR-541, miR-217, miR-621, miR-518d-5p, miR-873, miR-103-as, miR-450b-5p, miR-545, miR-1251, miR-885-5p, miR-922, miR-628-5p, miR-548f, miR-802, miR-25, miR-423-3p, miR-522*, miR-519a*, miR-455-3p, miR-1245, miR-362-5p, miR-1184, miR-191, miR-487a, miR-216b, miR-525-5p, miR-509-3-5p, and miR-27a*, miR-488*, miR-1226, miR-646, miR-527, miR-635, miR-1825, let-7i*. Exemplary miRNAs associated with breast cancer include miR-1, miR-92a, miR-133a and miR-133b.

Exemplary human miRNAs associated with ovarian cancer include miR-1248, miR-342-3p, miR-133b, miR-605, miR-450b-3p, miR-520a-3p, miR-23b*, miR-423-5p, miR-219-1-3p, miR-454* miR-26b*, miR-1259, miR-655, miR-302c, miR-383, miR-150, miR-412, miR-548i, let-7e*, miR-324-3p, miR-335*, miR-320a, miR-320d, miR-409-3p, miR-590-3p, miR-545*, miR-889, miR-1224-3p, miR-148a*, miR-9, miR-518f, miR-488, miR-182, miR-10a*, miR-19b, miR-15a, miR-1289, miR-500, miR-1281, miR-942, miR-877*, let-7f-1*, miR-651, miR-610, miR-664, miR-613, miR-483-3p, miR-320c, miR-720, miR-299-5p, miR-579, miR-636, miR-197, miR-668, miR-494, miR-1262, miR-578, miR-708*, miR-329, miR-941, miR-155, miR-26a-1*, miR-1246, miR-892b, miR-146a, miR-337-3p, miR-130a*, let-7b, miR-744*, miR-140-3p, miR-573, miR-378, miR-1237, and miR-363*.

Exemplary human miRNAs associated with lung cancer include miR-361-5p, miR-23b, miR-126, miR-527, miR-29a, let-7i, miR-19a, miR-28-5p, miR-185*, miR-23a, miR-1914*, miR-29c, miR-505*, let-7d, miR-378, miR-29b, miR-604, miR-29b, let-7b, miR-299-3p, miR-423-3p, miR- 18a*, miR-1909, let-7c, miR-15a, miR-425, miR-93*, miR-665, miR-30e, miR-339-3p, miR-1307, miR-625*, miR-193a-5p, miR-130b, miR-17*, miR-574-5p, and miR-324-3.

In further aspects, the target miRNA may be a diabetes-associated miRNA which is associated with diabetes, particular type I Diabetes. Diabetes-associated miRNAs include those miRNAs which are detected at altered levels in individuals with type I Diabetes and associated complications. For example, miRNAs associated with diabetic retinopathy (e.g., miR146a, miR-195, and miR-320), diabetic nephropathy (e.g., miR29, miR192, and miR-377), or diabetic neuropathy (e.g., miR-126, miR-203, and miR-503) can be the target miRNA. Further target miRNAs include AngiomiRs (e.g., miR-93, miR-200, and miR-661) with implications in diabetes as reliable indicators of global microvascular changes.

miRNAs which can be used as control miRNAs for normalization can include miRNAs present in the plasma of healthy humans (e.g., miR-15b, miR-16, miR-24, and miR-217), and/or miRNAs present in a genome with no sequence similarity to the human genome, such as *C. elegans* (e.g., cel-miR-39, cel-miR-54, and cel-miR-238). Control miRNAs can also comprise artificially-derived sequences such as an 'alien' sequence that does not sufficiently align with any known sequences in public genetic databases.

The target miRNA may be a psychiatric disorders-associated miRNA. Psychiatric disorder-associated miRNAs include those miRNAs which are detected at altered levels in individuals with psychiatric disorders and associated complications. For example, miRNAs associated with bipolar disorder (e.g., miR-652, miR-132, miR-15b), major depression disorder (e.g., miR-let-7b, miR-let-7c, miR-1202, and miR-135), substance abuse (e.g., miR-124, miR-let-7d, miR-181a, and miR-212), schizophrenia (e.g., miR-207, miR-298, miR-26b, miR-30b, miR-29b, miR-195, miR-92, miR-30a-5p, miR-30d, miR-20b, miR-29c, miR-29a, miR-212, 106b, miR-7, miR-24, miR-30c, miR-9-3p, miR-let-7g, miR-181b, miR-185, miR-134, miR-674, miR-532, miR-673, miR-224, miR-491, miR-93, miR-383, miR-212, miR-422b, miR-708, miR-540, miR-106b, miR-140, miR-194, miR-325, miR-494, miR-362, miR-409, miR-323, miR-669a, miR-151, miR-18, miR-219, miR-596, miR-597, miR-124-1, miR-598, miR-383, miR-320, miR-486, miR-219, miR-346, and miR-219), and response to anti-depressants (e.g., miR-1202, miR-135, and miR-16) can be the target miRNA.

The target miRNA may be a gynecological disease-associated miRNA. Gynecological disease-associated miRNAs include those miRNAs which are detected at altered levels in individuals with gynecological disorders and associated complications. For example, miRNAs associated with endometriosis (e.g., miR-451a, miR-20a, miR-29c, miR-145, miR-200a, miR-191, miR-543, miR-141, miR-let-7b, miR-126, miR-17, miR-210, miR-202, miR-122, miR-183, miR-196a, miR-2, miR-22, miR-let-7d, miR-143, miR-195, miR-200b, miR-21, miR-940, miR-4634, miR-100, miR-10b, miR-128, miR-1, miR-215, miR-23a, miR-23b, miR-26a-1, miR-135b, miR-196b, miR-503, miR-504, and miR-629), infertility (e.g., miR-10a, miR-100, miR-184, miR-193a, miR-5p, miR-297, miR-602, miR-625, miR-let-7a/f/d/g, miR-146b, miR-5p, miR-155, miR-182, miR-193a, miR-5p, miR-297, miR-625, miR-602, miR-888, miR-212, miR-662, miR-299-5p, miR-339, miR-5p, miR-20a, miR-486, miR-5p, miR-141, miR-768, miR-5p, miR-376a, miR-15a, miR-21, miR-29a, miR-30d, miR-93*, miR-125-a, miR-320a, miR-7*, miR-425, miR-744, miR-146, miR-7d, miR-202, miR-7e, miR-233b, miR-523a-3p, miR-15a, miR-188, miR-10a, miR-105, miR-182, miR-372, miR-141, miR-27b, miR-339, miR-3p, miR-345, miR-191, miR-25, miR-302c, miR-196a2, miR-181a, miR-191, miR-372, and miR-645), and polycystic ovarian syndrome (e.g., miR-9, miR-18b, miR-19b, miR-21, miR-27b, miR-30c, miR-93, miR-103, miR-132, miR-135a, miR-146a, miR-155, miR-222, miR-224, miR-320, and miR-383) can be the target miRNA.

The target miRNA may be a neurodegenerative disease-associated miRNA. Neurodegenerative disease-associated miRNAs include those miRNAs which are detected at altered levels in individuals with neurodegenerative disease and associated complications. For example, miRNAs associated with traumatic brain injury (e.g., miR-195, miR-30d, miR-451, miR-328, miR-92a, miR-486, miR-505, miR-362, miR-151, and miR-20a), Parkinson's disease (e.g., miR-let-7, miR-106a*, miR-133b, miR-153, miR-184*, miR-205, miR-21*, miR-224, miR-26b, miR-301b, miR-34b/c, miR-373, miR-433, miR-64, miR-65, miR-7, and miR-9), Tourette's Syndrome (e.g., miR-429 and miR-106b), Huntington's Disease (e.g., miR-124a, miR-125b, miR-132, miR-146a, miR-150, miR-200a, miR-200c, miR-34b, miR-9, and miR-9*), Duchenne Muscular Dystrophy (e.g., miR-206, miR-21, miR-31, miR-30c-1, miR-340, miR-208b, miR-499a, miR-4538, miR-4539, miR-208a, miR-95, miR-486-1, miR-539, miR-606, and miR-454), Amyotrophic Lateral Sclerosis (e.g., miR-124a, miR-146a*, miR-206, miR-338, miR-3p, and miR-9), Epilepsy (e.g., miR-146a, miR-132, miR-106b, miR-134, miR-155, miR-935, miR-149, miR-196a-2, miR-203a, miR-219a, miR-1, miR-301a, miR-30a, miR-34a, miR-499a, miR-876, miR-1295a, miR-10b, miR-15a, miR-193a, miR-204, miR-21, miR-27a, miR-378a, and miR-487a) and Alzheimer's disease (e.g., miR-106a, miR-106b, miR-107 miR-124a, miR-132, miR-146a, miR-153, miR-181c, miR-29a, miR-29b, miR-29c, and miR-34a) can be the target miRNA.

The target miRNA may be an autoimmune disease-associated miRNA. Autoimmune disease-associated miRNAs include those miRNAs which are detected at altered levels in individuals with autoimmune disease and associated complications. For example, miRNAs associated with rheumatoid arthritis (e.g., miR-146a, miR-155, miR-132 and miR-16), Lupus (e.g., miR-101, miR-21, miR-130b, miR-146a, miR-26a-1, miR-125a, miR-150, miR-638, miR-198, miR-29c, miR-30b, miR-155, miR-371a, miR-422a, miR-423, miR-410, miR-663a, miR-127, miR-221, miR-222 and miR-380), Multiple sclerosis (e.g., miR-429 and miR-106b), Huntington's Disease (e.g., miR-124a, miR-125b, miR-132, miR-146a, miR-150, miR-132, miR-141, miR-17, miR-200a, miR-30a, 572, miR-181c, miR-196a-2, miR-22, miR-27a, miR-499a, miR-1915, miR-106a, 126, miR-214, miR-320a, miR-328, miR-381, miR-422a, miR-20b, miR-633, miR-922, miR-let-7e, miR-let-7g, miR-106b, miR-191, miR-197, miR-199a-2, 19a, miR-19b-1, miR-210, miR-215, miR-219a-1. miR-23b, miR-29b-1, miR-9-2, miR-93, miR-338, miR-372, miR-375, miR-491, miR-146b, miR-614, miR-645 and miR-648), Crohn's Disease (e.g., miR-99a, miR-375, miR-424, miR-20b, miR-411, miR-629, miR-146a, miR-31, miR-29b-1, miR-122, miR-155, miR-19b-1, miR-106b, miR-203a, miR-223, 1246, miR-let-7e, miR-106a, miR-141, miR-191, miR-200b, miR-21, miR-215, miR-29a, miR-320a, miR-595, miR-1286, miR-let-7d, miR-107, miR-124-1, miR-125a, miR-125b-1, miR-126, miR-130a, miR-148a, miR-17, miR-18a, miR-196a-2, miR-19a, miR-20a, miR-200a, miR-200c, miR-206, miR-23a, miR-26b, miR-29c, miR-30-1, miR-9-3, miR-98), and Graft vs Host Disease (e.g., miR-155, miR-586, miR-146a, miR-214, miR-29a, miR-326, miR-199a-2, miR-26b-9, miR-3, miR- 374a, miR-377, miR-423, miR-100, miR-200b, miR-30a, miR-489, miR-146b and miR-411) can be the target miRNA.

The target miRNA may be a cardiovascular disease-associated miRNA. Cardiovascular disease-associated miRNAs include those miRNAs which are detected at altered levels in individuals with heart disease, heart failure, and associated complications. For example, miRNAs associated with heart failure (e.g., miR-126, miR-210, miR-21, miR-214, miR-30d, miR-150, miR-221, miR-208a, miR-423, miR-499a, miR-208b, miR-145, miR-155, miR-22, miR-25, miR-29a, miR-378a, miR-146a, miR-181c, miR-19b-1, miR-30a, miR-320a, miR-34a, miR-650, miR-665, miR-134, miR-137, miR-182, miR-192, miR-195, miR-199a-2, miR-199b, miR-19a, miR-223, miR-328, miR-377, miR-92b, miR-744, miR-940, miR-1292, miR-1296, miR-1825, miR-1228, miR-1293, miR-663b, miR-3148, miR-3155a, miR-3175, miR-3713, miR-4491, miR-100, miR-107, miR-10b, miR-130b, miR-142, miR-185, miR-206, miR-216a, miR-23a, miR-27b, miR-30b, miR-34b, miR-34c, miR-302c, miR-425, miR-451a, miR-146b, miR-494, miR-518e, miR-568, miR-583, miR-595, miR-29b-1, and miR-340) and heart disease (e.g., miR-21, miR-499a, miR-155, miR-214, miR-126, miR-196a-2, miR-208a, miR-98, miR-221, miR-146a, miR-154, miR-184, miR-181a-1, miR-27b, miR-34b, miR-208b, miR-1265, miR-150, miR-22, miR-29a, miR-34a, miR-10a, miR-145, miR-210, miR-222, miR-378a, miR-421, miR-935, miR-1263, miR-let-7b, miR-let-7c, miR-100, miR-10b, miR-134, miR-142, miR-149, miR-17, miR-186, miR-199b, miR-215, miR-223, miR-23a, miR-24-2, miR-25, miR-26b, miR-29b-1, miR-302a, miR-31, miR-34c, miR-9-3, miR-96, miR-99a, miR-328, miR-377, miR-423, miR-146b, miR-486-1, miR-570 and miR-650) can be the target miRNA.

3. Additional Targets

TRCs can be used to target other nucleic acids, like ssDNA, dsDNA, or ssRNA. In some embodiments, the ssRNA is a ncRNA. In some embodiments, the ncRNA is siRNA, piRNA, miRNA, lncRNA, or snoRNA.

B. Toehold Switch

A high degree of specificity and sensitivity are essential to the TRCs functionality. Toehold switches can be used to achieve single miRNA detection over a wide dynamic range and with exquisite orthogonality. Toehold switches are highly modified versions of bacterial post-transcriptional riboregulators, which govern translation with repressive mRNA secondary structure (FIG. 1B). Toehold-mediated strand displacement (TMSD) is an enzyme-free entropically-driven process that fosters invasion of a nucleic acid duplex (i.e., the transducer) by a single-stranded nucleic acid (i.e., the trigger) based on the invading strands ability to gain a "toehold" at its 3' or 5'-end. The complete displacement by the trigger may allow a stalled reaction to proceed. Toehold switches display higher hybridization specificity than standard Watson-Crick and padlock based approaches and display greater single-nucleotide discrimination.

The toehold switch comprises a first strand with a sequence complementary to the target nucleic acid sequence and a second strand which forms a double-stranded region or stem switch with part of the first strand. The single-stranded region or toehold of the first strand may comprise a length of 4-20 nucleotides, such as 5, 6, 7, 8, 9, or 10 nucleotides in length. The double-stranded region may comprise a length of 5-50 nucleotides, particularly 10-20 nucleotides. The toehold region may be positioned at the 3'end or the 5' end of the switch stem (e.g., is an extension of the 3'end or 5'end of the complement which is part of the switch stem). In some embodiments, a toehold region is 4, 5, 6, 7, 8, 9, 10, 11, 12, 13, 14, 15, 16, 17, 18, 19, or 20 nucleotides in length. In some embodiments, the toehold region is greater than 20 nucleotides in length, including for example less than or about 25, 30, 35, 40, 45, 50, 55, 60, 65, 70, 75, 80, 85, 90, 95, 100 or more nucleotides.

In some embodiments, the TRCs incorporate toehold switches as short duplex structures and utilize individual miRNAs as triggers. The toehold forms the double-stranded region under appropriate "hybridization conditions," which include temperature, factors such as salts, buffer and pH, detergents, and organic solvents. Finely tuned manipulation of the DNA duplex structure with regard to kinetic and thermodynamic properties alter individual toehold hybridization specificity, effectively creating ON/OFF circuits that may only be triggered by a single transacting. miRNA species. In some aspects, the 5'-end of a specific miRNA can bind to the complimentary single-strand sequence adjacent to the toehold switch and through TMSD, open the duplex. The hybridization reaction, termed toehold-mediated strand displacement (TMSD), is initiated with the 5'-end binding of the miRNA to a short single-stranded overhang, adjacent to the duplex region of the structure. Hybridization proceeds with miRNA invasion, internal displacement, and duplex uncoupling. An exceptionally high degree of specificity is discerned at this step due to the thermodynamically favorable, complete invasion of complimentary miRNA over the unfavorable transient partial-binding of mismatched, non-targeted miRNA species. The fully hybridized miRNA is effectively an in situ derived primer that initiates rolling circle replication (RCR) of the TRC via highly-processive, strand-displacing RNA-primed DNA polymerases such as φ29.

Toehold switches dramatically increase the specificity of target detection with competitive stand displacement. All other commercial systems rely on simple complimentary hybridization, which is inherently vulnerable to off-target and promiscuous binding, leading to false-positives and unreliable data. Embodiments of the present disclosure also extend the application of toehold switches by capitalizing on the exceptional stability of RNA/DNA duplexes and reversing the conventional binding direction in order to initiate DNA, instead of protein, synthesis.

In some aspects, the target nucleic acid is a miRNA of the let-7 family such as miR-let-7a and miR-let-7g. Accordingly, in some aspects the toehold switch sequence is complementary to miR-let-7a (UGAGGUAGUAGGUU-GUAUAGUU (SEQ ID NO: 8)) or miR-let-7g (UGAGGU-AGUAGUUUGUAUAGUU (SEQ ID NO: 9)); which differ by a single nucleotide at the 12th position (G>U, bolded and underlined), and comprises the sequence ACTCCATCATC-CAACATATCAA (SEQ ID NO: 10) or ACTCCATCAT-CAAACATATCAA (SEQ ID NO:11).

C. Bridge Sequence

In some embodiments, TRCs can contain one or more short, self-complementary sequences, referred to herein as bridge sequences. The inclusion of interspersed, self-complementary bridge sequences can drive intra-molecular hybridization and encourage the formation of the tightly intertwined, but non-entangled nucleic acid sequence structures. Therefore, the product of an individual TRC RCR reaction, referred to herein as a "replicated TRC," is a singular nucleic acid sequence structure composed of highly replicated concatenated repeats of the TRC compliment. The bridge sequences may be incorporated in a variety of TRC configurations. In some aspects, the bridge structure is within 1 to 200 nucleotides, such as 10 to 100 nucleotides, of the toehold switch. In some aspects, the bridge structure overlaps with the toehold switch.

The bridge sequence may comprise a secondary structure sequence for the formation of nanospheres from replicated TRCs. This secondary structure sequence or "stabilizing sequence" is a nucleic acid sequence that facilitates nanosphere formation and/or stability. For example, palindromic sequences within the bridge sequence can result in hybridization (e.g., intramolecular interactions) between replicated TRCs resulting in a three dimensional structure of the replicated TRC. These palindromic sequence units can be 5, 6, 7, 8, 9, 10 or more nucleotides in length and of various sequences, such as sequences chosen to provide a specific melting temperature. For example, a palindrome AAAAAAATTTTTT (SEQ ID NO: 12) will provide a 14 bases dsDNA hybrid between neighboring any two unit replicas in the form of: AAAAAAATTTTTT (SEQ ID NO: 12) and TTTTTTTAAAAAAA (SEQ ID NO: 13).

The bridge sequence may comprise a low complexity, repetitive sequence. Exemplary low complexity, repetitive sequences may include, but are not limited to, di-, tri-, and/or tetra-nucleotide repeats (e.g., GGCCCGGGCCG (SEQ ID NO: 14).

D. Accessory Sequence

In further embodiments, the TRC may comprise accessory sequence(s). Accessory sequences may include secondary structure sequences, sequences complementary to capture probe sequences (e.g., for attachment to surfaces), tagging sequences, sequences for attachment/hybridization of label probes, recognition sites for nucleases, such as nicking enzyme, and/or restrictions endonucleases. In some aspects, the accessory sequence of portion thereof (e.g., probe sequence) forms a loop, such as within a hairpin or dumbbell structure in which the bridge and/or switch stem regions form the stem portion of the structure.

In certain embodiments, functionally important information can reside in the accessory sequence(s) of the TRC. Functionally important information can include, for example and without limitation, the necessary sequences for in vitro replication, unique identification (i.e., barcodes), and detection. A capture probe recognition sequence may be utilized to immobilize the TRC and/or replication nanosphere on a substrate, such as an array. An accessory sequence can be used to localize replicated products by hybridization for identification and quantitation applications. Backbone TRC components are derived from unalignable alien sequences; such sequences have been designed by the NIST External RNA Controls Consortium to have zero complementarity within known genomes.

Additional functionality from accessory sequences could include elements to uniquely digest certain parts of the TRC, TRC-Target hybrid, or TRC product for analysis before or after replication. For example, the following sequence has an EcoRV digestion site incorporated so that the product can be digested into smaller fragments: CAGATATCACcctac ctccacatcctccacaagctatccctGATATCtggcggccTCCTCC CGAACTATACAACCTACTACCTCACC GTTGTATAGTTCGCTTCGTGGCCGC (SEQ ID NO: 15).

Additionally, the TRCs could have uracil nucleotides incorporated and could be substrates for uracil-specific digestion. Accessory sequences in the replicated TRC could be used to localize replicated TRCs, allowing for detection and analysis without probing but merely buy identifying where products bind on a microarray. Sequences could be used to alter the product structure, potentially allowing spatially unique products for alternative analysis methods.

Additionally, TRCs could have biotin-tagged nucleotides incorporated that could be used as anchoring TRCs to a solid support or for isolation of TRCs following construction.

In some embodiments, the accessory sequence comprises one or more probing sequences, such as fluorescent probe binding sites. Label probes will hybridize to the label probe binding sequence and comprise at least one detectable label. Multiple probing sequences can facilitate coded fluorescent-based digital interrogation and identification of the TRC reaction products. Each TRC may contain a unique set (e.g., combination and order) of probe sequences. Sequential hybridization with pools of multi-state, labeled-probes to the arrayed replicated TRCs followed by imaging can permit decoding, identification, and quantification of the miRNAs present in the sample.

The term "probe" or "probe sequence" is used in a broad sense of oligonucleotides used in direct hybridization, or as in ligation of two probes, or as in probe with an anchor, or as in a probe with an anchor probe. In some aspects, the probe sequence comprises 5-30 bases, particularly 10-20 bases.

In certain embodiments, the accessory sequence comprises hybridizing sites for binding oligonucleotide probe(s). Certain DNA probes, also known as molecular beacons, are oligonucleotides designed to contain an internal probe sequence with two ends that are complementary to one another. Under appropriate conditions, the ends hybridize together forming a stem-loop structure. The probe sequence is contained within the loop portion of the molecular beacon and is unrelated to the stem arms. A fluorescent dye is attached to one end on the stem and a non-fluorescent quenching moiety or "quencher" is attached to the other end of the stem. In the stem-loop configuration, the hybridized arms keep the fluorescent dye and quencher in close proximity, resulting in quenching of the fluorescent dye signal by the well-understood process of fluorescence resonance energy transfer (FRET). When the probe sequence within the loop structure finds and hybridizes with its intended target sequence, the stem structure is broken in favor of the longer and more stable probe-target duplex. Probe hybridization results in the separation of the fluorescent dye and quencher (e.g., the close proximity is now lost), for which dye can now fluoresce when exposed to the appropriate excitation source of the detector. Molecular beacons have been used in a number of molecular biology techniques, such as real-time PCR, to discriminate allelic differences.

The oligonucleotide probes of the present disclosure can be labeled in a variety of ways, including the direct or indirect attachment of radioactive moieties, fluorescent moieties, calorimetric moieties, and chemiluminescent moieties. Methodologies for labeling DNA and constructing DNA adaptors as well as constructing oligonucleotide probes of the present disclosure are known in the art. Many more particular methodologies applicable to the present methods include linking agents, such as 2-substituted-3-protected-1, 3,2-oxazaphosphacycloalkanes and their phosphoramidite precursors, alkynylamino-nucleotides, nucleotide triphosphate having a linking group carried on an exocyclic functional group of the base, nucleotide reactive phosphorus derivatives, and fluorescent semiconductor nanocrystals (i.e., quantum dots).

In one aspect, one or more fluorescent dyes are used as labels for the oligonucleotide probes, such as, but not limited to, 4,7-dichlorofluoresceins (e.g., 1',2',7',8'-dibenzo-4,7-dichlorofluoresceins), spectrally resolvable rhodamine dyes (e.g., tetramethylrhodamine, rhodamine X, rhodamine 110, and rhodamine 6G); 4,7-dichlororhodamine dyes, ether-substituted fluorescein dyes (e.g., 2,7-di(aliphatic chalcogen ether substituted) or 4,5-di(aliphatic chalcogen ether substituted)-9-substituted-6-hydroxy-3H-xanthen-3-one), energy transfer dyes, and xanthene dyes (e.g., derivatives of sulfonefluorescein, naphthosulfone fluorescein, fluorescein and naphthofluorescein).

Labeling can also be carried out with quantum dots. The quantum dot may be a coated nanocrystal capable of light emission includes a substantially monodisperse core selected from the group consisting of CdX, where X=S, Se, or Te; and an overcoating of ZnY, where Y=S, Se, and mixtures thereof uniformly deposited thereon, said coated core characterized in that when irradiated the particles emit light in a narrow spectral range of no greater than about 40 nm at full width half max (FWHM). A nanocrystallite with a diameter of less than 150 Å may be used, such as a sphere, rod, disk, or other shape. The nanocrystallite can include a core of a semiconductor material. The core can have an overcoating on a surface of the core. The overcoating can be a semiconductor material having a composition different from the composition of the core. Semiconducting nanocrystallites can photoluminesce and can have high emission quantum efficiencies. The nanocrystallite can include a core having the formula MX, where M is cadmium, zinc, magnesium, mercury, aluminum, gallium, indium, thallium, or mixtures thereof, and X is oxygen, sulfur, selenium, tellurium, nitrogen, phosphorus, arsenic, antimony, or mixtures thereof. In some embodiments, the nanocrystal may be a luminescent semiconductor nanocrystal compound comprising (1) a semiconductor nanocrystal capable of luminescence and/or absorption and/or scattering or diffraction when excited by an electromagnetic radiation source (of broad or narrow bandwidth) or a particle beam, and capable of exhibiting a detectable change in absorption and/or of emitting radiation in a narrow wavelength band and/or scattering or diffracting when excited; and (2) a linking agent having a first portion linked to the semiconductor nanocrystal, and a second portion capable of linking to an affinity molecule. In some embodiments, the nanocrystal is a water-soluble nanocrystal that emits energy over a narrow range of wavelengths. In some embodiments, the nanocrystal is a semiconductor nanocrystal compound capable of linking to either one or more second linking agents or to one or more affinity molecules, and capable of providing a detectable signal in response to exposure to energy.

As used herein, the term "fluorescent signal generating moiety" means a signaling means which conveys information through the fluorescent absorption and/or emission properties of one or more molecules. Such fluorescent properties include fluorescence intensity, fluorescence life time, emission spectrum characteristics, and energy transfer. Commercially available fluorescent nucleotide analogues readily incorporated into the labeling oligonucleotides or directly into the replicated TRC include, for example, Cy3-dCTP, Cy3-dUTP, Cy5-dCTP, Cy5-dUTP (Amersham Biosciences, Piscataway, N.J., USA), fluorescein-12-dUTP, tetramethylrhodamine-6-dUTP, Texas Red®-5-dUTP, Cascade Blue®-7-dUTP, BODIPY® FL-14-dUTP, BODIPY°R-14-dUTP, BODIPY®TR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, Alexa Fluor® 546-14-UTP (Molecular Probes, Inc. Eugene, Oreg., USA). Other fluorophores available for post-synthetic attachment include, inter alia, Alexa Fluor® 350, Alexa Fluor® 532, Alexa Fluor® 546, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3.5, Cy5.5, and Cy7 (Amersham Biosciences, Piscataway, N.J. USA, and others). FRET tandem fluorophores may also be used, such as PerCP-Cy5.5, PE-Cy5, PE-Cy5.5, PE-Cy7, PE-Texas Red, and APC-Cy7; also, PE-Alexa dyes (610, 647, 680) and APC-Alexa dyes. Biotin, or a derivative thereof, may also be used as a label on a detection oligonucleotide, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into a detection oligonucleotide and subsequently coupled to an N-hydroxy succinimide (NETS) derivitized fluorescent dye, such as those listed supra.

In general, any member of a conjugate pair may be incorporated into a detection oligonucleotide provided that a detectably labeled conjugate partner can be bound to permit detection. As used herein, the term antibody refers to an antibody molecule of any class, or any subfragment thereof, such as a Fab. Other suitable labels for detection oligonucleotides may include fluorescein (FAM), digoxigenin, dinitrophenol (DNP), dansyl, biotin, bromodeoxyuridine (BrdU), hexahistidine (6×His), phosphor-amino acids (e.g., P-tyr, P-ser, P-thr), or any other suitable label. In one embodiment the following hapten/antibody pairs are used for detection, in which each of the antibodies is derivatized with a detectable label: biotin/α-biotin, digoxigenin/α-digoxigenin, dinitrophenol (DNP)/α-DNP, 5-Carboxyfluorescein (FAM)/α-FAM. Probes may also be indirectly labeled, especially with a hapten that is then bound by a capture agent. In one method, the method may comprise hybridization with a complementary nucleic acid probe which, via a chemical bond, contains bound at least one hapten as label which is a steroid bound to at least one position of the nucleic acid which does not participate in hydrogen bond formation via a bridge of at least 4 atoms length, followed by detection of the hybridized probe using labelled anti-hapten antibody. The method may comprise hybridization with two single-stranded nucleic acid probes present in the same solution phase complementary to different regions of the nucleic acid to be detected, one nucleic acid probe serving as detector probe and containing as labelling at least one hapten bound via a chemical linkage and the other nucleic acid probe serving as capturing probe and being bound to a solid matrix. Many different hapten-capture agent pairs are available for use with the present methods. Exemplary haptens include, biotin, des-biotin and other derivatives, dinitrophenol, dansyl, fluorescein, CY5, and other dyes, digoxigenin, digoxigenin derivatives and the like. For biotin, a capture agent may be avidin, streptavidin, or antibodies. Biotin or 2,4-dinitrobenzene may be bonded to a specific oligodeoxyribonucleotide at a specific site other than the nucleotide base. Antibodies may be used as capture agents for the other haptens (many dye-antibody pairs being commercially available, e.g., Molecular Probes).

Probes may be prepared with nucleic acid tag tails instead of being directly labeled. Tails preferably do not interact with test DNA. These tails may be prepared from natural bases or modified bases such as isoC and isoG that pair only between themselves. If isoC and isoG nucleotides are used, the sequences may be separately synthesized with a 5' amino-linker, which allows conjugation to a 5'-carboxy modified linker that is synthesized on to each tagged probe. This allows separately synthesized tag sequences to be combined with known probes while they are still attached to the column. In one embodiment, 21 tagged sequences are used in combination with 1024 known probes.

In some embodiments, in order to distinguish the products of multiple target miRNA TRCs in multiplex (e.g., 5, 10, 15, 20, or more), two additional independent, probing sequences are incorporated into the TRC, each with the potential to bind one of four AlexaFluor labelled beacons. The two-color combination and order of probes binding to any particular nanosphere is unique and indicative of a particular miRNA. Multiplex testing yields highly predictable quantification of each target miRNA. Any presence of unexpected levels of fluorescence would indicate non-specific TRC/miRNA binding and nanosphere production. The final multiplex analysis of all TRCs together is conducted on ordered arrays and utilizes sequential probe hybridization of multi-state, pooled probes to determine TRC identity by fluorescent imaging.

In certain embodiments, high multiplex ligation assays of probes are used which are not labeled with fluorescent dyes, thus reducing background and assay costs. F or example for 8 colors 4×8=32 different encoding tails may be prepared and 32 probes as a pool may be used in hybridization/ ligation. I n the decoding process, four cycles each with 8 tags are used. Thus, each color is used for 4 tags used in 4 decoding cycles. After each cycle, tags may be removed or dyes photo bleached. The process requires that the last set of probes to be decoded has to stay hybridized through 4 decoding cycles.

In one embodiment, additional properties are included to provide the ability to distinguish different probes using the same color, for example $T_m$/stability, degradability by incorporated uracil bases and UDG enzyme, and chemically or photochemically cleavable bonds. A combination of two properties, such as temperature stability directly or after cutting or removing a stabilizer to provide 8 distinct tags for the same color; more than one cut type may be used to create 3 or more groups; to execute this 4-8 or 6-12 exposures of the same color may be required, demanding low photo- bleaching conditions such as low intensity light illumination that may be detected by intensified CCDs (ICCDs). For example if one property is melting temperature ($T_m$) and there are 4 tag-oligos or anchors or primers with distinct $T_m$, another set of 4 oligos can be prepared that has the first 4 probes connected to or intractable with a stabilizer that shifts the $T_m$ of these 4 oligos above the most stable oligo in the first group without stabilizer. After resolving 4 oligos from the first group by consecutive melting off, the temperature may be reduced to the initial low level, the stabilizer may be cut or removed, and 4 tagged-oligos or anchors or primers can then be differentially melted using the same temperature points as for the first group.

II. Detection of Target Nucleic Acids

Certain embodiments of the present disclosure involve the use of TRC(s) provided herein for the detection of target nucleic acids. The TRC(s) may be comprised of DNA, RNA, or analogs thereof, and/or combinations thereof. In certain embodiments, a TRC comprises one or more non-natural nucleotides. In some aspects, the target nucleic acids serve as the primers for rolling circle replication of the TRC to generate a long continuous nucleic acid molecule that contains multiple copies of the same TRC linked in series, referred to herein as concatemers of the replicated TRCs or replicated nanospheres. The replicated TRCs have intramolecular hybridization through the bridge sequences (e.g., stabilizing sequences) to form non-entangled, three-dimensional replicated nanospheres. Each nanosphere may comprise at least 100, 200, 500, 1000, 2000, 3000, 4000, 5000, 6000, 7000, 8000, 9000, 10,000, 20,000, 40,000, or 50,000 copies of the TRC depending on the length of the RCA reaction and the concentration of the target nucleic acid. These nanospheres are then detected using the probe sequences, thus enabling detection of the target nucleic acids from an initial sample.

A. Target Nucleic Acids

Embodiments of the present disclosure concern compositions and methods utilizing target nucleic acids from present with or isolated from samples. As will be appreciated by those in the art, the sample solution may comprise blood, urine, serum, lymph, saliva, anal and vaginal secretions, perspiration, semen, cells of virtually any organism, with mammalian samples being preferred and human samples being particularly preferred; environmental samples (including, but not limited to, air, agricultural, water and soil samples); biological warfare agent samples; research samples (e.g., the products of an amplification reaction, including both target and signal amplification, such as PCR amplification reactions; purified samples, such as purified genomic DNA, RNA preparations, raw samples (bacteria, virus, genomic DNA); as will be appreciated by those in the art, virtually any experimental manipulation may have been done on the samples. In particular embodiments, the target nucleic acid or population of target nucleic acids can be isolated from biological samples, such as plasma, saliva, and urine. In some embodiments, the TRC is a "naturally occurring" nucleic acid sequence which is a sequence that is present in nucleic acid molecules of organisms or viruses that exist in nature in the absence of human intervention. In some embodiments, a target is genomic DNA, messenger RNA, ribosomal RNA, microRNA, pre-microRNA, pro-microRNA, viral DNA, viral RNA, or piwi-RNA.

In some embodiments, the target nucleic acid is a nucleic acid that naturally occurs in an organism or a virus. In some embodiments, the target nucleic acid is a microRNA. In some embodiments, the target nucleic acid is present in a plurality of different nucleic acids. In some embodiments, the target is present as a single copy or in low copy (e.g., less than 0.001%, less than 0.01%, less than 0.1%, or less than 1%) in a plurality of different nucleic acids.

B. Rolling Circle Replication

Bacteriophages (or phages), such as ΦX174, M13, lambda, and some viruses can replicate their respective genomes by a "rolling circle" mechanism. An entire genome is reproduced by copying from a circular template. Unlike PCR, the rolling circle mechanism can be performed isothermally (e.g, without the need for heating or cooling cycles). The rolling circle approach has been used as an in vitro method for replicating (e.g., using one or more primers that copy only original templates) or amplifying (e.g., using two or more primers that copy both original templates as well as copies of templates) nucleic acid molecules of interest. For example, circular synthetic oligonucleotide templates, ranging from 34-to-52 bases in size, have been replicated using a rolling circle mechanism using *E. coli* Pol I DNA polymerase and a single oligonucleotide primer. The rolling circle mechanism using similar size constructs, range 26-to-74, with several polymerases, including *E. coli* Pol I, Klenow DNA polymerase, and $T_4$ DNA polymerases.

Accordingly, in some aspects, TRCs are replicated, such as to produce replicated TRCs, in a rolling circle replication (RCR) reaction. Conditions and reagents for RCR reactions are known in the art. Generally, RCR reaction components comprise single-stranded DNA circles, one or more primers that anneal to DNA circles (e.g., a target nucleic acid, including pathogenic nucleic acids and miRNAs, can function as in situ derived complementary primers), a DNA polymerase having strand displacement activity to extend the 3' ends of primers annealed to DNA circles, nucleoside triphosphates, and a conventional polymerase reaction buffer. Such components are combined under conditions that permit primers (e.g., target nucleic acids) to anneal to DNA circles and be extended by the DNA polymerase to form replicated TRCs. An exemplary RCR reaction protocol is as follows: In a 50 µL reaction mixture, the following ingredients are assembled: 2-50 pmol circular DNA, 0.5 units/µL phage φ29 DNA polymerase, 0.2 µg/µL BSA, 3 mM dNTP, 1×φ29 DNA polymerase reaction buffer (Amersham). The RCR reaction is carried out at 30-40° C., particularly 37° C. for 30 minutes to 20 hours, particularly for about 60 minutes. In some embodiments, this and other methods described herein are performed at a temperature between and including room temperature up to and including 50° C., or up to and including 40° C., or up to and including 30° C. In some embodiments, this and other methods described herein are performed at about 37° C. In some embodiments, the concentration of circular DNA in the polymerase reaction may be selected to be low (approximately 10-100 billion circles per ml, or 10-100 circles per picoliter) to avoid entanglement and other intermolecular interactions.

Polymerases and reverse transcriptases that are useful in a rolling circle mechanism generally exhibit the property of strand-displacement, which is the ability to displace a "downstream" nucleic acid strand encountered by the enzyme during nucleic acid synthesis. These strand-displacing enzymes also lack 5'-exonuclease activity. Any strand displacing polymerase or reverse transcriptase can be used in rolling circle replication or rolling circle amplification, for example and without limitation, φ29 DNA polymerase, *E. coli* Pol I, Klenow DNA polymerase, Bst DNA polymerase (large fragment), Bsm DNA polymerase (large fragment), Bsu DNA polymerase (large fragment), Vent(exo-) DNA polymerase, $T_7$ (exo-) DNA polymerase ($T_7$ Sequenase), or TopoTaq (a chimeric protein of Taq DNA polymerase and topoisomerase V), as well as mutant versions of these DNA polymerases thereof, $T_7$ RNA polymerase, $T_3$ RNA polymerase, or SP6 RNA polymerase as well as mutant versions of these RNA polymerases thereof, or avian myeloblastosis virus reverse transcriptase or Moloney murine leukemia virus reverse transcriptase, as well as mutant versions of these reverse transcriptases, such as ThermoScript reverse transcriptase, Superscript reverse transcriptase or PrimeScript reverse transcriptase. In addition to strand-displacing polymerases and reverse transcriptases, accessory proteins can further enhance the displacement of a downstream nucleic acid strand during nucleic acid synthesis by increasing the robustness, fidelity, and/or processivity of the rolling circle mechanism. Strand-displacing accessory proteins can be of any type and include, for example and without limitation, helicases, single- stranded binding proteins, topoisomerases, reverse gyrases, and other proteins that stimulate accessory proteins, for example and without limitation, *Escherichia coli* (*E. coli*) MutL protein or thioredoxin. DNA helicases are useful in vivo to separate or unwind two complementary or substantially complementary DNA strands during DNA replication. Helicases can unwind nucleic acid molecules in both a 5'-to-3' direction, for example and with limitation, bacteriophage $T_7$ gene 4 helicase, DnaB helicase and Rho helicase and a 3'-to-5' direction, for example and with limitation, *E. coli* UvrD helicase, PcrA, Rep, and NS3 RNA helicase of *hepatitis C* virus. Helicase may be obtained from any source and include, for example and without limitation, *E. coli* helicases (i.e., I, II [UvrD], III, and IV, Rep, DnaB, PriA and PcrA), bacteriophage $T_4$ gp41, bacteriophage $T_7$ gene 4 helicase, SV40 Large T antigen, Rho helicase, yeast RAD helicase, thermostable UvrD helicases from *T. tengcongensis*, and NS3 RNA helicase of *hepatitis C virus*, as well as mutant versions of these and other helicases. Single-stranded binding protein binds single-stranded DNA with greater affinity that double-stranded DNA. These proteins bind cooperatively, favoring the invasion of single-stranded regions and therefore destabilizing duplex structures. For example and without limitation, single-stranded binding protein can exhibit helix-destabilizing activity by removing secondary structure and can displace hybridized nucleic acid molecules. Single-stranded binding proteins may be obtained from any source and include, for example and without limitation, bacteriophage $T_4$ gene 32 protein, RB 49 gene 32 protein, *E. coli* single-stranded binding protein, φ29 single- stranded binding protein or bacteriophage $T_7$ gene 2.5, as well as mutant versions of these and other single-stranded binding proteins, such as bacteriophage $T_7$ gene 2.5 F232L.

The TRCs can be subject to a rolling circle replication using highly processive, strand-displacing polymerases, such as φ29 polymerase. The rolling circle replication can be performed in one or two steps. First, TRCs are allowed to hybridize with complementary primers under appropriate "hybridization conditions," which include temperature, factors such as salts, buffer and pH, detergents, and organic solvents. Blocking agents such as Bovine Serum Albumin (BSA) or Denhardt's reagent may be used as part of the hybridization conditions. Second, an appropriate polymerase or replisome and nucleotide mix are provided to the first reaction mixture to produce amplified or replicated dumbbell templates. The hybridization and amplification or replication conditions are optimized based on several factors, including but not limited, to the length and sequence composition of the stem region of the dumbbell templates, the hybridization conditions, the specific polymerase or replisome used herein, and the reaction temperature. In certain embodiments, the reaction temperature can be about 10° C. to 65° C. In other embodiments, the reaction temperature can be about 15° C. to 37° C. In other embodiments, the reaction temperature can be about 20° C. to 25° C. In certain embodiments, the temperature is increased in select time intervals. For example, without limitations, the reaction is maintained for five minutes at 10° C., then five minutes at 15° C., five minutes at 20° C., then five minutes at 25° C., and five minutes at 30° C.

The RCR and RCA reactions may further comprise a carrier such as a buffer, optionally comprising a preservative, one or more salts, one or more enzymes such as a polymerase, nucleotides suitable for nucleic acid synthesis. The reaction may include one or more of the following reagents: buffer (e.g., KCl, $MgCl_2$, Tris-HCl), dNTPs (e.g., dATP, dCTP, dGTP, dTTP at concentrations of, e.g., about 50 to about 100 μM), polymerase (e.g., at concentrations of about 0.5-2.0 units per 50 μl reaction), and/or water. Salts and buffers include those familiar to those skilled in the art, including those comprising $MgCl_2$, and Tris-HCl and KCl, respectively. Buffers may contain additives such as surfactants, dimethyl sulfoxide (DMSO), glycerol, bovine serum albumin (BSA) and polyethylene glycol (PEG), as well as others familiar to those skilled in the art. Nucleotides are generally deoxyribonucleoside triphosphates, such as deoxyadenosine triphosphate (dATP), deoxycytidine triphosphate (dCTP), deoxyguanosine triphosphate (dGTP), and deoxythymidine triphosphate (dTTP), and are also added to a reaction adequate amount for amplification of the target nucleic acid.

In one exemplary method, based on φ29 polymerase processivity and time titration data, successful 60 minute reactions produce high-molecular weight (>70 kb) DNA products. Due to the highly entangled nature of replicated nanospheres, their migration through agarose gels is markedly different from other oligonucleotides in this size range; this can be confirmed by gel electrophoresis.

In some embodiments, the target nucleic acid has a length greater than that of the TRC to which it hybridizes to, thus producing a 3' overhang and/or a 5' overhang. For example, viral nucleic acids from oral samples such as saliva, usually contain significantly higher molecular weight fragments (>3 kb). This size discrepancy suggests the presence of lengthy overhanging sequences at both the 5'-end and/or 3'-end of hybridized pathogenic nucleic acids on TRCs. While the former does not present any apparent problem for DNA replication, the presence of 3'-end overhanging nucleotides does create an impediment. Accordingly, in some aspects, to transform the target nucleic acid into functional primers the 3' overhang is removed prior to the RCR reaction. An exonuclease is used to remove the 3' overhang up to the double-stranded complementary region and present a 3'-OH group. In some aspects, the intrinsic 3'-exonuclease activity of the DNA polymerase is leveraged to remove the 3'-overhang. In other aspects, an exonuclease is introduced such as Exonuclease T.

In certain embodiments, exonucleases can be useful to remove undesired nucleic acid molecules that did not successfully ligate to form TRCs. These undesired nucleic acid molecules may have one or more 5'-ends or 3'ends that may be in the form of a blunt-ended, 5'-protuding ends, and/or 3'-protruding ends, or may exist in single-stranded form. These undesired nucleic acid molecules include, but not limited to, single-stranded nucleic acid molecules, oligonucleotides that may not have formed into a TRC structure, and unligated hairpin structures. Exonuclease III (also called Exo III) catalyzes the stepwise removal of mononucleotides from 3'-hydroxyl termini of double-stranded DNA. A limited number of nucleotides are removed during each binding event, resulting in coordinated progressive deletions within the population of DNA molecules. The preferred substrates of Exo III are nucleic acid molecules containing blunt-ends or 5'-protuding ends, although the enzyme also acts at nicks in double-stranded DNA to produce single-strand gaps. Exo III is not active on single-stranded DNA, and thus 3'-protruding ends are resistant to cleavage. The degree of resistance depends on the length of the extension, with extensions four bases or longer being essentially resistant to cleavage. This property can be exploited to produce unidirectional deletions from a linear molecule with one resistant (3'-protruding ends) and one susceptible (blunt-ends or 5'-protruding ends) terminus. Exonuclease III activity depends partially on helical structure and displays sequence dependence (C>A=T>G). Temperature, salt concentration and the ratio of enzyme to DNA greatly affect enzyme activity, requiring reaction conditions to be tailored to specific applications. Exonuclease VII (also called Exo VII) cleaves single-stranded DNA from both 5'→3' and 3'→5' direction. This enzyme is not active on linear or circular double-stranded DNA. It is useful for removal of single-stranded oligonucleotide primers and hairpins from a completed PCR reaction and post-ligation reactions when creating dumbbell constructs. Digestion of single-stranded DNA by Exonuclease VII is metal-independent. Exo III and Exo VII can be used in combination to remove undesired nucleic acid molecules that did not successfully ligate to form TRCs.

C. Array

Embodiments of the present disclosure concern detection of the replicated TRCs. The replicated TRCs can be distributed randomly in an ordered pattern on planar or substantially planar slide substrate, fiber-optic substrate, or, semiconductor device substrates containing wells, depressions, or other containers, vessels, features, or locations. In some embodiments, the replicated TRCs are dispersed on an array of optically resolvable discrete spaced apart regions. In some aspects, each discrete spaced apart region has an area of less than one (1) $\mu m_2$, such that substantially all the discrete spaced apart regions have at most one replicated TRC attached.

The substrate or solid support on which TRCs and primers may be attached can be comprised of any material, for example and without limitation, a solid material, a semi-solid material (e.g., [i] a composite of a solid support and a gel or matrix material or [ii] linear or cross-linked polyacrylamide, cellulose, cross-linked agarose, and polyethylene glycol), or fluid or liquid material. The substrate can also be comprised of any material that has any dimensions and shape, for example and without limitation, square, trapezoidal, spherical, spheroidal, tubular, pellet-shaped, rod-shaped, or octahedral. The substrate should contain properties that are compatible with the present disclosure (e.g., exhibit minimal interference with replication, amplification, or detection processes). In certain embodiments, the substrate is nonporous. In certain embodiments, the substrate is porous. In certain embodiments, the substrate can be comprised of a hydrophilic porous matrix, such as a hydrogel. In certain embodiments, the solid material comprises, for example and without limitation, a glass material (i.e., borosilicate, controlled pore glass, fused silica, or germanium-doped silica), silicon, zirconia, titanium dioxide, a polymeric material (e.g., polystyrene, cross-linked polystyrene, polyacrylate, polymethylacrylate, polydimethylsiloxane, polyethylene, polyfluoroethylene, polyethyleneoxy, polypropylene, polyacrylamide, polyamide such as nylon, dextran, cross-linked dextran, latex, cyclic olefin polymer, cyclic olefin copolymer, as well as other co-polymers and grafts thereof), or a metallic material. Solid substrates can consist, for example and without limitation, of one or more membranes, planar surfaces, substantially planar surfaces, non-planar surfaces, microtiter plates, spherical beads, non-spherical beads, fiber-optics, fiber-optics containing spherical beads, fiber-optics containing non-spherical beads, semi-conductor devices, semi-conductor devices containing spherical beads, semi-conductor devices containing non-spherical beads, slides with one or more wells containing spherical beads, slides with one or more wells containing non-spherical beads, filters, test strips, slides, cover slips, or test tubes. In certain embodiments, the semi-solid material comprises, for example and without limitation, linear or cross-linked polyacrylamide, cellulose, cross-linked agarose, and polyethylene glycol.

One or more primers can be attached to a substrate by any suitable means. In certain embodiments, the attachment of one or more primers to the substrate, for example and without limitation, is mediated by covalent bonding, by hydrogen bonding (i.e., whereby the primer is hybridized with another complementary oligonucleotide covalently attached to the substrate and still serves a replication competent or amplification competent function), Van der Waal forces, physical adsorption, hydrophobic interactions, ionic interactions or affinity interactions (e.g., binding pairs such as biotin/streptavidin or antigen/antibody). In certain embodiments, one member of the binding pair is attached to the substrate and the other member of the binding pair is attached to one or more primers. The attached of one or more primers to the substrate occurs through the interaction of the two member of the binding pair.

Replicated nanospheres may be stochastically loaded onto functionalized, high-density ordered arrays. These arrays, represent an ordered matrix onto which individual replicated nanospheres may discretely and independently bind. This unbiased but highly organized surface, coupled with the use of TRC/miRNA-specific fluorescent probing, enables the TRC platform to efficiently obtain quantitative miRNA population data. The organizational capability of the microfabricated array is based on electrostatic interactions between its dual substrate surface and DNA. A grid of distinct aminosilane pads induce binding of individual replicated nanospheres at selective locations by size restriction—only a single replicated nanosphere can bind at a given aminosilane pad. Hexamethyldisilizane (HMDS) fills the space between the aminosilane pads and discourages promiscuous binding. Importantly, replicated nanospheres are not topologically addressed but may bind indiscriminately to any unoccupied aminosilane pad.

In some embodiments, fluorescent probes (not beacons) may be used to interrogate the bound replicated nanospheres at this stage. Single-product identification is based on probe signatures. For example, sixteen different miRNAs can be easily decoded with four colors (i.e., blue, green, red and yellow) and two probe hybridization events. More complex coding strategies can permit greater flexibility with the potential to eliminate problematic color combinations. Probing events follow a cyclic pattern of washing, hybridization, washing, and imaging. Following removal of the first probe set, a second probe set is hybridized, washed, and imaged. Identification of fluorescent signatures is used to decode an individual nanosphere for a particular miRNA. High-resolution imaging is accomplished using an epi-fluorescence detection microscope. The entire array may be subdivided, and four-color images of each subsection are generated corresponding to the specific fluorophores used in decoding. The collated and processed image data is then decoded and quantified based on the observed probe signatures using image analysis software. Using the concentrations of target miRNAs in the tested populations, an exact target miRNA count can be estimated for each reaction.

By design, patterned arrays and ordered arrays are expected to provide replicated TRCs template arrays or amplified TRC template arrays that are spatially and spectrally resolvable for detecting a nucleic acid molecule. In certain embodiments of a random array, one or more primers can be covalently bonded to the substrate to form a high-density lawn of immobilized primers on a planar or substantially planar surface. The one or more primers may be attached by any means, for example and without limitation, by methods involving dropping, spraying, plating or spreading a solution, emulsion, aerosol, vapor, or dry preparation. By introducing dumbbell templates onto the substrate in limiting dilution fashion, one or more primers will contact the dumbbell template, enabling the rolling circle mechanism in the presence of polymerase to produce one or more replicated dumbbell templates (e.g., replicated dumbbell template array) or amplified dumbbell templates (e.g., amplified dumbbell template array) that are spatially and spectrally resolvable for detecting a nucleic acid molecule. In certain embodiments of a random assortment in patterned arrays, one or more primers can be covalently bonded to the substrate to form high-density, immobilized primers on one of more spherical or non-spherical beads. By introducing dumbbell templates onto the substrate in limiting dilution using an oil in water emulsion system, one or more primers will contact the dumbbell template, enabling the rolling circle mechanism to produce one or more replicated dumbbell templates or amplified dumbbell templates. In certain embodiments, replicated dumbbell templated beads or amplified dumbbell templated beads can be enriched to remove those beads that failed to replicate or amplify dumbbell templates based on Poisson statistics of distributing single molecules. Replicated dumbbell templated beads or amplified dumbbell templated beads, with or without enrichment, can then be distributed randomly in a ordered pattern on planar or substantially planar slide substrate, fiber-optic substrate, or, semi-conductor device substrates containing wells, depressions, or other containers, vessels, features, or locations. In other certain embodiments of a random assortment in patterned arrays, one or more prefabricated hydrophilic features (i.e., spots) on the surface can be surrounded by hydrophobic surfaces for the covalent bonding of one or more primers to the substrate. For example and without limitation, patterned arrays can be created photolithographically etched, surface modified silicon substrates with grid-patterned arrays of ~300 nm spots. By introducing the dumbbell templates onto a patterned substrate in limiting dilution fashion, the primer will contact the dumbbell template, enabling the rolling circle mechanism to produce one or more replicated dumbbell templates or amplified dumbbell templates. In certain embodiments, the prefabricated hydrophilic spots can be made small even to accommodate only one replicated dumbbell template or amplified dumbbell template. As distributing single molecules based on Poisson statistics results in a considerable fraction of no template spots, following the rolling circle procedure, additional rounds of distributing, contacting, and rolling circle may be employed to increase the density of replicated dumbbell templates or amplified dumbbell templates on the substrate. In certain embodiments of "knowns" patterned in ordered arrays, one or more known primers can be printed (i.e., spotted arrays) or made in situ at addressable locations on the substrate. By introducing the dumbbell templates onto a patterned substrate in limiting dilution fashion, one or more primers will contact the dumbbell template, enabling the rolling circle mechanism to produce one or more replicated dumbbell templates or amplified dumbbell templates.

Accordingly, in some embodiments the replicated TRCs can be stochastically loaded onto functionalized, high-density ordered arrays. The arrays can be photolithographically etched, surface-modified (SOM) silicon substrates with grid-patterned arrays. The individual replicated TRCs can discretely and independently bind the array. This unbiased but highly organized surface, coupled with the use of TRC/target nucleic acid-specific probing, enables the efficient detection and quantification of the target nucleic acid population. The organizational capability of the microfabricated array is based on electrostatic interactions between its dual substrate surface and DNA. A grid of distinct aminosilane pads induce binding of individual replicated TRCs at selective locations by size restriction—only a single replicated TRCs can bind at a given aminosilane pad. Hexamethyldisilizane (HMDS) fills the space between the aminosilane pads and discourages promiscuous binding. The replicated TRCs will not be topologically addressed but may bind indiscriminately to any unoccupied aminosilane pad.

Generally, densities of single molecules are selected that permit at least 20%, or at least 30%, or at least 40%, or at least a majority of the molecules to be resolved individually by the signal generation and detection systems used. Whenever optical microscopy is employed, for example with molecule-specific probes having fluorescent labels, a density is selected such that at least a majority of single molecules have a nearest neighbor distance of 200 nm or greater; and in another aspect, such density is selected to ensure that at least seventy percent of single molecules have a nearest neighbor distance of 200 nm or greater. In still another aspect, whenever optical microscopy is employed, for example with molecule-specific probes having fluorescent labels, a density is selected such that at least a majority of single molecules have a nearest neighbor distance of 300 nm or greater; and in another aspect, such density is selected to ensure that at least seventy percent of single molecules have a nearest neighbor distance of 300 nm or greater, or 400 nm or greater, or 500 nm or greater, or 600 nm or greater, or 700 nm or greater, or 800 nm or greater. In still another embodiment, whenever optical microscopy is used, a density is selected such that at least a majority of single molecules have a nearest neighbor distance of at least twice the minimal feature resolution power of the microscope. In another aspect, polymer molecules of the present disclosure are disposed on a surface so that the density of separately detectable polymer molecules is at least 1000 per $\mu m^2$, or at least 10,000 per $\mu m^2$, or at least 100,000 per $\mu m^2$.

In another aspect of the disclosure, the requirement of selecting densities of randomly disposed single molecules to ensure desired nearest neighbor distances is obviated by providing on a surface discrete spaced apart regions that are substantially the sole sites for attaching single molecules. That is, in such embodiments the regions on the surface between the discrete spaced apart regions, referred to herein as "inter-regional areas," are inert in the sense that the replicated TRCs do not bind to such regions. In some embodiments, such inter-regional areas may be treated with blocking agents, e.g., DNAs unrelated to replicated TRC DNA, other polymers, and the like. Generally, the area of discrete spaced apart regions is selected, along with attachment chemistries, macromolecular structures employed, and the like, to correspond to the size of single molecules of the present disclosure so that when single molecules are applied to surface substantially every region is occupied by no more than one single molecule. The likelihood of having only one single molecule per discrete spaced apart region may be increased by selecting a density of reactive functionalities or capture oligonucleotides that results in fewer such moieties than their respective complements on single molecules. Thus, a single molecule will "occupy" all linkages to the surface at a particular discrete spaced apart region, thereby reducing the chance that a second single molecule will also bind to the same region. In particular, in one embodiment, substantially all the capture oligonucleotides in a discrete spaced apart region hybridize to adaptor oligonucleotides a single macromolecular structure. In one aspect, a discrete spaced apart region contains a number of reactive functionalities or capture oligonucleotides that is from about ten percent to about fifty percent of the number of complementary functionalities or adaptor oligonucleotides of a single molecule. The length and sequence(s) of capture oligonucleotides may vary widely, and may be selected in accordance with well-known principles.

In one aspect, the lengths of capture oligonucleotides are in a range of from 6 to 30 nucleotides, and in another aspect, within a range of from 8 to 30 nucleotides, or from 10 to 24 nucleotides. Lengths and sequences of capture oligonucleotides are selected (i) to provide effective binding of macromolecular structures to a surface, so that losses of macromolecular structures are minimized during steps of analytical operations, such as washing, etc., and (ii) to avoid interference with analytical operations on analyte molecules, particularly when analyte molecules are DNA fragments in a nanosphere. In regard to (i), in one aspect, sequences and lengths are selected to provide duplexes between capture oligonucleotides and their complements that are sufficiently stable so that they do not dissociate in a stringent wash. In regard to (ii), if DNA fragments are from a particular species of organism, then databases, when available, may be used to screen potential capture sequences that may form spurious or undesired hybrids with DNA fragments. Other factors in selecting sequences for capture oligonucleotides are similar to those considered in selecting primers, hybridization probes, oligonucleotide tags, and the like.

In one aspect, the area of discrete spaced apart regions is less than 1 $\mu m^2$; and in another aspect, the area of discrete spaced apart regions is in the range of from 0.04 $\mu m^2$ to 1 $\mu m^2$; and in still another aspect, the area of discrete spaced apart regions is in the range of from 0.2 $_m{}^2$ to 1 $\mu m^2$. In another aspect, when discrete spaced apart regions are approximately circular or square in shape so that their sizes can be indicated by a single linear dimension, the size of such regions are in the range of from 125 nm to 250 nm, or in the range of from 200 nm to 500 nm. In one aspect, center-to-center distances of nearest neighbors of such regions are in the range of from 0.25 $\mu m$ to 20 $\mu m$; and in another aspect, such distances are in the range of from 1 $\mu m$ to 10 $\mu m$, or in the range from 50 to 1000 nm. In particular aspects, spaced apart regions for immobilizing nanospheres are arranged in a rectilinear or hexagonal pattern.

In certain embodiments of the disclosure, photolithography, electron beam lithography, nano imprint lithography, and nano printing may be used to generate such patterns on a wide variety of surfaces. These techniques can be used to generate patterns of features on the order of $\frac{1}{10}^{th}$ of a micron and have been developed for use in the semiconductor industry. In one embodiment, a single "masking" operation is performed on the DNA array substrate, as opposed to the 20 to 30 masking operations typically needed to create even a simple semiconductor. Using a single masking operation eliminates the need for the accurate alignment of many masks to the same substrate. There is also no need for doping of materials. Minor defects in the pattern may have little to no effect on the usability of the array, thus allowing production yields to approach 100%. In certain embodiments, stereolithography (i.e., stereolithography 3D printer or digital light processing 3D printer) can be used instead of lithography techniques to print the array device.

In one embodiment, high density structured random DNA array chips have capture oligonucleotides concentrated in small, segregated capture cells aligned into a rectangular grid formation. Preferably, each capture cell or binding site is surrounded by an inert surface and may have a sufficient but limited number of capture molecules (100-400). Each capture molecule may bind one copy of the matching adaptor sequence on the RCR produced nanosphere. By providing enough RCR products almost every spot on the array may contain one and only one unique TRC target.

In one exemplary method, the replicated TRCs can be pipetted individually on to separate ordered arrays. After a short incubation period which allows the replicated TRCs to bind to the functionalized surface, the arrays are then prepared for probe hybridization by rinsing in a neutral pH buffer to remove contaminants from the initial reaction.

D. Probe Detection

The oligonucleotide product of an individual TRC reaction (one target oligonucleotide hybridizing with a single TRC) is composed of concatenated replicates of the TRC compliment sequence. Depending on the reaction conditions (duration and polymerase), the overall length may be tens of kilobases and the number of replicates can range from tens to thousands. The product oligonucleotide forms a tertiary structure with both single and double-stranded domains. The rapid replication process and lengthy product can be detected by non-specific methods or more directed sequence-specific detection methods may be employed.

In certain embodiments, the replicated TRCs can be detected with oligonucleotide probes. The oligonucleotide probes can be labeled oligonucleotide probes. The oligonucleotide probes can be labeled DNA probes. In certain embodiments, the oligonucleotide probe can be attached to one or more of a fluorophore, a chromophore, a radioisotope, an enzyme, or a luminescent compound, or combinations thereof.

In certain embodiments, the replicated TRCs can be detected with a range of instruments capable of detecting various accessory sequences, probes and moieties within the replicated TRC. Exemplary instruments include a (FIG. 2C) machine for detection of fluorescent molecular probes or Sybr staining of replicated products in real-time; a fluorescent or colorimetric plate reader for detection of replicated TRCs by fluorescent dyes, probes or pH sensitive stains at the completion of RCR or RCA; a scanning fluorescence microscope for the detection and quantitation of replicated TRCs on stochastically arranged or location specific arrays; imaging using smartphones or other portable handheld imaging devices for use with colorimetric or photosensitive probes or dyes; flow cytometers capable of detecting fluorescent probes bound to replicated TRCs or fluorescent nucleotides incorporated into replicated TRCs.

Automation of the probe hybridization reactions and image collection may be accomplished with standard microfluidic devices and modifications to a microscope. Briefly, the former includes the use of computer-controlled microfluidic valves and peristaltic pumps to sequentially deliver reagents for washing and probe hybridization. The coordinated, intermittent four-color imaging is accomplished using a scanning XY-stage and the Nikon Perfect Focus System, which minimizes background and image drift.

1. Non-Specific Detection Methods

TRC products can be detected by single or double-stranded oligonucleotide intercalating dyes (stains) (Sybr, EtBr, etc.). The dyes bind non-specifically to oligonucleotides in various forms and fluoresce under the proper excitation wavelengths, indicating both a positive reaction and with the correct instruments, a relative quantity of product that can indicate the amount of starting material.

In this method, a positive reaction between TRC and target oligonucleotide would produce a product that could be detected with Sybr in real-time using an RT-PCR instrument or as an end-point detection method using a microplate reader. Using a titration scale, the products could be quantified and equated to the starting target concentration. In a simplified version, the TRC reaction could be read out simply as a positive or a negative for the target oligonucleotide.

In a similar manner, a positive reaction between TRC and target oligonucleotide could be detected with a colorimetric dye, many of which are pH sensitive. The rapid TRC replication reaction would reduce pH, producing a color change detectable with a microplate reader, spectrophotometer, or by the naked eye. The reaction could be identified as positive or negative, or the initial target oligonucleotide concentration could be calculated.

An additional method of non-specific detection involves the incorporation of modified nucleotides into the product. These could include fluorescently labeled, radiolabeled, or biotinylated nucleotides. The isolated products could then be quantified with appropriate detection instruments.

2. Sequence Specific Detection Methods

TRCs may contain sequence elements that correspond with a unique target. The resulting target-specific TRC reaction products have highly replicated domains that permit sequence-specific product isolation, detection, and/or quantification, notably for use in multiplex reaction systems. Multiple such sequences may be incorporated to achieve higher order multiplexing, possibly requiring multiple probing cycles.

Engineered sequence domains that are highly replicated during the TRC reaction may be bound with fluorescent oligonucleotides in the form of probes or beacons. Probes are short sequences with attached fluorophores that hybridize with their complimentary sequence; beacons are similar, but contain a cis-acting quencher to mask the fluorescent signal when beacons are not bound to the target sequence. Following hybridization, excess probe or beacon is washed away and analysis of the bound products may proceed with overall fluorescence, or single molecule quantification and decoding.

For example, four target-specific TRCs may be used to analyze four different target concentrations in a single reaction. Four beacons with four different fluorescent signals are used. During the reaction, a single target-specific beacon binds to TRC reaction product corresponding with that target oligonucleotide. The level of fluorescence can be monitored during the reaction or at end-point. Similarly, the level of fluorescence for the other three targets may also be monitored in the same way.

Detection methods may combine various methods—for example, TRC reactions could be run with labeled nucleotides; the products of which may then be distributed on a location specific array to be quantified by scanning fluorescent microscopy.

Alternatively, the highly-entangled but discrete products of the TRC reaction may be distributed on an ordered array based on various chemistries. Probe or beacon hybridization can take place prior to or after arraying. Individual product detection and quantification can then proceed using a microarray reader or fluorescence microscopy.

An alternative sequence-specific detection method involves isolation of a TRC reaction product to a specific, known location on an ordered array. Hybridization of the product is achieved with immobilized oligonucleotides that are specific to the target product; TRC reaction products would then be captured at a defined location for quantification based on array address. In this manner, multiple targets could be analyzed in the same reaction on the same slide.

Single-product identification can be performed. For example, sixteen different miRNAs can be easily decoded with four colors (e.g., blue, green, red and yellow) and two probe hybridization events. More complex coding strategies will permit greater flexibility with the potential to eliminate problematic color combinations. Probing events follow a cyclic pattern of washing, hybridization, washing, and imaging. Following removal of the first probe set, a second probe set will be hybridized, washed, and imaged. Identification of fluorescent signatures can be used to decode an individual nanosphere for a particular miRNA. High-resolution imaging is accomplished using an epi-fluorescence detection microscope. The entire array is subdivided, and four-color images of each subsection is generated corresponding to the specific fluorophores used in decoding. The collated and processed image data is then be decoded and quantified based on the observed probe signatures. Coordinated, intermittent four-color imaging can be accomplished using a scanning XY-stage and Nikon Perfect Focus system, which minimizes background and image drift. The digital readout displays tight correlation (e.g., <5% from calculated count) with predicted species counts for the constructed target populations with sensitivity (e.g., <10 fM) and specificity (e.g., DF >30).

Using the concentrations of target miRNAs in the tested populations, an exact target miRNA count can be estimated for each reaction. The number of miRNA-specific nanospheres detected on the array should be significantly close to this value. Fluorescence intensity may be used to indicate replicated TRC size.

Signals from replicated TRCs on arrays can generated and detected by a number of detection systems, including, but not limited to, scanning electron microscopy, near field scanning optical microscopy (NSOM), and total internal reflection fluorescence microscopy (TIRFM). The application of such techniques for analyzing and detecting nanoscale structures on surfaces is known in the art.

In one aspect, instruments for use with arrays of the present disclosure comprise three basic components: (i) a fluidics system for storing and transferring detection and processing reagents, e.g., probes, wash solutions, and the like, to an array; (ii) a reaction chamber, or flow cell, holding or comprising an array and having flow-through and temperature control capability; and (iii) an illumination and detection system. In one embodiment, a flow cell has a temperature control subsystem with ability to maintain temperature in the range from about 5-95° C., or more specifically 10-85° C., and can change temperature with a rate of about 0.5-2° C. per second.

In one embodiment, four or more cameras may be used, preferably in the 10-16 megapixel range. Multiple band pass filters and dichroic mirrors may also be used to collect pixel data across up to four or more emission spectra. To compensate for the lower light collecting power of the decreased magnification objective, the power of the excitation light source can be increased. Throughput can be increased by using one or more flow chambers with each camera, so that the imaging system is not idle while the samples are being hybridized/reacted. Because the probing of arrays can be non-sequential, more than one imaging system can be used to collect data from a set of arrays, further decreasing assay time.

In one aspect, suitable illumination and detection system for fluorescence-based signal is a Zeiss Axiovert 200 equipped with a TIRF slider coupled to an 80 milliwatt 532 nm solid state laser. The slider illuminates the substrate through the objective at the correct TIRF illumination angle. TIRF can also be accomplished without the use of the objective by illuminating the substrate though a prism optically coupled to the substrate. Planar wave guides can also be used to implement TIRF on the substrate Epi illumination can also be employed. The light source can be rastered, spread beam, coherent, incoherent, and originate from a single or multi-spectrum source.

3. Bead-Based Detection

TRC technology may be used for the identification of concrete miRNA disease signatures and for efficiently and effectively analyzing miRNA populations in patients, providing comprehensive health information in a convenient and functional platform. In some embodiment, integration of the TRC technology with the medium-plex Luminex 200 platform (e.g., up to 100 assays) delivers a robust, scalable, and cost-effective solution to replace underperforming protein, DNA, and RNA-based tests.

Typical amplification-based protocols demand that samples be divided over multiple reactions, with each reaction targeting a separate and distinct miRNA. This can be problematic given the already low concentration of circulating miRNAs and the small volume of precious clinical samples. More detrimental is the likelihood that rare but informative miRNA species will be diluted out over many misguided reactions, leading to false negatives. The streamlined TRC approach uses a simplified reaction in which all target miRNAs are bound and replicated in a single tube, eliminating the possibility of dilution bias and making subtle variations in target miRNA easier to detect over background noise.

Luminex xMAP microspheres incorporate a number of features that can be complimentary to TRC miRNA detection and an ideal platform for diagnostic assay development. (i) Oligonucleotides may be covalently coupled to surface of each microsphere in varying densities. (ii) Microspheres are embedded with preselected ratios of two or three fluorescent dyes, enabling deconvolution of each reaction target upon microsphere detection. Upon target assignment, the platform analyzer further detects the presence of fluorescent reporter molecules bound to the surface of each bead. (iii) MagPlex microspheres are magnetized to facilitate rapid isolation.

In some embodiments, each bead-type contains a specific TRC construct bound to the surface along with cis-TRC-specific secondary primers. Specific bead types indicate the target miRNA species and the presence of a fluorescent signal, incorporated as a labeled nucleotide during RCR and subsequent rolling circle amplification (RCA), indicate a positive miRNA-TRC reaction. Functionalized, product-bound beads are isolated for rapid production and analysis on the Luminex platform.

Figure 6:
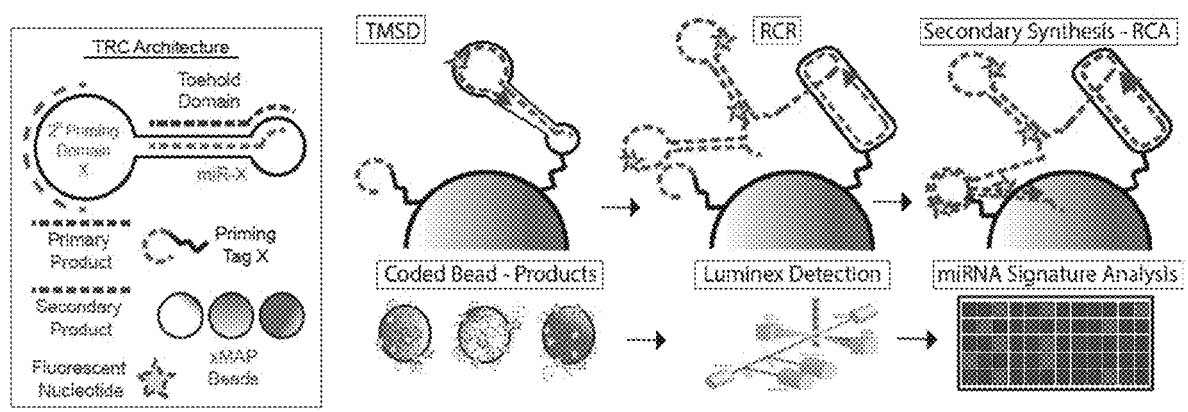
FIG. 6: TRCs bound to solid support triggering RCR and RCA. Detected by intercalating dye.

Luminex MagPlex beads contain carboxyl groups to facilitate the attachment of numerous macromolecules, including nucleic acids. As TRCs are circular in nature, amino-modifier C6 dT phosphoramidates may be used during synthesis of TRC oligonucleotides for coupling to Luminex beads. TRC-specific, complementary, secondary primers may also be attached to the Luminex beads to further extend the unique replicated TRC products, covalently attaching such products to the beads. This process results in a highly-intertwined but discrete, bead-product detectable on the Luminex 200 platform (FIG. 6).

To label replicated TRC products for detection on Luminex platforms, fluorescently-labelled nucleotides (e.g., Fluorescein-12-dCTP; PerkinElmer) may be utilized. Previous experience with Bst and Bsu polymerases have demonstrated efficient incorporation of such modified nucleotides in RCR. Alternatively, an intercalating dye such as Sybr could be used to detect replicated TRCs bound to beads.

Microsphere analysis may be carried out according to the standard operating protocol provided by Luminex. The Luminex 200 instrument is capable of simultaneously analyzing up to 100 unique reactions (e.g., 100 miRNA targets) with more advanced versions of the technology capable of handling up to 500 unique reactions. Luminex's xPONENT software may be used for continuous monitoring and quantification of all target miRNAs.

III. Methods of Use

In some embodiments, the methods provided herein concern the utilization of pathogenic nucleic acid or miRNA signatures as reliable, circulating biomarkers for disease detection, stratification, and intervention. In some aspects, the methods are used for the early detection of cancer, particularly pancreatic cancer. The dynamic, disease-specific, and intervention-responsive nature of extra-cellular and circulating miRNA populations is used to indicate disease pathogenesis and progression. Because of the quantitative nature of detection methods, the compositions and methods described herein can be used to quantitate target molecules whose abundance is indicative of a biological state or disease condition, for example, blood markers that are upregulated or downregulated as a result of a disease state. In addition, the compositions and methods described herein can be used to provide prognostic information that assists in determining a course of treatment for a patient. For example, the amount of a particular marker, such as miRNA, for a tumor can be accurately quantified from even a small sample from a patient.

In certain embodiments, the TRC platform of the present disclosure is used for the detection, stratification, and intervention of conditions including various infectious diseases such as those caused by viruses, e.g., HIV-1, EBV, hepatitis, herpes viruses, enteric viruses, respiratory viruses, rhabdovirus, rubeola, poxvirus, paramyxovirus, morbillivirus, etc. are of interest. Infectious agents of interest also include bacteria, such as *Pneumococcus, Staphylococcus, Bacillus, Streptococcus, Meningococcus, Gonococcus, Escherichia, Klebsiella, Proteus, Pseudomonas, Salmonella, Shigella, Hemophilus, Yersinia, Listeria, Corynebacterium, Vibrio, Clostridia, Chlamydia trachomatis, Mycobacterium, Helicobacter* and *Treponema*; protozoan pathogens, and the like.

The methods of the present disclosure are suitable for diagnosing any diseases for which a differential expression of miRNAs compared to healthy controls or other diseases exists. In particular, the method may be used for diagnosing cancer including bladder cancer, brain cancer, breast cancer, colon cancer, endometrium cancer, gastrointestinal stromal cancer, glioma, head- and neck cancer, kidney cancer, leukemia, liver cancer, lung cancer, lymph node cancer, melanoma, meninges cancer, ovarian cancer, pancreas cancer, prostate cancer, sarcoma, stomach cancer, testicular cancer, thyroid cancer, thymus cancer and Wilms' tumor. The diagnosis may comprise determining type, rate and/or stage of cancer. The course of the disease and the success of therapy such as chemotherapy may be monitored. The method of the present disclosure provides a prognosis on the survivor rate and enables to determine a patient's response to drugs.

The present methods may also be used for diagnosing chronic obstructive pulmonary disease (COPD), endometriosis, polycystic ovarian syndrome, multiple sclerosis, lupus, liver disease, Parkinson's disease, Alzheimer's disease, arthritis, gout, glucose metabolism disorders, alcoholism, lipid metabolism disorders, retinal and other ocular disorders and diseases, emphysema, pelvic organ prolapse, substance-induced psychoses, esophagitis, aortic diseases, placenta previa, stomach ulcers, coronary restenosis, irritable bowel syndrome, metabolic bone diseases, hemophilia, cardiomyopathies, insulin resistance, cardiotoxicity, hypertension, coronary artery disease, Aicardi-Goutières syndrome, glaucoma, intestinal diseases, kidney neoplasms, prostatitis, benign prostatic hypertrophy, hormonal disorders and embolisms.

In certain embodiments, the TRC platform is used for the detection and monitoring of type I Diabetes. The timely diagnosis and management of microvascular complications in type 1 Diabetes (T1D) represents a challenging paradigm for clinicians and a pressing need for those suffering from the disease. Current diagnostic approaches fail in their ability to sensitively, specifically, and comprehensively detect the earliest molecular changes that underlie such complications, nor do they have the ability to resolve individual complication risk and progression at the earliest stages, when intervention is most effective. Accordingly, embodiments of the present disclosure provide a novel detection and surveillance platform for the digital quantitation of cell-free miRNA signatures indicative of risk and progression for three important T1D microvascular complications: diabetic retinopathy (DR), diabetic nephropathy (DN), and diabetic peripheral neuropathy (DPN). Clinical intervention, when initiated in the early stages of these complications, can limit their progression, preventing vision loss, preserving kidney function, minimizing neurological pain and reducing the risk of limb loss, potentially saving billions of dollars and preserving quality of life in these patients. Current methods for diagnosing, stratifying, and monitoring T1D complications rely on a muddled collection of biomarker analyses, invasive procedures and physical exams. They have significant disadvantages that limit their ability to efficiently and effectively meet the demands of a growing, diverse diabetic population. These methods are expensive, labor-intensive, and time-consuming. For example, DR screening depends on the observation of altered ocular vascular morphology and necessitates costly imaging platforms, image processing equipment and digital image archiving, along with the need for highly skilled practitioners to operate the technology and interpret such results. DN relies on imprecise urine microalbumin testing or invasive kidney biopsy, and DPN is most frequently diagnosed following physical exam by a physician after patient discomfort or ulcer formation. The present technology can be used to screen a curated library of miRNAs shown to be involved in T1D DR and metabolic regulation in both surrogate control biofluids and clinical patient samples. In using clinical patient samples, the miRNA expression profiles can be correlated to T1D DR progression and characterize molecular subtypes with therapeutic value. Leveraging these early complication-specific miRNA signatures, the advanced diagnostic technology can provide fundamental and timely information to positively affect diagnosis and management of T1D DR, preserving quality of life for those suffering. This technology represents a broadly enabling approach, capable of providing comprehensive diabetic health information in a convenient and accessible platform.

In certain embodiments, the TRC platform is used for the detection and monitoring of psychiatric disorders. Utilizing miRNA as biomarkers for bipolar disorder, schizophrenia, major depressive disorder, substance abuse, and predicting responses to antidepressants can identify and stratify these disorders leading to more productive pharmaceutical intervention strategies.

In certain embodiments, the TRC platform is used for the detection and monitoring of gynecological diseases. Utilizing miRNA as biomarkers for endometriosis, infertility, and polycystic ovarian syndrome can identify and stratify these disorders leading to more productive pharmaceutical intervention strategies.

In certain embodiments, the TRC platform is used for the detection and monitoring of neurodegenerative diseases. Utilizing miRNA as biomarkers for traumatic brain injury, Parkinson's disease, Alzheimer's disease, Tourette's syndrome, Huntington's disease, Duchenne Muscular Dystrophy, Amyotrophic Lateral Sclerosis, and epilepsy can identify and stratify these disorders leading to more productive pharmaceutical intervention strategies.

In certain embodiments, the TRC platform is used for the detection and monitoring of autoimmune diseases. Utilizing miRNA as biomarkers for rheumatoid arthritis, lupus, multiple sclerosis, Crohn's disease, and graft vs host disease can identify and stratify these disorders leading to more product pharmaceutical intervention strategies.

In certain embodiments, the TRC platform is used for the detection and monitoring of cardiovascular diseases. Utilizing miRNA as biomarkers for hearts failure and heart disease can identify and stratify these disorders leading to more product pharmaceutical intervention strategies.

In certain embodiments, a TRC-based approach is used to diagnose a particular disease. In certain embodiments, a TRC-based approach is used to diagnose, monitor, and stratify a particular disease. In certain embodiments, a TRC-based approach is used to diagnose and monitor multiple diseases in a single reaction or test.

The methods described herein can be used, among other things, for determining the effect of a perturbation, including chemical compounds, mutations, temperature changes, growth hormones, growth factors, disease, or a change in culture conditions, on various target molecules, thereby identifying target molecules whose presence, absence or levels are indicative of particular biological states. In one embodiment, some aspects described herein can be used to elucidate and discover components and pathways of disease states. For example, the comparison of quantities of target molecules present in a disease tissue with "normal" tissue allows the elucidation of important target molecules involved in the disease, thereby identifying targets for the discovery/screening of new drug candidates that can be used to treat disease.

IV. Kits

The technology herein includes kits for evaluating the detection and quantitation of target nucleic acids in a sample. A "kit" refers to a combination of physical elements. For example, a kit may include, for example, one or more components such as probes, including without limitation specific primers, enzymes, reaction buffers, an instruction sheet, and other elements useful to practice the technology described herein. The kits may include one or more TRCs of one or more of the target nucleic acids as described herein. These physical elements can be arranged in any way suitable for carrying out the present methods. Kits may include a preselected panel of TRCs or individually selected based on application and preference.

Kits for detecting target nucleic acids may include, for example, a set of oligonucleotide probes. The probes can be provided on a solid support, as in an array (e.g., a microarray), or in separate containers. Kits can include further buffers, enzymes, labeling compounds, and the like. Any of the compositions described herein may be comprised in a kit. The kit may further include water and hybridization buffer to facilitate hybridization of the two nucleic acid strands.

The components of the kits may be packaged either in aqueous media or in lyophilized form. The container means of the kits will generally include at least one vial, test tube, flask, bottle, syringe or other container means, into which a component may be placed, and preferably, suitably aliquoted (e.g., aliquoted into the wells of a microtiter plate). Where there is more than one component in the kit, the kit also will generally contain a second, third or other additional container into which the additional components may be separately placed. However, various combinations of components may be comprised in a single vial. The kits of the present disclosure also will typically include a means for containing the nucleic acids, and any other reagent containers in close confinement for commercial sale. Such containers may include injection or blow molded plastic containers into which the desired vials are retained.

A kit will also include instructions for employing the kit components as well the use of any other reagent not included in the kit. Instructions may include variations that can be implemented. It is contemplated that such reagents are embodiments of kits of the present disclosure. Such kits, however, are not limited to the particular items identified above and may include any reagent used for the manipulation or characterization of the methylation of a gene.

The container means of the kits will generally include at least one vial, test tube, flask, bottle, or other container means, into which a component may be placed, and preferably, suitably aliquoted. Where there is more than one component in the kit, the kit also will generally contain additional containers into which the additional components may be separately placed. However, various combinations of components may be comprised in a container. The kits of the present disclosure also will typically include a means for packaging the component containers in close confinement for commercial sale. Such packaging may include injection or blow-molded plastic containers into which the desired component containers are retained.

V. Examples

The following examples are included to demonstrate preferred embodiments of the present disclosure. It should be appreciated by those of skill in the art that the techniques disclosed in the examples which follow represent techniques discovered by the inventor to function well in the practice of the present disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

Example 1

Generation of TRCs

TRCs were constructed from single-stranded DNA oligonucleotides (Integrated DNA Technologies). The 5' and 3' ends of the oligonucleotides were strategically placed within the toehold or bridge sequences and slow cooling under high-salt conditions forced the 5' and 3' ends to sit adjacent and encouraged the correct intra-molecular ligation by T4 DNA ligase (New England Biolabs). Treatment with exonucleases I and III eliminate unligated reactants. Gel electrophoreses was used to confirm the correct size and purity of the final TRC population. Multiple TRCs were generated for each miRNA and the final miRNA-specific TRC (i.e., one TRC per miRNA target) was selected after empirical testing.

Figures 4A, 4B:
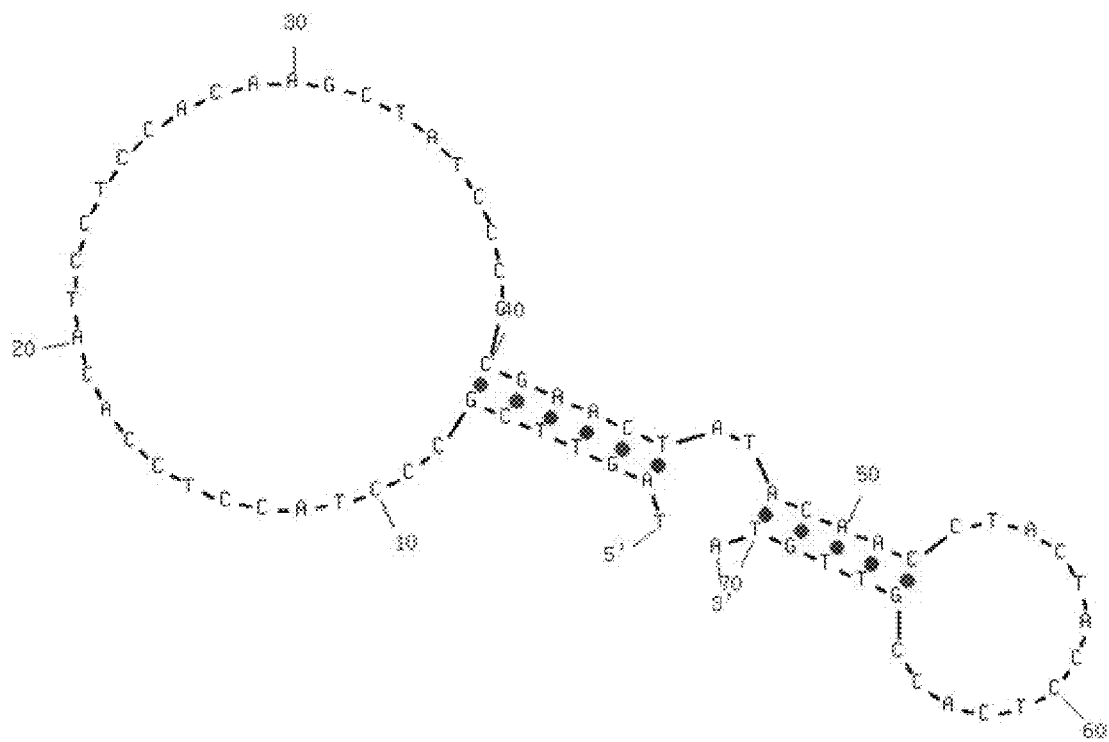
FIGS. 4A-4B: (A) Sequence and structure of miR-let-7a TRC (SEQ ID NO: 1) is depicted. (CTACTACCT (SEQ ID NO: 2): Toehold; CGAACTATACAAC (SEQ ID NO: 3): Switch Stem, one side; C: (de)stabilizing elements/other fillers with internal functionality; CCTACCTCCACATCCTCCACAAGCTATCCC (SEQ ID NO: 4): Probe(s) or other externally functional sequences). (B) Sequences of TRCs for miR-let-7g (SEQ ID NO: 5) and TRC for miR-21 (SEQ ID NO: 6).
Figure 5:
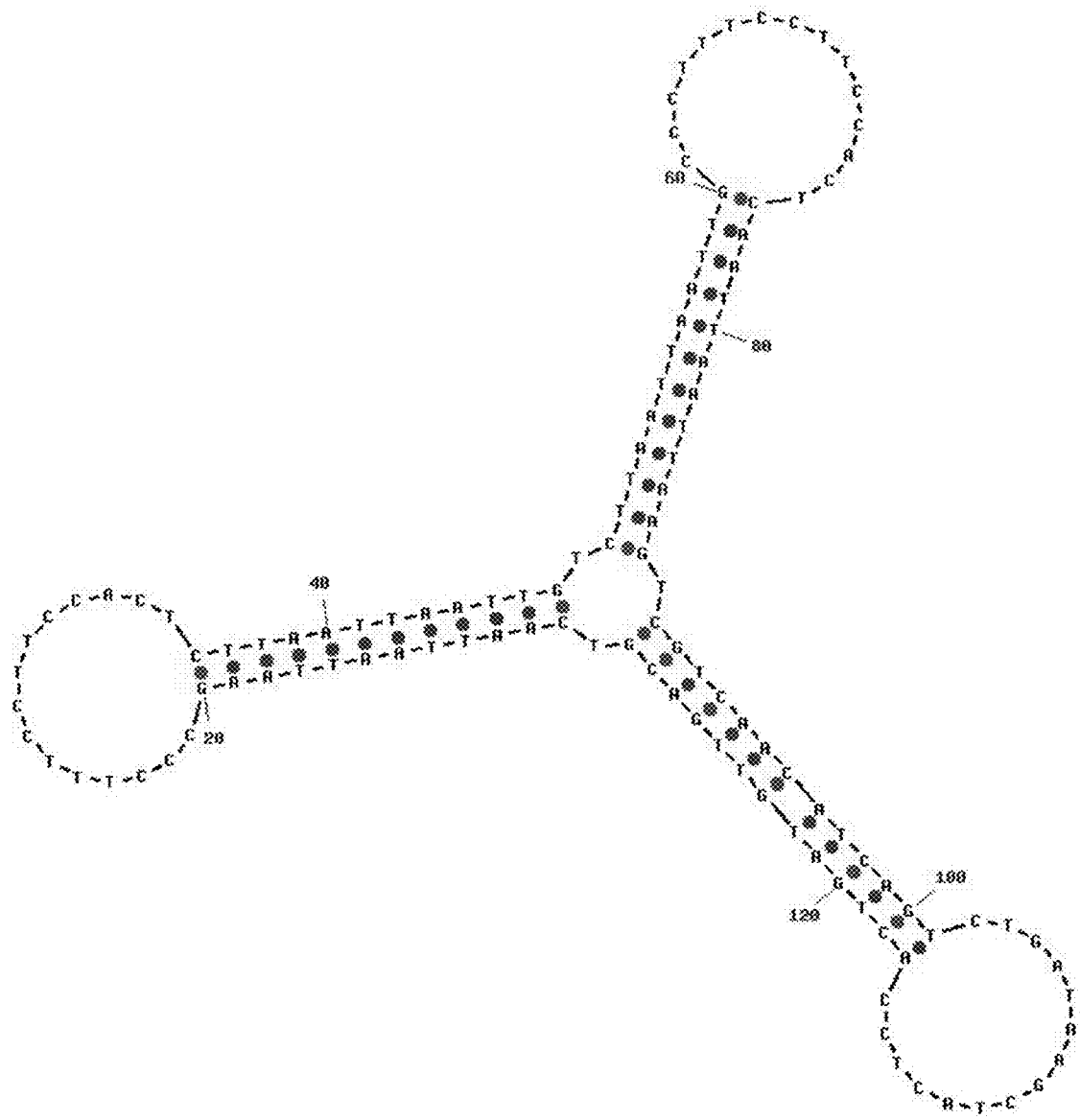
FIG. 5: Sequence and structure of a multi-looped miR-21 TRC (SEQ ID NO: 7).

As a demonstration of feasibility, TRCs were designed and synthesized targeted toward miRNAs in the *C. elegans* let-7 family. let-7 family members are rigorously used to test miRNA platform specificity as they frequently differ by a single nucleotide. Here, two functional TRCs (FIG. 4) were used to distinguish and quantify miR-let-7a (UGAGGUAGUAGGUUGUAUAGUU (SEQ ID NO: 8) and let-7g (UGAGGUAGUAGUUUGUAUAGUU (SEQ ID NO: 9));
these miRNAs differ by a single nucleotide at the 12th position (G>U, bolded and underlined). The miR-let-7a TRC had the sequence TAGTTCGCCCTAC CTCCACATCCTCCACAAGCTATCCCCGAACTAT ACAACCTACT ACCTCACCGTTGTA (SEQ ID NO: 1), with CTACTACCT (SEQ ID NO: 2) as the toehold. The miR-let-7g TRC had the sequence TAGTTCGCCCTAC CTCCACATCCTCCACAAGCTATCCCCGAACTATA CAAACTACT ACCTCACCGT TGTA (SEQ ID NO: 5).

The in silico design process utilized various bioinformatics applications (IDT OligoAnalyzer, VIennaRNA, and NuPack) to model toehold dynamics of various TRC architectures. Achieving favorable parameters for specific miRNA TMSD requires balancing thermodynamic properties (i.e., $T_m$, $\Delta G$, GC content of toehold sequence) with reaction conditions such as TRC and miRNA concentrations, salt concentration, and temperature. Furthermore, bridge, probing, and backbone TRC sequences were stringently designed to have minimal hybridization capacity with non-specific nucleic acids. Careful design of these sequences was necessary in order to eliminate false positive results brought on by promiscuous binding of non-targeted nucleic acids. Similar unaligned, alien sequences are available through the NIST External RNA Controls Consortium.

Promising candidate TRCs were synthesized and heuristically tested to identify sensitive and specific constructs. Preliminary data was obtained from 100 uL isothermal reactions (90 μL component mix plus 10 μL input) started and maintained throughout at 37° C. φ29 polymerase was selected for its high processivity in the elected temperature range, high fidelity, and robust strand-displacing properties. Significant alterations were made to the standard φ29 buffer conditions to achieve high sensitivity and specificity. All reactions were performed for 60 minutes in duration.

Figures 2A, 2B:
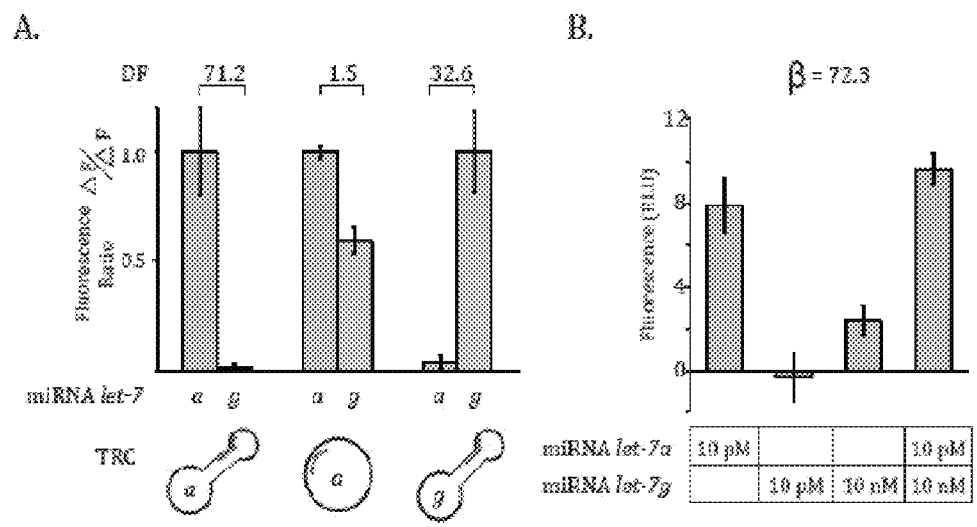
FIGS. 2A-2C: (A-B) Sensitivity and specificity of miR-let-7a and miR-let-7g TRCs. (C) Detection of miR-let-7a using a TRC on a qRT-PCR instrument and Sybr reagents.
Figure 2C:
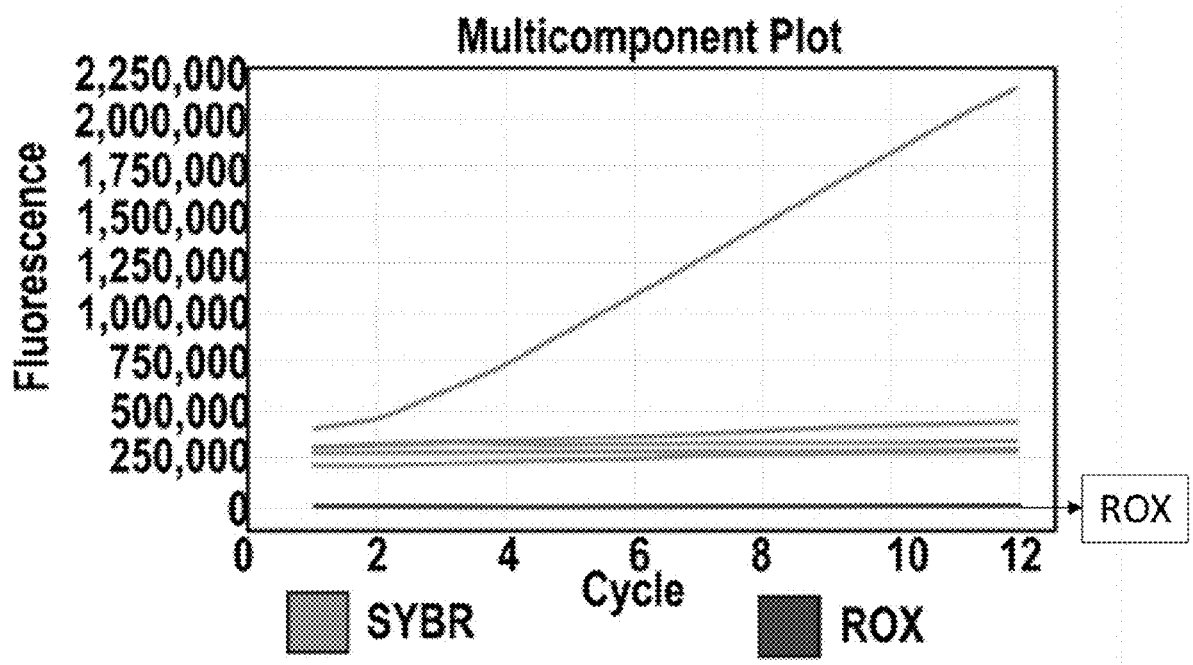

Molecular beacons, which are self-quenching hairpin probes containing a fluorophore on the 5' end, were utilized to quantify TRC RCR products. These beacons bind to the replicated products in a similar manner as the envisioned fluorescent probes but permit rapid quantitation on a microplate reader to investigate initial specificity and sensitivity. As shown in FIG. 2A, the incorporation of a toehold structure directed toward the target miRNA endows individual TRCs with exceptional specificity. A circular, single-stranded miR-let-7a TRC-control (no toehold present) displays very little ability to discriminate between miR-let-7a and miR-let-7g with only a 1.5 fold discrimination factor (middle construct). The toehold containing TRCs however, directed at either miR-let-7a or miR-let-7g, display discrimination factors (DF) of 71.2 and 32.6 over their counterpart miRNA, respectively. This metric surpasses the stated specificity of other commercially available single-molecule platforms and suggests that with careful design, TRCs can be finely tuned to distinguish between highly similar miRNA molecules. Furthermore, the sensitivity of the miR-let-7a TRC, as shown in FIG. 2B, indicates that this approach has the ability to quantitate miRNAs at exceptionally low concentrations, even in a background of untargeted miRNAs. In this assay, miR-let-7a was present at 10 pM while miR-let-7g was present at 1 nM (100 fold excess). The miR-let-7a TRC still achieves a robust β factor of 72.3; the β factor accounts for untargeted background. As the microplate reader approach may be underpowered; the platform take advantage of high-power fluorescent imaging to interrogate each individual replicated TRC on high-density ordered arrays, permitting far more sensitive quantitation at the single-molecule level.

Example 2

TRC Analysis of Circulating Pancreatic Cancer miRNA Signatures

Pancreatic cancer (PaCa) is a fundamentally challenging malignancy to combat. Most cases are diagnosed in advanced stages with few effective medical options, and survival rates are abysmally low (5-20% over five years). Many recent studies have outlined the utility of miRNAs, and specifically cell-free miRNAs, in the course of PaCa for early detection and disease surveillance.

TRC platform functionality is demonstrated by targeting nine miRNA species that have been detected at elevated levels in the plasma of pancreatic cancer patients by currently available methods. These miRNAs include miR-10b, miR-21, miR-25, miR-106b, miR-155, miR-196a, miR-210, miR-212, and miR-221. The TRC platform is further validated by two sets of control TRCs to enable normalization across samples and confirm assay functionality including four miRNA targets present in the plasma of healthy humans miR-15b, miR-16, miR-24, miR-217 and three miRNA targets present only in *C. elegans* with no sequence similarity to the human genome cel-miR-39, -54, -238. Control TRCs are designed according to the same process as target TRCs. The TRCs are constructed as described in Example 1.

In order to distinguish the products of 16 target miRNA TRCs in multiplex, two additional independent, probing sequences are incorporated into the TRC, each with the potential to bind one of four AlexaFluor labelled beacons. The two-color combination and order of probes binding to any particular nanosphere is unique and indicative of a particular miRNA.

Following replicated TRC production by RCR and the formation of replicated nanospheres from the various multiplex miRNA testing populations, the products will be pipetted individually on to separate ordered arrays. A brief incubation period permits replicated nanospheres to adequately bind to the functionalized surface. Arrays are then prepared for probe hybridization by rinsing in a neutral pH buffer to remove contaminants from the initial reaction.

In order to approximate the significant background populations encountered in actual plasma samples, size selected RNA populations are isolated from commercially available donor plasma samples using commercially available reagents and protocols (Qiagen). Prior to small RNA isolation, plasma samples are spiked with mixed populations of TRC-targeted miRNAs. Such populations include titrations (1 nM to 1 fM) of all target miRNAs, human control miRNAs and *C. elegans* control miRNAs.

Following targeted miRNA spike-in, the entire population of short RNA present in the plasma (human and microbial RNA, ncRNAs, target miRNAs) is extracted, purified, and quantified using the optimized array-based approach.

Example 3

TRC Diagnostic Analysis of Oral Pathogenic Nucleic Acids

Figure 1B:
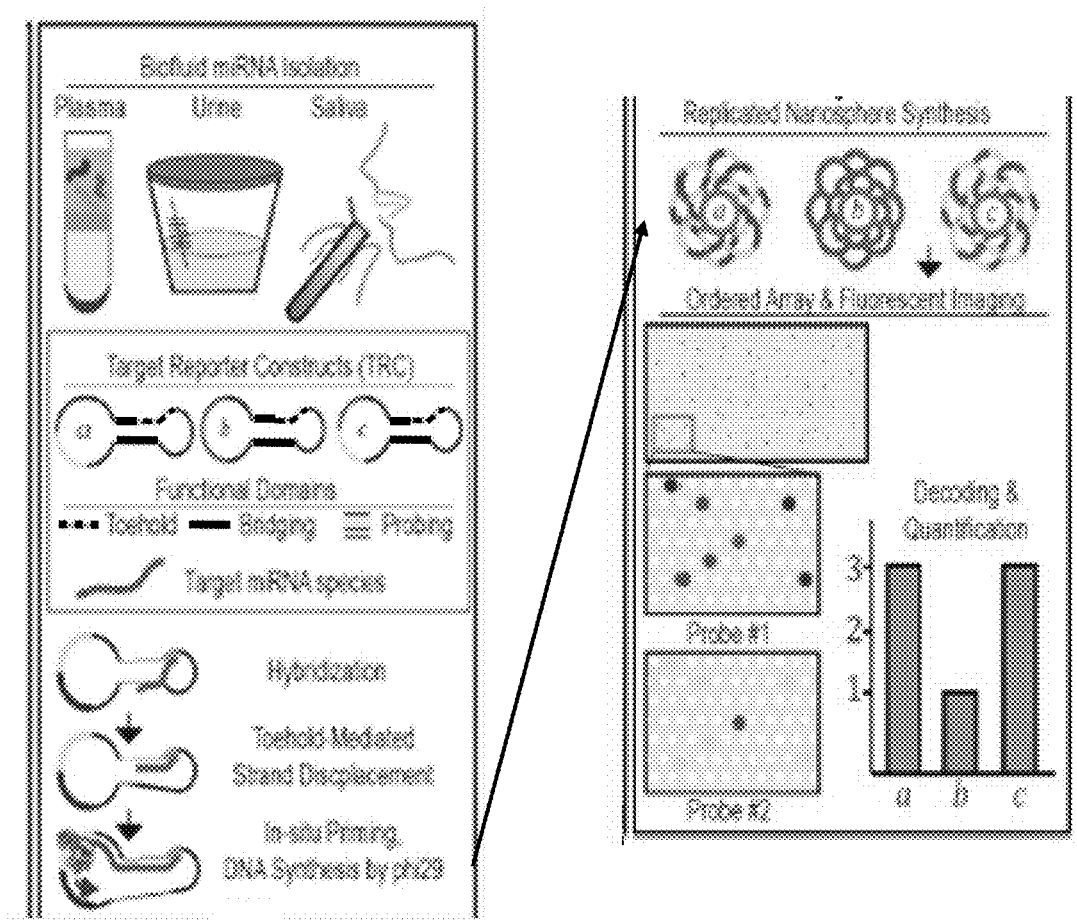
Figure 1C:
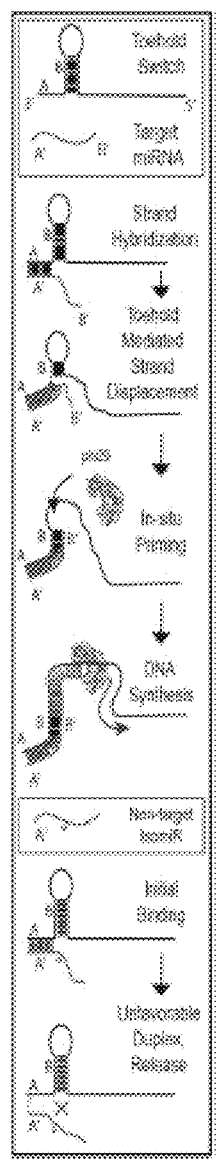
Figure 1D:
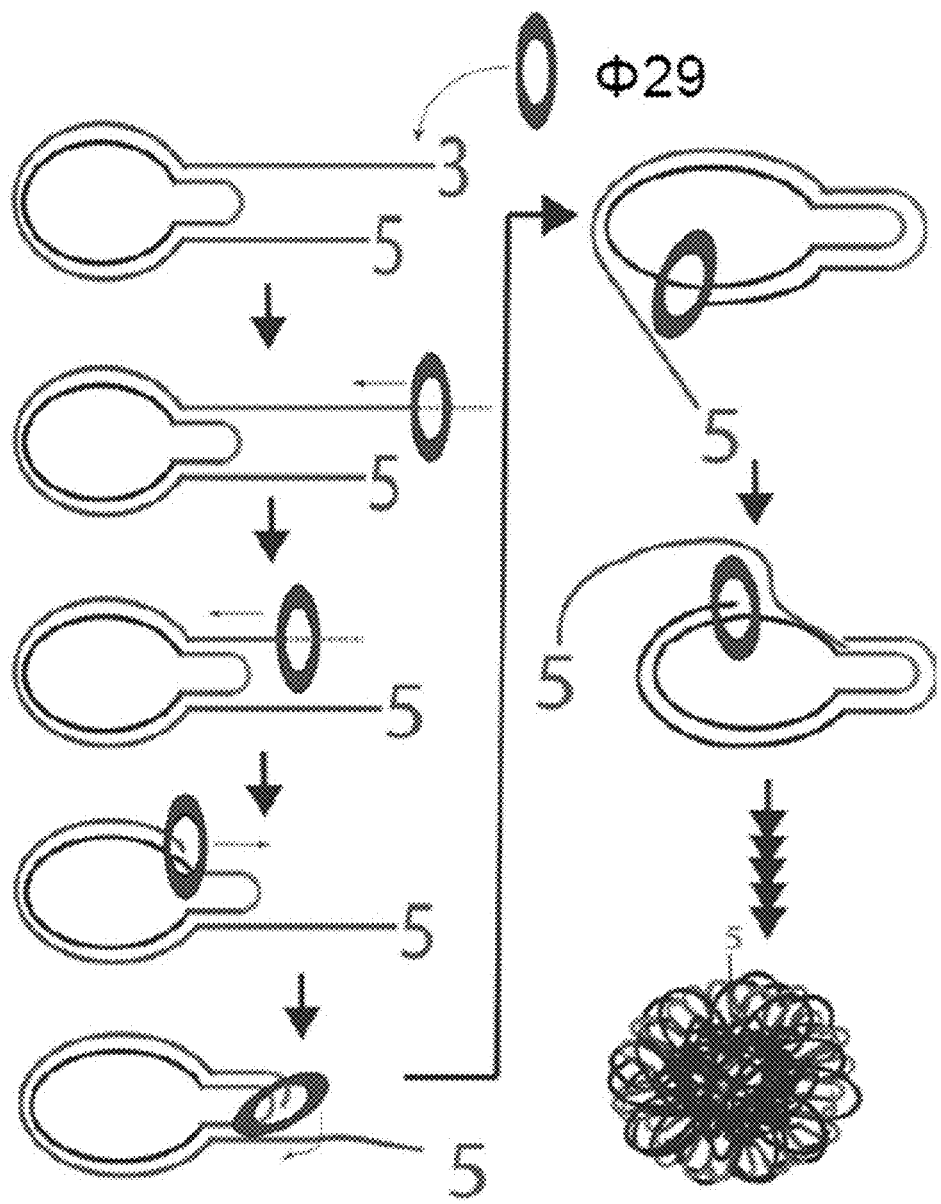
Figure 1E:
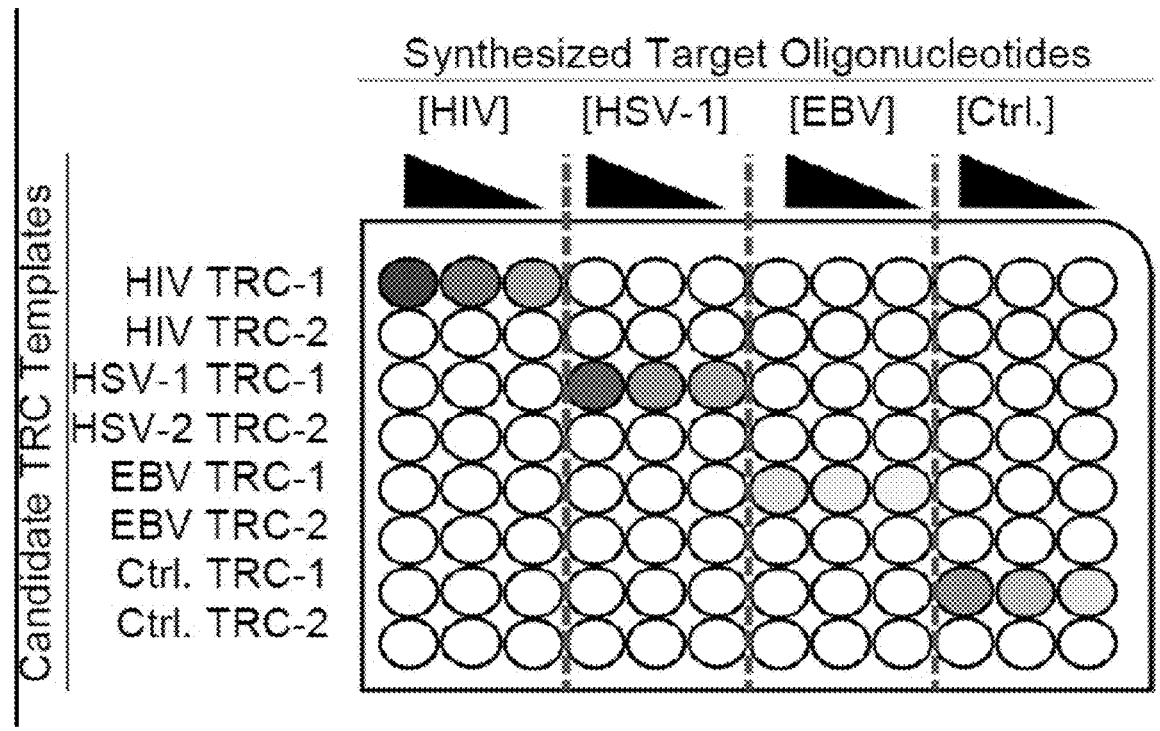
Figure 1F:
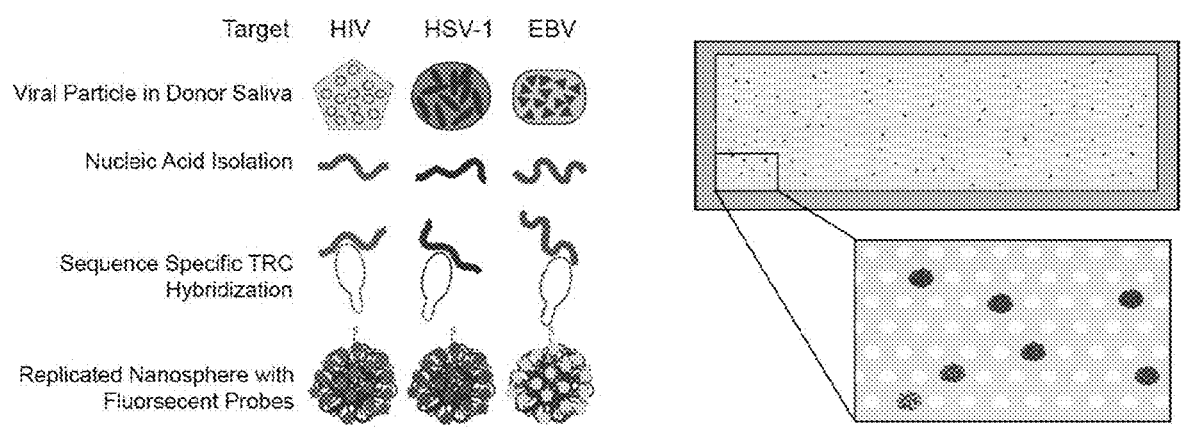

Multiplex pathogen detection of HIV, HSV-1, and EBV viral sequences is achieved by several TRC configurations (FIGS. 1A and 1E). TRCs are constructed from several ligated oligonucleotides under dilute conditions and complimentary junction-spanning RNA splints and SplintR Ligase, obtained from New England Biolabs, are added to encourage intra-molecular ligation. Multiple TRCs are generated specific for each pathogen, and these may be used singly or in combination.

To transform these target sequences into functional primers that may initiate rolling circle replication (RCR), the overhanging 3'-end sequences were removed up to the double-stranded complimentary region and present a 3'-OH group. This method, outlined in FIG. 1D, leverages the intrinsic 3'-exonuclease (3'-exo) activity exhibited by DNA polymerases or a separate standalone exonuclease. The inherent 3'-exo activity of φ29 DNA polymerase was shown to remove the 3'-overhanging ssDNA and ssRNA, albeit with different efficiencies from hybridized target nucleic acids and initiate RCR. Similar to φ29 DNA polymerase, Exonuclease T displays different efficiencies in digesting ssDNA and ssRNA 3'-overhanging sequences. Both DNA polymerases possess isothermal, high processivity, and strand-displacing qualities with Bst DNA polymerase having the added advantage of thermostability, and thus potentially higher assay specificity. The intrinsic properties of these DNA polymerase are important factors that contribute to the efficient and robust creation of replicated nanospheres.

Synthesized oligonucleotides (ssDNA, ssRNA, and dsDNA) with varying degrees of mismatching to the TRC pathogen sequence regions are used to confirm hybridization, priming, exonuclease resection of the 3'-overhanging sequences and the initiation of DNA synthesis through RCR.

Successful reactions produce high-molecular weight (>70 kb) DNA products that are confirmed through gel electrophoresis. RCR reactions are evaluated using molecular beacons, which target accessory sequences on the replicated nanospheres, using a fluorescent plate reader (FIG. 1B). Following replicated nanosphere creation by RCR from the various populations, the products will be pipetted individually on to different patterned arrays. Arrays are then prepared for probe hybridization by rinsing in a neutral pH buffer to remove contaminants from the initial reaction.

Fluorescent probes are used to interrogate the bound replicated nanospheres. Four different and distinct fluorescent probes are utilized, one color for all replicated nanospheres produced from TRCs targeting a given specific pathogen (HIV, HSV-1, and EBV) or the positive control TRC. Washed arrays containing fluorescent probe-hybridized replicated nanospheres are imaged using an epi-fluorescence detection microscope. The number of pathogen-specific fluorescence signals is significantly correlated with target oligonucleotide concentrations. Control and pathogen titration series and mixed oligonucleotide populations indicate any platform bias.

Pathogenic saliva samples are prepared (~200-400 µL) from artificial and/or commercially obtained donor saliva spiked with various concentrations of commercially available viral mimics of HIV, HSV-1 and EBV (FIG. 1E). The viral mimics, available from AcroMetrix and used as diagnostic controls, represent, intact, encapsidated viral particles. The artificial mimic pathogens are initially obtained as a stock solution of viral particles in plasma. This is further diluted in the saliva according to a titration series ($10^{10}$ viral particles, 1.0 log steps). All samples contain the control TRCs and target oligonucleotide. Bulk nucleic acids present in the saliva (human and microbial DNA and RNA, HIV RNA, HSV-1 and EBV DNA, control oligonucleotide) are extracted, purified, and quantified according to previously outlined methods and commercially available reagents (e.g., MagJET Viral DNA and RNA kit, µDrop DNA quantification plate, Thermo Scientific).

Significant importance should be placed on obtaining a digital, quantified population assessment that reflects the expected viral load. System biases and inefficiencies may be apparent using the surrogate oral biospecimens and platform adjustments will be made accordingly.

The limits of detection based on previously collected data may place values at: HIV infected individuals may have as few as 100 copies/mL in the saliva; HSV-1 in saliva oral swabs may be present at 1,000 copies/mL, but can be detected at 10-fold lower concentrations; EBV has been reported at considerably higher levels, approaching $10^5$ copies/mL.

Example 4

TRC Diagnostic Analysis of Oral Pathogenic Nucleic Acids

Figure 3:
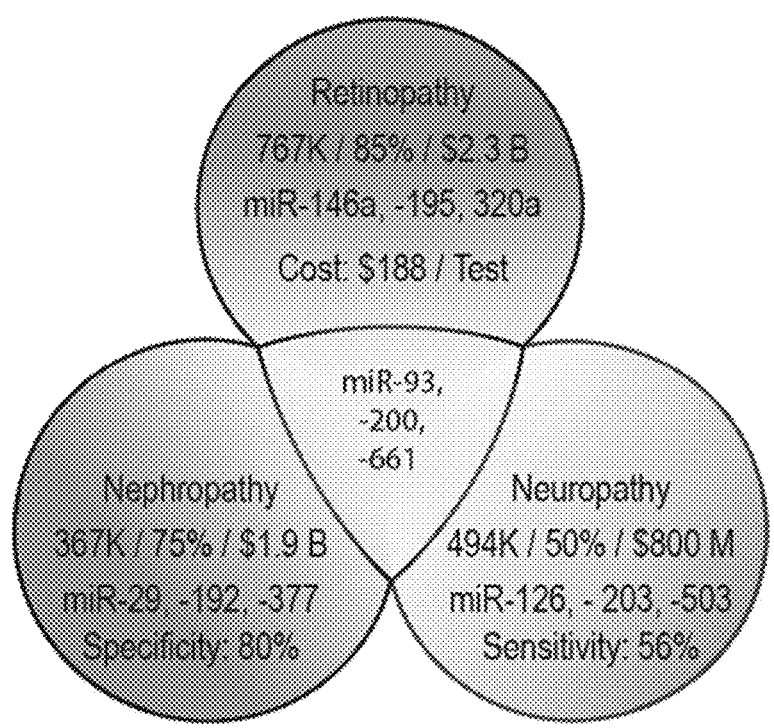
FIG. 3: Microvascular complications in Type I Diabetes: Complications are presented with Type I diabetes specific data for the United States including the number of patients at a given time, overall lifetime risk of development and annual healthcare expenditures. Target miRNAs are listed for each complication along with three altered microvascular miRNA targets.
Figure 3:
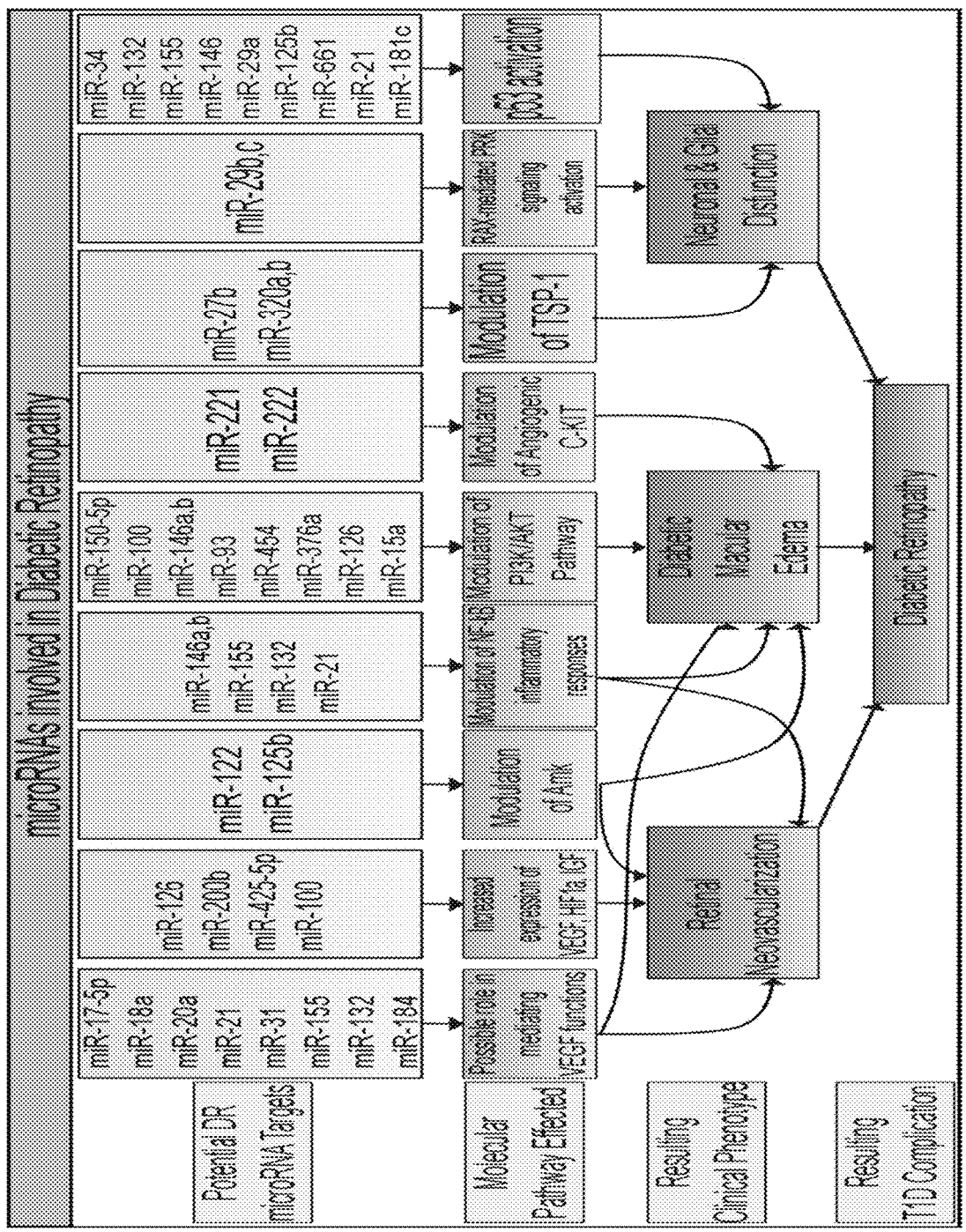

The diagnostic platform is used to interrogate microRNA populations with immediate utility for T1D DR. 30 miRNAs were selected with significant association to DR initiation and progression in patient populations (FIG. 3). To normalize across samples and confirm assay functionality, two sets of controls are utilized: (i) two diabetic non-responsive miRNA targets present in the biofluids of all humans (miR-15b and miR-16) and (ii) two miRNA targets present only in *C. elegans* with no sequence similarity to the human genome (cel-miR-39 and miR-54). The latter is spiked in to samples (both surrogate and clinical) to control for run-specific variation and isolation efficiency.

Following TRC validation, replicated nanospheres will be randomly loaded onto functionalized, high-density ordered arrays. Fluorescent probes are used to interrogate replicated nanospheres at this stage. High-resolution imaging is performed using a Nikon Ti-E epifluorescence microscope. Stitching and analysis of the four-color array images is carried out using Nikon Elements software and an in-house deconvolution program based in ImageJ. Incorporation of software (e.g., BlobFinder) may aid in identifying and defining individual nanospheres. The probe hybridization reactions and image collection are automated with standard microfluidic devices and modifications to the existing microscope.

Small RNA populations isolated from commercially available surrogate plasma, saliva, and urine specimens recapitulate the significant background nucleic acid populations encountered in patient samples. These biofluids are spiked with mixed populations of TRC-targeted miRNAs. Such populations include titrations (1 fM to 1 nM) of all target miRNAs, human control miRNAs and *C. elegans* control miRNAs. Size selected RNA populations are isolated using commercially available reagents and protocols (e.g., Qiagen miRNeasy). The entire population of small RNAs present in the specimen (human and microbial RNA, ncRNAs, target miRNAs) is extracted, purified, and quantified using the optimized and automated approach.

The platform is evaluated using a cohort of 30 to 50 clinically relevant DR patient samples. Leveraging the platforms high-throughput screening capabilities, the platform is used to characterize the miRNA populations in patient samples. The data from 50 targets is used to yield a highly correlative miRNA signature for DR risk and severity as well as analysis of archived samples for patients that went on to develop DR and samples showing rapid progression to vision loss.

Example 5

TRC Technology Applied to Bead-Based Detection

Two sets of miRNA targets are used to assess the Luminex technology using surrogate plasma samples. First, a group of ten control *C. elegans* miRNA targets with no sequence similarity to the human genome but with high sequence homology to each other is used to assess workflow efficiency, control for run-to-run variation, define the limits of TRC specificity, sensitivity, and dynamic range. Furthermore, the *C. elegans* controls are used in constructing a standard curve for quantification. A second group of ninety miRNA targets are used to prove the robust nature of the design application and the platform's ability to quantitate potential real-world miRNA biomarkers. This second set of targets is derived from the NanoString nCounter miRNA Discovery panel to facilitate comparison.

Commercially available, healthy human plasma are used as a surrogate starting material. Fifty surrogate samples are spiked with various combinations of the ten *C. elegans* control miRNAs representing titrations ranging from 1 fM to 1 nM.

Two input methods are analyzed: crude plasma samples and isolated, size-specific small RNA populations. The entire population of small RNAs (<200 bp) present in the specimen (human and microbial RNA, ncRNAs, target miRNAs, etc.) is extracted, purified, and quantified using the standard reagents and protocols (i.e., Qiagen miRNeasy). The nucleic acid populations in plasma recapitulates the significant background encountered in patient samples.

The bioinformatics pipeline is employed to design and construct a unique TRC for each of the ten *C. elegans* and 90 native target miRNAs. Luminex MagPlex beads contain carboxyl groups to facilitate the attachment of numerous macromolecules, including nucleic acids. As TRCs are circular in nature, amino-modifier C6 dT phosphoramidates are used during synthesis of TRC oligonucleotides for coupling to Luminex beads. TRC-specific, complementary, secondary primers are also attached to the Luminex beads to further extend the unique replicated TRC products, covalently attaching such products to the beads. This process results in a highly-intertwined but discrete, bead-product detectable on the Luminex 200 platform (FIG. 6).

Functionalized microspheres are purified by magnetic isolation and combined into a single reaction tube. RCR reaction components (buffer, nucleotides, polymerase, microspheres) are combined with a crude or purified surrogate sample and incubated under isothermal conditions. The replicated product of an individual TRC RCR reaction is a single, long nucleic acid composed of hundreds of concatenated and complimentary TRC sequences. To covalently attach the RCR product, a secondary primer is employed in the strand-displacing reaction; this effectively induces rolling circle amplification (RCA) (FIG. 6). Microspheres and the bound RCR/RCA product are isolated using magnetic separation.

To label replicated TRC products for detection on Luminex platforms, fluorescently-labelled nucleotides (i.e., Fluorescein-12-dCTP; PerkinElmer) are utilized. Previous experience with Bst and Bsu polymerases have demonstrated efficient incorporation of such modified nucleotides in RCR. Alternatively, an intercalating dye such as Sybr could be used to detect replicated TRCs bound to beads.

Microsphere analysis is carried out according to the standard operating protocol provided by Luminex. The Luminex 200 instrument is capable of simultaneously analyzing up to 100 unique reactions (i.e., 100 miRNA targets) with more advanced versions of the technology capable of handling up to 500 unique reactions. Luminex's xPONENT software is used for continuous monitoring and quantification of all target miRNAs.

Example 6

TRC Technology for Research and Diagnosis of Endometriosis

Figure 7A:
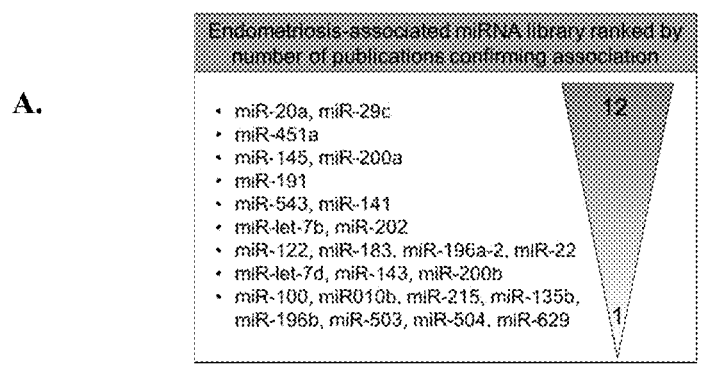
FIGS. 7A-C: (A) Endometriosis associated miRNAs. (B) TRC validation methods using microplate- and qRT-PCR-based methods. qRT-PCR based approach for quantitation of miRNAs using TRCs. (C) Endometriosis induced mouse model, validation approach for an endometriosis miRNA signature, and idealized data showing a correlation between plasma and tissue derived miRNA.
Figure 7B:
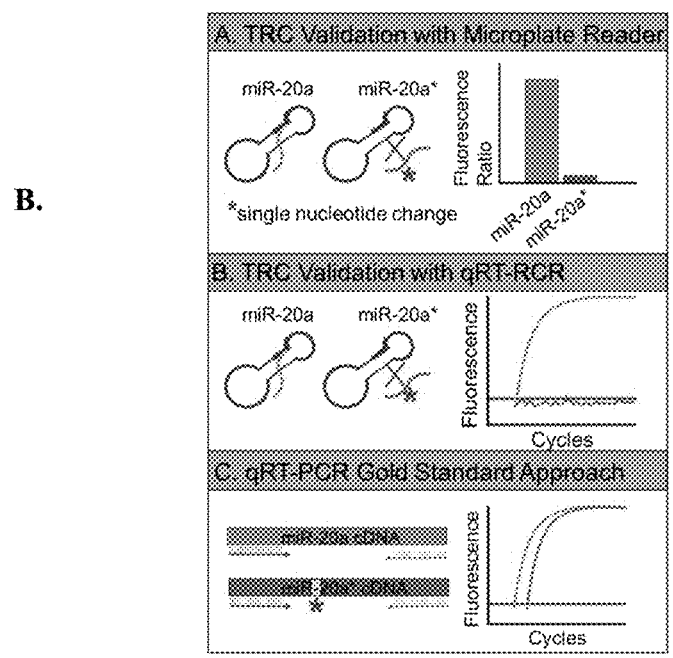
Figure 7C:
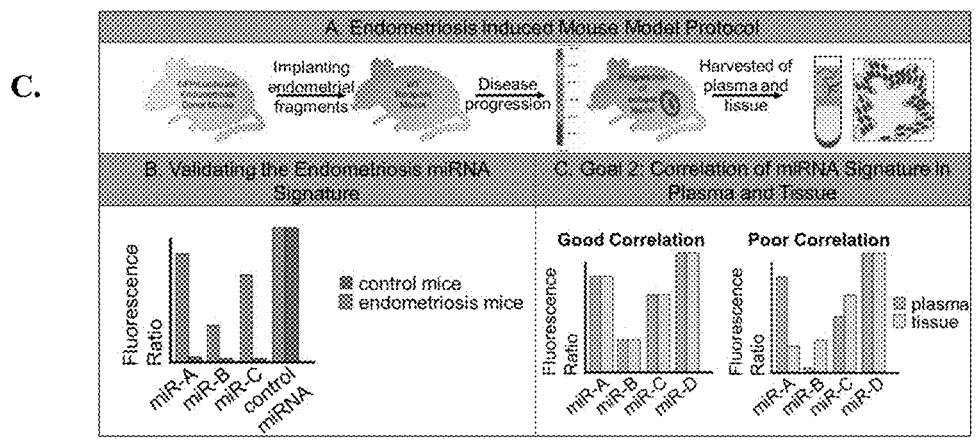

An endometriosis mouse model is used to assess TRCs as a viable research tool and clinical diagnostic test. Endometriosis is induced by transplanting endometrial fragments from Luciferase/GFP donor mice, allowing for live monitoring and imaging of disease progression. A list of 25 miRNAs with significant association to the presence of endometriosis in patient populations was developed (FIG. 7).

To normalize across samples and confirm assay functionality, each TRC is assayed against the target miRNA from the library and biologically similar or synthetically similar miRNA target. These biologically similar targets may differ by 1 or 2 base-pairs. If no biologically similar miRNA exists, then a synthetic target is used.

Interrogation of specificity and sensitivity is performed in three ways. First, similar to Example 1, specificity is verified with the fluorescent microplate reader, which provides simple output data to determine if the TRC needs to be redesigned for its miRNA target. Once a target is verified on the microplate reader, the reaction conditions for qRT-RCR are determined (FIG. 7). Lastly, the TRC qRT-RCR is compared to the sensitivity and specificity of current miRNA qRT-PCR detection protocols (FIG. 7), providing a direct comparison of the present technology to the current gold standard for clinical diagnostic labs.

The endometriosis miRNA signature detection capabilities of the TRC library is determined in 5 endometriosis-induced mice and 5 control mice. To confirm noninvasive growth of ectopic lesions in mice with endometriosis, Luciferase (luc)/GFP mice [FVB-Tg (CAG-luc,-GFP) L2G85Chco/FathJ mice, Jackson Laboratory] are employed. In brief, endometrial fragments isolated from Luc/GFP donor mice are implanted into wild type recipient mice (non-transgenic littermates) (FIG. 7).

Endometriosis is induced in 6-week-old female mice and allowed to progress for two weeks. After two weeks, vaginal cells are isolated from endometriosis-induced mice and histologically examined every day for a subsequent two weeks. These cells are stained with Crystal Violet to determine the estrus cycle of each mouse. Endometrial tissue and blood is harvested at the proestrus stage of each mouse. Bioluminescence imaging of the ectopic lesions in each mouse is captured once a week to track lesion growth and development.

All mice are euthanized in compliance to American Veterinary Medical Association protocols. From these harvested samples, miRNA is isolated and interrogated for the presence of the endometriosis TRC library.

The sensitivity and specificity of a subset of control TRCs is evaluated in a small set (five [5] healthy, endometriosis-free patients) of clinical samples from women (FIG. 6). These clinical samples are both uterine tissue and plasma taken from the same patient to correlate the amount miRNA detected in each biospecimens miRNA will be isolated from both sets of biospecimens and evaluated using TRCs that target miRNAs that are present in healthy individuals and have no disease indication (FIG. 7).

All of the compositions and methods disclosed and claimed herein can be made and executed without undue experimentation in light of the present disclosure. While the compositions and methods of the present disclosure have been described in terms of preferred embodiments, it will be apparent to those of skill in the art that variations may be applied to the methods and in the steps or in the sequence of steps of the methods described herein without departing from the concept, spirit and scope of the present disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present disclosure as defined by the appended claims.

What is claimed is:

1. A target reporter construct (TRC) for detecting target nucleic acids, the TRC being a closed, partially single-stranded nucleic acid comprising:
   (a) one or more target sequences complementary to the target nucleic acids, wherein the target sequences are toehold switches comprising a short duplex structure with an overhang;
   (b) a bridge sequence forming a double-stranded portion of the TRC, wherein the bridge sequence comprises one or more stabilizing sequences for the formation of nanospheres during replication; and
   (c) an accessory sequence comprising a multifunctional probe sequence.

2. The TRC of claim 1, wherein the TRC comprises standard canonical bases, modified bases, non-natural bases, or any combination of the bases thereof.

3. The TRC of claim 2, wherein the target nucleic acids are single-stranded DNA (ssDNA), double-stranded DNA (dsDNA), or single-stranded RNA (ssRNA).

4. The TRC of claim 3, wherein the ssRNA is microRNA (miRNA).

5. The TRC of claim 3, wherein the ssRNA is a non-coding RNA (ncRNA).

6. The TRC of claim 1, wherein the TRC comprises two target sequences separated by a bridge sequence.

7. The TRC of claim 1, wherein the bridge sequence is between the target sequence and accessory sequence.

8. The TRC of claim 1, wherein the TRC comprises two or more bridge sequences.

9. The TRC of claim 1, wherein the accessory sequence further comprises at least a second probe sequence.

10. The TRC of claim 9, wherein the first probe sequence and distinct second probe sequence form a unique multiplex probe signature.

11. The TRC of claim 10, wherein the unique multiplex probe signature further comprises a third, fourth, or fifth probe sequence.

12. The TRC of claim 1, wherein the multifunctional probe sequence comprises a binding sequence that facilitates localization to an oligonucleotide array.

13. The TRC of claim 1, wherein the TRC is between 50 and 100 nucleotides in length.

14. The TRC of claim 1, wherein the TRC is between 100 and 500 nucleotides in length.

15. A replicated TRC comprising concatenated monomer repeats of a TRC according to claim 1, wherein the replicated TRC is produced from rolling circle replication (RCR) and rolling circle amplification (RCA).

16. A method of detecting a target nucleic acid comprising:
   (a) obtaining target reporter constructs (TRCs) according to claim 1;
   (b) contacting the TRCs with a population of target nucleic acids, wherein the target nucleic acids within the population hybridize to the complementary target sequence of a target-specific TRC;
   (c) performing rolling circle replication (RCR), thereby obtaining replicated TRCs;
   (d) introducing at least one detectable moiety, wherein the at least one detectable moiety binds the probe sequence of the replicated TRC; and
   (e) detecting the at least one detectable moiety, thereby detecting the target nucleic acid.

17. The method of claim 16, wherein performing RCR comprises introducing a strand-displacing polymerase.

18. The method of claim 17, wherein the strand-displacing polymerase is a DNA polymerase or RNA polymerase.

19. The TRC of claim 1, wherein the one or more stabilizing sequence comprise a palindromic sequence.

20. The TRC of claim 1, wherein the one or more stabilizing sequence comprise a low complexity, repetitive sequence.

* * * * *